United States Patent
Babich et al.

(10) Patent No.: US 9,120,837 B2
(45) Date of Patent: Sep. 1, 2015

(54) METAL COMPLEXES OF POLY(CARBOXYL)AMINE-CONTAINING LIGANDS HAVING AN AFFINITY FOR CARBONIC ANHYDRASE IX

(71) Applicant: Molecular Insight Pharmaceuticals, Tarrytown, NY (US)

(72) Inventors: John W. Babich, New York, NY (US); Craig Zimmerman, Topsfield, MA (US); John L. Joyal, Melrose, MA (US); Genliang Lu, Winchester, MA (US); Shawn Hillier, Danvers, MA (US); Kevin P. Maresca, Tewksbury, MA (US); John Marquis, Nashua, NH (US)

(73) Assignee: MOLECULAR INSIGHT PHARMACEUTICALS, Tarrytown, NY (US)

( * ) Notice: Subject to any disclaimer, the term of this patent is extended or adjusted under 35 U.S.C. 154(b) by 0 days.

(21) Appl. No.: 13/734,534

(22) Filed: Jan. 4, 2013

(65) Prior Publication Data
US 2013/0216477 A1    Aug. 22, 2013

Related U.S. Application Data

(60) Provisional application No. 61/584,146, filed on Jan. 6, 2012.

(51) Int. Cl.
| A61K 51/00 | (2006.01) |
| A61M 36/14 | (2006.01) |
| C07F 13/00 | (2006.01) |
| C07D 403/12 | (2006.01) |
| C07D 233/64 | (2006.01) |
| C07D 417/12 | (2006.01) |
| C07D 249/04 | (2006.01) |
| C07D 233/00 | (2006.01) |

(52) U.S. Cl.
CPC ............ *C07F 13/005* (2013.01); *C07D 233/64* (2013.01); *C07D 249/04* (2013.01); *C07D 403/12* (2013.01); *C07D 417/12* (2013.01); *C07D 233/00* (2013.01)

(58) Field of Classification Search
USPC ........................................................ 424/1.65
See application file for complete search history.

(56) References Cited

U.S. PATENT DOCUMENTS

| 2,730,456 A | 1/1956 | Green, et al. |
| 2,730,457 A | 1/1956 | Green, et al. |
| 2,800,457 A | 7/1957 | Green, et al. |
| 3,527,789 A | 9/1970 | Payne |
| 3,625,214 A | 12/1971 | Higuchi |
| 4,272,398 A | 6/1981 | Jaffe |
| 4,798,734 A | 1/1989 | Kaneda |
| 4,885,136 A | 12/1989 | Katayama et al. |
| 4,888,136 A | 12/1989 | Chellapa et al. |
| 4,906,474 A | 3/1990 | Langer et al. |
| 4,925,673 A | 5/1990 | Steiner et al. |
| 5,442,088 A | 8/1995 | Hoffmann |
| 5,672,592 A | 9/1997 | Jackson et al. |
| 5,739,123 A | 4/1998 | Norcini et al. |
| 5,795,877 A | 8/1998 | Jackson et al. |
| 5,824,662 A | 10/1998 | Slusher et al. |
| 5,880,112 A | 3/1999 | Jackson et al. |
| 6,071,965 A | 6/2000 | Jackson et al. |
| 6,479,470 B1 | 11/2002 | Kozikowski et al. |
| 6,528,499 B1 | 3/2003 | Kozikowski et al. |

(Continued)

FOREIGN PATENT DOCUMENTS

| CN | 102272102 | 12/2011 |
| EP | 0 544 412 | 6/1993 |

(Continued)

OTHER PUBLICATIONS

Remington's: the Science and Practice of Pharmacy, Seventeenth Edition, p. 1795, 1985.*

(Continued)

*Primary Examiner* — Michael G Hartley
*Assistant Examiner* — Melissa Perreira
(74) *Attorney, Agent, or Firm* — Gilberto M. Villacorta; Jeffrey R. Lomprey; Foley & Lardner LLP

(57) ABSTRACT

The present invention is directed to CA IX inhibitors that conform to Formula I where the substituents X, A, B, D, E, E' and G are as defined above.

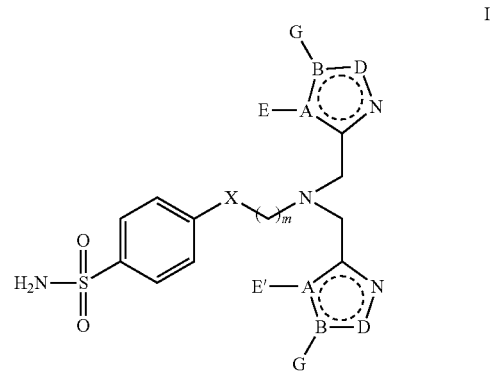

Also described are Pt, $^{64}$Cu, $^{186}$Re, $^{188}$Re and $^{99m}$Tc metal complexes of Formula I compounds which find use as candidate agents for imaging tumors.

31 Claims, 4 Drawing Sheets

(56) References Cited

U.S. PATENT DOCUMENTS

| | | | |
|---|---|---|---|
| 7,381,745 | B2 | 6/2008 | Kozikowski et al. |
| 8,211,402 | B2 * | 7/2012 | Babich et al. ............ 424/1.65 |
| 2003/0100594 | A1 | 5/2003 | Masferrer et al. |
| 2003/0235843 | A1 | 12/2003 | Babich et al. |
| 2004/0002478 | A1 | 1/2004 | Kozikowski et al. |
| 2004/0054190 | A1 | 3/2004 | Pomper et al. |
| 2004/0191174 | A1 | 9/2004 | Linder et al. |
| 2004/0209921 | A1 | 10/2004 | Bridger et al. |
| 2005/0038258 | A1 | 2/2005 | Koike et al. |
| 2006/0057068 | A1 | 3/2006 | Supuran et al. |
| 2006/0155021 | A1 | 7/2006 | Lenges et al. |
| 2006/0155146 | A1 | 7/2006 | Lenges et al. |
| 2006/0198785 | A1 | 9/2006 | Santos et al. |
| 2008/0176821 | A1 | 7/2008 | Kozikowski et al. |
| 2008/0227962 | A1 | 9/2008 | Mazzanti |
| 2009/0175794 | A1 | 7/2009 | Zimmerman et al. |
| 2009/0192182 | A1 | 7/2009 | Kusumi et al. |
| 2010/0178246 | A1 | 7/2010 | Babich et al. |
| 2010/0178247 | A1 | 7/2010 | Babich et al. |
| 2010/0183509 | A1 * | 7/2010 | Babich et al. ............ 424/1.65 |

FOREIGN PATENT DOCUMENTS

| | | |
|---|---|---|
| EP | 0 878 463 | 11/1998 |
| EP | 1 389 460 | 2/2004 |
| EP | 1 550 657 | 7/2005 |
| EP | 1 961 744 | 8/2008 |
| JP | 04-342560 | 11/1992 |
| JP | 05-239046 | 9/1993 |
| JP | 08-282117 | 10/1996 |
| JP | 2002-506858 | 3/2002 |
| JP | 2005-519957 | 7/2005 |
| JP | 2005-539023 | 12/2005 |
| JP | 2006-509844 | 3/2006 |
| JP | 2007-523902 | 8/2007 |
| JP | 2007-524685 | 8/2007 |
| JP | 2010-523599 | 7/2010 |
| WO | WO-97/48399 | 12/1997 |
| WO | WO-97/48400 | 12/1997 |
| WO | WO-97/48409 | 12/1997 |
| WO | WO-98/13046 | 4/1998 |
| WO | WO-98/45256 | 10/1998 |
| WO | WO-98/45257 | 10/1998 |
| WO | WO-99/33847 | 7/1999 |
| WO | WO-99/47507 | 9/1999 |
| WO | WO-00/64911 | 11/2000 |
| WO | WO-01/01974 | 1/2001 |
| WO | WO-02/22627 | 3/2002 |
| WO | WO-03/013617 | 2/2003 |
| WO | WO-03/060523 | 7/2003 |
| WO | WO-03/077727 | 9/2003 |
| WO | WO-2004/014352 | 2/2004 |
| WO | WO-2004/048544 | 6/2004 |
| WO | WO-2005/056526 | 6/2005 |
| WO | WO-2005/079865 | 9/2005 |
| WO | WO-2006/032911 | 3/2006 |
| WO | WO-2006/080993 | 8/2006 |
| WO | WO-2006/093991 | 9/2006 |
| WO | WO-2006/116736 | 11/2006 |
| WO | WO-2007/008848 | 1/2007 |
| WO | WO-2007/031640 | 3/2007 |
| WO | WO-2007/042504 | 4/2007 |
| WO | WO-2007/090461 | 8/2007 |
| WO | WO-2007/148738 | 12/2007 |
| WO | WO-2008/016006 | 2/2008 |
| WO | WO-2008/028000 | 3/2008 |
| WO | WO-2008/058192 | 5/2008 |
| WO | WO-2008/124703 | 10/2008 |
| WO | WO-2009/076434 | 6/2009 |
| WO | WO-2009/089383 | 7/2009 |
| WO | WO-2010/036814 | A1 | 4/2010 |
| WO | WO-2010/065899 | A2 | 6/2010 |
| WO | WO-2010/065906 | A2 | 6/2010 |

OTHER PUBLICATIONS

Genis et al., Design of a Carbonic Anhydrase IX Active-Site Mimic to Screen Inhibitors for Possible Anti-Cancer Properties, Biochemistry 48(6), pp. 1-20 [pp. 1322-1331], 2009.

International Search Report mailed Mar. 13, 2013 for PCT/US2013/020283 (WO2013/103813).

Alberto et al., "A Novel Organometallic Aqua Complex of Technetium for the Labeling of Biomolecules: Synthesis of [99mTc(OH2)3(CO3]+ from [99mTcO4}—in Aqueous Solution and Its Reaction with a Bifunctional Ligand", Journal of American Chemical Society, American Chemical Society, vol. 120, No. 31, 1998, pp. 7987-7988.

Babich, et al., "Applications of Nuclear Imaging in Drug Discovery and Development," Drug Discovery Dev., 2006, vol. 1, pp. 365-381.

Banerjee et al., "{Re(III)C13} Core Complexes with Bifunctional Single Amino Acid Chelates", Inorganic Chemistry, American Chemical Society, vol. 41, No. 22, 2002, pp. 5795-5802.

Banerjee et al., Bifunctional Single Amino Acid Chelates for Labeling of Biomolecules with the {Tc(CO)3} and {Re(CO)3} Cores. Crystal and Molecular Structures of [ReBr(CO)3(H2NCH2C5H4N)], [Re(CO)3 (C5H4NCH2)2NH} Br, [Re(CO)3 {C5H4NCH2)2NCH2CO2H } Br, [Re(CO)3{X(Y)NCH2CO2CH2CH3}Br(X=Y=2-pyridylmethyl; X=2-pyridylmethyl, Y=2-(1- methylimidazol-ypmethyl,[ReBr(CO)3{C5H4NCH2)Nh(CH2C4H3S)}1, and [Re(CO)3{C5H4NCH2)N(CH2C4H3S)(CH2CO2)}1, Inorganic Chemistry, vol. 41, No. 24, 2002, pp. 6417-6425.

Banerjee et al., "Synthesis and Evaluation of Technetium-99m- and Rhenium-Labeled Inhibitors of the Prostate-Specific Membrane Antigen (PSMA)", Journal of Medicinal Chemistry, vol. 15, pp. 4504-4517, 2008.

Banerjee, A. et al. "Inhibition of matrix metalloproteinase-9 by "multi-prong" surface binding groups", Chem. Commun., 2005, No. 20, pp. 2549-2551.

Benita, S. et al., "Characterization of Drug-Loaded Poly(d,l-lactide) Microspheres," Journal of Pharmaceutical Sciences, vol. 73, No. 12, Dec. 1984, pp. 1721-1724.

Berge, et al., "Pharmaceutical Salts," Journal of Pharmaceutical Sciences, vol. 66, No. 1, Jan. 1977, pp. 1-19.

Berthommier, E., et al., "New preparation of [123I]PE21: investigation of the oxidation and purification steps," J. Label Compd Radiopharm, 2002, vol. 45, No. 12, pp. 1019-1028.

Bonomi et al., "Phosphate Diester and DNA Hydrolysis by a Multivalent, Nanoparticle-Based Catalyst", Journal of the American Chemical Society, vol. 130, 2008, pp. 15744-15745.

Carter et al., "Prostate-Specific Membrane Antigen is a Hydrolase with Substrate and Pharacologic Characteristics of a Neuropeptidase," Proc. Nat. Acad. Sci., USA, 93:749-753, Jan. 1996.

Casini, et al., "Carbonic Anhydrase Inhibitors: Synthesis of Water Soluble Sulfonamides Incorporating a 4-sulfamoylphenylmethylthiourea Scaffold, with Potent Intraocular Pressure Lowering Properties," Journal of Enzyme Inhibition and Medicinal Chemistry, 2002, vol. 17, No. 5, pgs. 333-343.

Cecchi et al., Alessandro, "Carbonic Anhydrase Inhibitors. Design of Fluorescent Sulfonamides as Probes of Tumor-assoicated Carbonic Anhydrase IX that Inhibit Isozyme IX-Mediated Acidification of Hypoxic Tumores," Journal Of Medicinal Cheimistry, vol. 48, No. 15, Jul. 2005, pp. 4834-4841.

Chen et al., "Radiohalogenated Prostate-Specific Membrane Antigen (PSMA)-Based Ureas as Imaging Agents for Prostate Cancer", Journal Of Medicinal Chemistry, vol. 51, 2008, pp. 7933-7943.

Chen, et al., "Age-related decrease in eardiopulomnary andrenergic neuronal function in children as assessed by 1123 metaiodobenzylgucanidine imaging," J. Nucl. Cardiol., 2008, vol. 15, No. 1, pp. 73-79.

Communication—EP Search Report in EP Appln No: 13195617.9 dated Jan. 31, 2014.

Communication pursuant to Article 94(3) EPC in EP Appln No: 09 775 430.3 dated Aug. 8, 2013.

Communication received in EP Appln. No. 09701293.4 dated May 3, 2012.

(56) References Cited

OTHER PUBLICATIONS

Database Beilstein [Online]; Beilstein Institute for Organic Chemistry, 1958, Database Accession No. Citation No. 990210, XP002577062.

Database Caplus, [Online] Nov. 30, 1992, Karube Yoshiharu et al: "Preparation of sulfanilamide derivatives and their technetium complexes as radiodiagnostic agents", XP002577771, retrieved from CAPLUS Database accession No. 1993-427837.

Database WPI, Week 199302, Thomas Scientific, London, GB; AN 1993-014070 & JP4342560 A (Daiichi Radioisotope Kenkyusho) Nov. 30, 1992.

De Leval, et al. "Carbonic Anhydrase Inhibitors: Synthesis and Topical Intraocular Pressure Lowering Effects of Fluorine-Containing Inhibitors Devoid of Enhanced Reactivity", Journal Of Medicinal Chemistry, 2004, vol. 47, No. 11, pp. 2796-2804.

Deasy, Patrick et al., "Microencapsulation and Related Drug Processes", 1984, School of Pharmacy, University of Dublin, Marcel Dekker, Inc. (TOC).

Decision of Rejection dated Feb. 12, 2014, in related Chinese Appln No: 200980107793.4.

Decision of Rejection mailed Sep. 11, 2014, in related Chinese Appln. No. 200980153878.6.

Donovan et al., XP002614474 "Fluorous Isocyanates: Convenient Synthons for the Preparation of Radioiodinated Compounds in High Effective Specific Activity", Journal of Organic Chemistry, vol. 74, Oct. 2, 2009, pp. 8133-8138.

Dubenko, et al. "Thiocarbanilide Derivatives. IV. Synthesis of unsymmetrical monohalothiocarbanilides", Zhurnal Obshchei Khimii, 1962, vol. 32, pp. 626-628.

Dubois, L., et al., "Imaging the hypoxia surrogate marker CA IX requires expression and catalytic activity for binding fluorescent sulfonamide inhibitors," 2007, Radiotherapy and Oncology, vol. 83, pp. 367-373.

EPA, Commonly Encountered Radionuclides, 2011, 2 pages.

European Search Report in Application No. 07844938.6 mailed Jun. 13, 2012.

Examination Report mailed Aug. 28, 2014 in Australia Application No. 2009322164.

Examination Report mailed Jul. 22, 2014 in Australia Application No. 2009322171.

Examination Report mailed Jul. 29, 2014 in Australia Application No. 2009322167.

Feng et al., "Comparing a mononuclear Zn(II)complex with hydrogen bond donors with a dinuclear Zn(II) complex for catalysing phosphate ester cleavage", Chem. Commun., 2006, pp. 1845-1847.

Final Office Action received for U.S. Appl. No. 12/631,312 dated Sep. 6, 2012.

First Examination Report in AU Appln No. 2010260195 issued Jul. 30, 2014.

Flux, et al., "Absorbed Dose Ratios for Repeated Therapy of Neuroblastoma with I-131 mIBG," Cancer Biother., Radiopharm., 2003, vol. 18, No. 1, pp. 81-87.

Foss et al., "Radiolabeled Small-Molecule Ligands for Prostate-Specific Membrane Antigen: In Vivo Imaging in Experimental Models of Prostate Cancer," Clin. Cancer Res., 11(11):4022-4028 (2005).

Fullerton, et al., "Comparison of Radiohaloanalogues of Meta-Iodobenzylguanidine (MIBG) for a Combined Gene-and Targeted Radiotherapy Approach to Bladder Carcinoma," Med. Chem., 2005, vol. 1, pp. 611-618.

Gallagher, J. et al. "Protease Activity of I, 10-Phenanthroline-Copper(I). Targeted Scission of the Catalytic Site of Carbonic Anhydrase", Biochemistry, 1998, vol. 37, pp. 2096-2104.

Gasparini et al., "(R,S)-4-Phosphononphenylglycine, a Potent and Selective Group III Metabotropic Glutamate Receptor Agonist, is Anticonvulsive and Neuroprotective in Vivo," J. Pharm. Exper. Ther., 290(3):1678-1687 (1999).

Gents et al., Design of a Carbonic Anhydrase IX Active-Site Mimic to Screen Inhibitors for Possible Anti-Cancer Properties, Biochemistry 48(6), pp. 1-20 [pp1322-1331], 2009.

Gracheva, et al. "Chemical changes during beta-decay of bismuth-210 (RaE) entering into the composition of tris(p-sulfamoylphenyl)bismuth", STN on the Web, File CAPLUS, 1968, vol. 83, p. 305.

Greene, T. W. et al., "Protection for the Hydroxyl Group, Including 1,2- and 1,3-Diols," Protective Groups in Organic Synthesis, Third Edition, 1999, pp. 113-148.

Greene, T. W. et al., Protective Groups in Organic Synthesis, Second Edition, Wiley, New York, 1991.

Gregoriadis, G., et al., Drug Carriers in Biology and Medicine, Chapter 14: Liposomes, 1979, Academic Press, pp. 287-341.

Hanada et al., "Preparation of 2,8-dia7aspiro[4.5]decane containing bis(imidazol-2-ylmethyl_amines as CXCR4 antagonists for treatment of inflammation and immune disease", caplus an 2008:159048, 5 pages.

Hayakawa et al., XP-002614476 "Second-Generation Total Synthesis of Haterumalide NA Using B-Alkyl Suzuki-Miyaura Coupling", Organic Letters, vol. 10, No. 9, 2008, pp. 1859-1862.

Henson et al., "Resonance Raman Investigation of Equatorial Ligand Donor Effects on the $Cu_2O_22$ Core in End-On and Side-On u-Perozo-Dicopper(II) and Bis-u-oxo-Dicopper(III) Complexes", Journal of American Chemical Society, vol. 125, 2003, pp. 5186-5192.

International Preliminary Examination Report and Written Opinion mailed Jul. 17, 2014 in Intl Appln. No. PCT/US2013/020283.

International Search Report—PCT/US2013/020283—WO2013/103813, Mar. 13, 2013.

International Search Report and Written Opinion in PCT/US2009/030487 dated Jun. 26, 2009.

International Search Report and Written Opinion in PCT/US2009/066836 dated Dec. 28, 2010.

International Search Report and Written Opinion in PCT/US2009/066832 dated Oct. 14, 2010.

International Search Report and Written Opinion mailed Mar. 30, 2011 in International Applicaton No. PCT/US2009/066842.

International Search Report in International Application No. PCT/US00/11262, mailed Sep. 12, 2000.

International Search Report in International Application No. PCT/US07/83934, mailed Mar. 13, 2008.

Izdebski et al., "Synthesis of N,N'-Carbonyl-bis-amino Acids and N,N'-Carbonyl-bis-peptides," Polish J. Chem., 71(8):1066-1074, 1997.

Jackson et al., "Design, Synthesis, and Biological Activity of a Potent Inhibitor of the Neuropeptidase N-Acetylated alpha-Linked Acidic Dipeptidase," J. Med. Chem., 39(2):6l9-622, 1996.

Jalil, R. et al., "Biodegradable poly(lactic acid) and poly(lactide-co-glycolide) microcapsules: problems associated with preparative techniques and release properties", J. Microencapsulation, 1990, vol. 7, No. 3, pp. 297-325.

K.P.Maresca et al. A series of Halogenated heterodimeric Inhibitors of Prostate Specific Membrane Antigen (PSMA) as Radiolabeled Probes for Targeting Prostate Cancer, J. Med. Chem. 2009, 52, 347-357.

Kojima et al., "Synthesis and Characterization of Mononuclear Ruthenium (III) Pyridylamine Complexes and Mechanistic Insights into Their Catalytic Alkane Functionalization with m-Chloroperbenzoic Acid", Chemistry, vol. 13, 2007, pp. 8212-8222.

Kozikowski et al., "Design of Remarkably Simple, Yet Potent Urea-Based Inhibitors of Glutamate Carboxypeptidase II (NAALADase)," J. Med. Chem. 44(3):298-301, 2001.

Kozikowski et al., "Synthesis of Urea-Based Inhibitors as Active Site Probes of Glutamate Carboxypeptidase II: Efficacy as Analgesic Agents," J. Med. Chem., 47:1729-1738 (2004).

Krebs, H.A., "Inhibition of Carbonic Anhydrase by Sulphonamides," the Biochemical Journal, vol. 43, 1948, pp. 525-528.

Kularatne, S.A. et al., "Design, Synthesis, and Preclinical Evaluation of Prostate-Specific Membrane Antigen Targeted 99mTc-Radioimaging Agents," Molecular Pharmaceutics, 2009, vol. 6, No. 3, pp. 790-800.

Kusumi et al., "Preparation of heterocycle compounds having (un)protected acidic group as CXCR4 antagonists", caplus an 2007:1332283, 8 pages.

(56) References Cited

OTHER PUBLICATIONS

Lewis et al., "Maleimidocysteineamido-DOTA Derivatives: New Reagents for Radiometal Chelate Conjugation to Antibody Sulfhydryl Groups Undergo pH-Dependent Cleavage Reactions", Bioconjugate Chemistry, American Chemical Society, vol. 9, No. 1, 1998, pp. 72-86.
Lewis, Hawley'S Condensed Chemical Dictionary, 12 Ed., Van Nostrand Reinhold Co., New York, NY, pp. 9, 420, 421, and 881, 1993.
Lim, et al. "Microencapsulation of Living Cells and Tissues," Journal of Pharmaceutical Sciences, Apr. 1981, vol. 70, No. 4, pp. 351-354.
Liu et al., Preparation and Properties of 99mTc(Co)3—Labeled N,N-Bis(2-pyridylmethyl)-4-aminobutyric Acid, Bioconjug Chem 15(6), pp. 1-14 [pp. 1441-1446], 2004.
Maresca, et al. "A series of halogenated Heterodimeric inhibitors of prostate specific membrane antigen (PSMA) as radiolabeled probes for targeting prostate cancer", Journal Of Medicinal Chemistry, American Chemical Society, US, vol. 52, Jan. 22, 2009, pp. 347-357, XP002614472.
Mathiowitz, E. et al., "Morphology of Polyanhydride Miscrosphere Delivery Systems," Scanning Microscopy, 1990, vol. 4, No. 2, pp. 329-340.
Mathiowitz, E. et al., "Polyanhydride Microspheres as Drug Carriers. II. Microencapsulation by Solvent Removal," Journal of Applied Polymer Science, 1988, vol. 35, pp. 755-774.
McIntee, et al., "A Convenient Method for the Preparation of Fluorous Tin Derivatives for the Fluorous Labeling Strategy" J. Org. Chem., 2008, vol. 73, pp. 8236-8243.
Nakano, M. et al., "Sustained Urinary Excretion of Sulfamethizole Following Oral Administration of Enteric Coated Microcapsules in Humans," International Journal of Pharmaceutics, 1980, vol. 4, pp. 291-298.
Nan et al., "Dual Function Glutamate-Related Ligands: Discovery of a Novel, Potent Inhibitor of Glutamate Carboxypeptidase II Possessing mGluR3 Agonist Activity," J. Med. Chem., 43(5):772-774, 2000.
Nonat et al., "Structure, Stability, Dynamics, High-Field Relaxivity and Ternary-Complex Formation of a New Tris(aquo) Gadolinium Complex", Chemistry, vol. 13, 2007, pp. 8489-8506.
Non-Final Office Action in U.S. Appl. No. 12/631,312 dated Dec. 27, 2012.
Non-final Office Action received for U.S. Appl. No. 12/631,312 dated Mar. 6, 2012.
Notice of Allowance received for U.S. Appl. No. 12/631,337 dated Mar. 15, 2012.
Notice of Allowance received for U.S. Appl. No. 12/631,343 dated Mar. 12, 2012.
Notice of Reasons for Rejection in JP Appln No. JP 2011-539752 dated Mar. 25, 2014.
Office Action—Final—Reasons for Rejection in JP Appln No. 2010-542351 dated Apr. 1, 2014.
Office Action cited in U.S. Appl. No. 12/029,367 mailed Oct. 19, 2010.
Office Action for JP 2011-539755, mailed Oct. 30, 2012.
Office Action for JP 2011-539755, mailed Oct. 30, 2012—English Translation.
Office Action in CN Appln No. 200980153722.8 dated Oct. 30, 2012.
Office Action in CN Appln No. 200980153877.1 dated Apr. 8, 2014.
Office Action in CN Appln No. 200980153877.1 dated Sep. 17, 2013.
Office Action in CN Appln No. 200980153878.6 dated Jan. 14, 2013.
Office Action in CN Appln No. 200980153878.6 dated Mar. 7, 2014.
Office Action in CN Appln. No: 200980153877.1 dated Oct. 30, 2012.
Office Action in EP Appln No. 09 701 293.4 dated Dec. 20, 2012.
Office Action in Japan Application No. 2011-539757 mailed Jun. 17, 2014.
Office Action in JP Appln No. 2010-542351 dated Aug. 20, 2013.
Office Action in JP Appln No. 2011-539757 dated Dec. 24, 2013.
Office Action in RU Appln No. 2011127467 dated Apr. 20, 2013.
Office Action in RU Appln No. 2011127468 dated Jul. 17, 2013.
Office Action mailed Sep. 2, 2014 in Japan Application No. 2010-542351 (Translation).
Official Action RU Appln No: 2011127462, dated May 22, 2013.
Pastorekov, S., et al., "Carbonic anhydrase IX (CA IX) as potential target for cancer therapy," 2004, Cancer Therapy, vol. 2. (19 pages).
Rami, M. et al. "Carbonic Anhydrase Inhibitors: Design of Membrane-Impermeant Copper(II) Complexes of DTPA-, DOTA-, and TETA-Tailed Sulfonamides Targeting the Tumor-Associated Transmembrane Isoform IX", Chemmedchem, 2008, vol. 3, pp. 1780-1788.
Remington'S: the Science and Practice of Pharmacy, 17th Edition, pp. 1795, 1985.
Restriction Requirement received for U.S. Appl. No. 12/350,894 dated Jun. 10, 2011.
Roy, B. et al., "Two-Prong Inhibitors for Human Carbonic Anhydrase II", Journal of American Chemical Society, vol. 126, 2004, pp. 13206-13207.
Saitou et al., "Preparation of N-arylmethyl or N-hererocyclylmethyl-N-(imidazol-2-ymethyl)amines as antagonists of chemokine receptor CXCR4", caplus an 2005:1004718, 6 pages.
Salib, N. et al., "Utilization of Sodium Alginate in Drug Microencapsulation," Pharm. Ind., vol. 40, No. 11a, 1978, pp. 1230-1234.
Sawhney, a. et al., "Bioerodible Hydrogels Based on Photopolymerized Poly(ethylene glycol)-co-poly(ahydroxy acid) Diacrylate Macromers," Macromolucules, vol. 26, 1993, pp. 581-587.
Second Office Action in CN Appln No. 200980107793.4 dated Feb. 5, 2013.
Sempuku, K., "Sulfur Compounds," 6001 Chemical Abstracts, Columbus Ohio, US, 101(27). XP 002196919, 1984.
Shah, et al. "Benzylthioureas, Part III", Journal Of Indian Chemical Society, 1959, vol. 36, No. 7, pp. 507-508.
Singh, et al. "The Enzyme-Inhibitor Approach to Cell-Selective Labelling-II. In Vivo Studies with plBS in Small Animals and Man", Applied Radiation and Isotopes, 1991, vol. 42, No. 3, pp. 261-267.
Slusher, et al., "Immunocytochemical Localization of the N-Acetyl-Aspartyl-Glutamate (Naag) Hydrolyzing Enzyme N-Acetylated alpha-Linked Acidic Dipeptidase (NAALADase)," J. Compar. Neurol., 315(2):217-229, 1992.
Slusher, et al., "Rat Brain N-Acetylated alpha-Linked Acidic Dipeptidase Activity," J. Biolog. Chem., 265(34):21297-21301, 1990.
Steffens MG, et al., Targeting of renal cell carcinoma with iodine-131-labeled chimeric monoclonal antibody G250, 1997, J. Clin. Oncol., 15(4) 1529-37 (1 page abstract).
Thallaj, et al. "A Ferrous Center as Reaction Site for Hydration of a Nitrile Group into a Carboxamide in Mild Conditions", Journal of American Chemical Society, vol. 130, 2007, pp. 2414-2415.
Thiry et al., "Targeting Tumor-Associated Carbonic Anhydrase IX in Cancer Therapy," Trends in Pharmacological Sciences, vol. 27, No. 11, Nov. 2006, pp. 566-573.
Thiry, et al. "Indanesulfonamides as Carbonic Anhydrase Inhibitors. Toward Structure-Based Design of Selective Inhibitors of the Tumor-Associated Isozyme CA IX", Journal of Medicinial Chemistry, 2006, vol. 49, No. 9, pp. 2743-2749.
Uddin et al., XP-002614475 "Synthesis and evaluation of [123I]-indomethacin derivatives as Cox-2 targeted imaging agents", Journal of Labelled Compounds and Radiopharmaceuticals, vol. 52, No. 2, May 2009, pp. 387-393.
US Notice of Allowance on DTD Jun. 25, 2014.
US Notice of Allowance on DTD Jun. 19, 2013.
US Notice of Allowance on DTD May 1, 2014.
US Notice of Allowance on DTD Oct. 17, 2014.
US Notice of Allowance on DTD Feb. 11, 2013.
US Notice of Allowance on DTD Dec. 9, 2014.
US Notice of Allowance on DTD May 16, 2014.
US Notice of Allowance on DTD Sep. 8, 2011.
US Notice of Allowance on DTD Feb. 27, 2013.
US Notice of Allowance on DTD Sep. 16, 2014.
US Notice of Allowance on DTD Aug. 15, 2012.

(56) References Cited

OTHER PUBLICATIONS

Viswanathan, et al. "Metanilamide-Substituted Thiourea Derivatives", Current Science, 1952, No. 12, pp. 342-343.

Yao, Zhen et al., Synthesis of Porphyrins Bearing 1-4 hydroxymethyl Groups and other One-carbon oxygenic Substituents in Distinct Patterns, Tetrahedron, vol. 63, 2007, pp. 10657-10670.

"Amino Acid," Wikipedia, 2015, https://en.wikipedia.org/wiki/Amino_acid.

"Definition of Radical", Google, 2015, https://www.google.com/search?q=definitionofradical&sourceid=ie7&rls=com.microsoftenus:IEAddress&ie=&oe=&gws_rd=ssl.

Dischino et al., "Synthesis of nonionic gadolinium chelates useful as contrast agents for magnetic resonance imaging: 1,4,7,-tris (carboxymethyl) -10-substituted-1,4,7,10-tetraazacyclododecanes and their corresponding gadolinium chelates," Inorganic Chemistry, 1991, vol. 30, No. 6, pp. 1265-1269, Caplus an 1991:177144.

Non-Final Office Action issued in U.S. Appl. No. 14/610,417 mailed Jun. 26, 2015.

* cited by examiner

⁹⁹ᵐTc-5 BioD in HEK-293/CAIX Xenograft Mice
(Block is 10mg/kg Acetazolamide)

⁹⁹ᵐTc-9 BioD in HEK-293/CAIX Xenograft Mice
(Block is 10mg/kg Acetazolamide)

METAL COMPLEXES OF POLY(CARBOXYL)AMINE-CONTAINING LIGANDS HAVING AN AFFINITY FOR CARBONIC ANHYDRASE IX

CROSS-REFERENCE TO RELATED PATENT APPLICATIONS

This application claims the benefit of the priority date of U.S. Provisional Application No. 61/584,146, filed Jan. 6, 2012, the complete disclosure of which is incorporated herein by reference in its entirety.

BACKGROUND OF THE INVENTION

The present technology relates generally to the field of radiopharmaceuticals and their use in nuclear medicine for the treatment of various disease states. It is well known that tumors may express unique proteins associated with their malignant phenotype or may over-express normal constituent proteins as compared to the expression of these proteins in normal cells. The expression of distinct proteins on the surface of tumor cells offers the opportunity to diagnose, characterize ad treat disease conditions by using radiopharmaceutical compounds that selectively bind to specific tumor cell surface proteins. In particular, the present inventors have found that radiolabeled ligands that specifically bind to the CA-IX isoform of the enzyme carbonic anhydrase, often over-expressed on many cancer cells provides an attractive route for non-invasive and selective treatment of cancers.

While CA-IX is a membrane-anchored, its catalytic domain resides in the extracellular space. It has a limited tissue distribution and is found at low levels primarily in the gastrointestinal tract. The expression of CA-IX is under the control of HIF-1α, and this isozyme is highly expressed in tumors cells exposed to hypoxia both in vitro and in vivo. Increased CA-IX expression has been detected in carcinomas of the cervix, ovary, kidney, esophagus, lung, breast, and brain. It has been hypothesized that the low extracellular pH as a result of the activity of CA-IX leads to tumorigenic transformation, chromosomal rearrangements, extracellular matrix breakdown, migration and invasion, induction of growth factors, protease activation, and chemoresistance. Accordingly, a correlation can be made between the cellular levels of CA-IX and tumor progression. Radiopharmaceuticals directed to the CA-IX protein thus provide an novel avenue for the non-invasive treatment of cancer.

The selective targeting of cancer cells with radiopharmaceuticals is challenging. A variety of radionuclides are known to be useful for radioimaging and radiotherapy, including Re-186, Re-188, Tc-99m, Ga-67, In-111, I-123, and I-131. The present invention provides bifunctional molecules that comprise a specific receptor honing bioactive molecule covalently tethered to Pt, $^{64}$Cu, $^{186}$Re, $^{188}$Re, or $^{99m}$Tc as tumor-selective imaging agents.

SUMMARY OF THE INVENTION

The present invention is directed to certain poly(carboxyl)amine-containing ligands described herein and their metal complexes. In particular, the poly(carboxyl)amine-containing ligands conform to compounds according to Formula I, or a pharmaceutically acceptable salt, tautomer, or ester thereof.

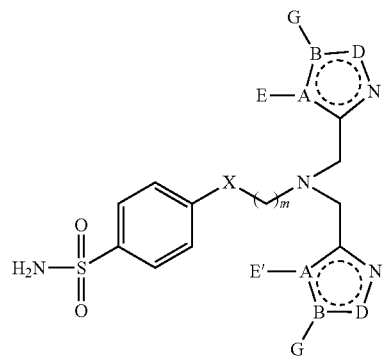

X in Formula I is selected from the group consisting of —$(CH_2)_n$—, —$(CH_2)$—O—, —$(CH_2)_n$—$N(R_g)$—, —$(CH_2)_n$—$N(R_g)$—C(O)— and —O—. Substituent $R_g$ is hydrogen or ($C_1$-$C_6$)alkyl, while A, B and D are each independently —(CH)—, or —N—.

In Formula I, E is —$(CH_2)$—Z-Q, E' is —$(CH_2)$—Z-Q' and Z is —$(CH_2)_p$—, or —C(O)—. Group Q is selected from the group consisting of —H, —$OR_g$, and $NR_aR_b$ while Q' is selected from the group consisting of —H, —$OR_g$, and $NR_aR_e$.

Substituent groups $R_a$, $R_b$ $R_d$ and $R_e$ are each independently hydrogen, ($C_1$-$C_6$)alkyl, or carboxy($C_1$-$C_6$)alkylene. G is —$(CH(R_m))_n$—$R_h$—, or —$(CH_2)_p$—C(O)—$R_h$, and $R_h$ is selected from the group consisting of —H, —OH, $NR_aR_b$ and —$CO_2H$.

$R_m$ in Formula I compounds is selected from the group consisting of —H, —COOH and —COO($C_1$-$C_6$)alkyl while subscripts m, n and p independently are integers between 0 to 10 inclusive.

⌬ in Formula I provides for aromatic and non-aromatic ring systems by providing the option of having one or more double bonds. In Formula I, any alkyl or carboxyalkyl is optionally substituted with one or more members selected from the group consisting of hydrogen, carboxy($C_1$-$C_6$)alkylene, hydroxy($C_1$-$C_6$)alkylene and amino($C_1$-$C_6$)alkylene;

In some embodiments, substituent groups $R_a$ and $R_b$ are each independently

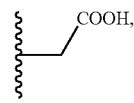 [SMILES: *CC(=O)O]

$R_d$ is hydrogen and substituent group $R_e$ is

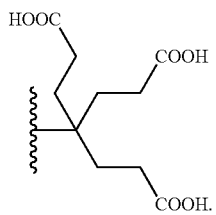 [SMILES: *C(CCC(=O)O)(CCC(=O)O)CCC(=O)O]

For certain compounds according to Formula I $R_a$ and $R_d$ are each independently hydrogen, and $R_b$ and $R_e$ ($C_1$-$C_6$)alkyl, for example, an alkyl group that is further substituted with carboxyalkylene groups. Exemplary of such a Formula I compound is one in which $R_a$ and $R_d$ are each independently hydrogen, and $R_b$ and $R_e$ are

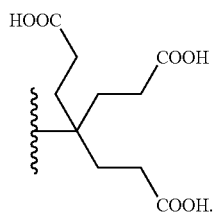

The present invention also provides according to an embodiment a metal complex according to Formula II:

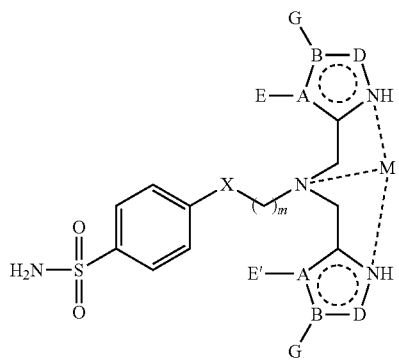

The complex of Formula II comprises a Formula I compound, or a pharmaceutically acceptable salt, tautomer, or ester thereof and a metal (M) selected from the group consisting of Pt, Zn, $^{64}$Cu, $^{186}$Re, $^{188}$Re and $^{99m}$Tc.

In one embodiment, the metal is $^{99m}$Tc, $^{186}$Re, or $^{188}$Re.

According to another embodiment, the invention provides a metal complex in which the ratio of the sum of percent injected dose per gram tissue (% ID/g) values for liver and kidney tissues to the % ID/g value for tumor tissue decreases when observed at a first time point, which is one hour post-administration of the metal complex to CA9/293 xenograft mice, and at a second time point, which is four hours post-administration of the metal complex to CA9/293 xenograft mice. The observed decrease in ratio is in the range from a factor of about 2 to a factor of about 4.

The present invention also provides a pharmaceutical composition comprising at least one metal complex of a compound of Formula I, or a pharmaceutically acceptable salt, tautomer, or ester thereof; and a pharmaceutically acceptable carrier.

According to another embodiment is provided a method for imaging a patient suspected of harboring CA IX expressing tumor tissue, comprising (a) administering to a patient suspected of harboring CA LX expressing tumor tissue a diagnostically effective amount of a radionuclide metal complex of a compound of Formula I, or a pharmaceutically acceptable salt, tautomer, or ester thereof and (b) obtaining an image of the patient, including any CA IX expressing tumor tissue, if any.

In yet another embodiment, is provided a kit for the preparation of an agent targeting CA IX expressing tumor tissue comprising a compound according to Formula I. The invention further provides a method for preparing a metal complex for targeting CA IX expressing tumor tissue in a subject by contacting a metal-containing precursor, comprising a metal selected from the group consisting of Pt, Zn, $^{64}$Cu, $^{186}$Re, $^{188}$Re and $^{99m}$Tc, with an excess of free, uncomplexed compound of Formula I to provide a mixture comprising: (i) free, uncomplexed compound of Formula I, and (ii) a metal complex thereof. According to the inventive method administration of the mixture to a subject suspected of harboring CA IX expressing tumor tissue is done without taking any steps to separate free, uncomplexed compound of Formula I from its metal complex.

In one embodiment is provided a poly(carboxyl)amine-containing ligand whose tricarbonyl metal complex, under conditions of a CA IX competitive binding assay (hypoxic HeLa cells), yields an $IC_{50}$ value (nM), which is lower than that observed under the same assay conditions for the free, uncomplexed ligand by a factor ranging from about 2 to about 200. In some embodiments, the $IC_{50}$ value of the tricarbonyl metal complex is lower than that observed under the same assay conditions for the free, uncomplexed ligand by a factor of at least 10, by a factor of at least 20, by a factor of at least 30, by a factor of at least 50, by a factor of at least 100, by a factor of at least 150, or by a factor of at least 200.

BRIEF DESCRIPTION OF THE DRAWINGS

FIGS. 5 and 6 illustrate tissue biodistribution and bioclearance data for various non-tumor and CA IX expressing tumor tissues. Representative CA IX technitium-99m complexes used in these studies have an oxybutylene linker connecting the chelator to the sulfonamide moiety.

DETAILED DESCRIPTION OF THE PREFERRED EMBODIMENTS

Definitions

Figure 1:
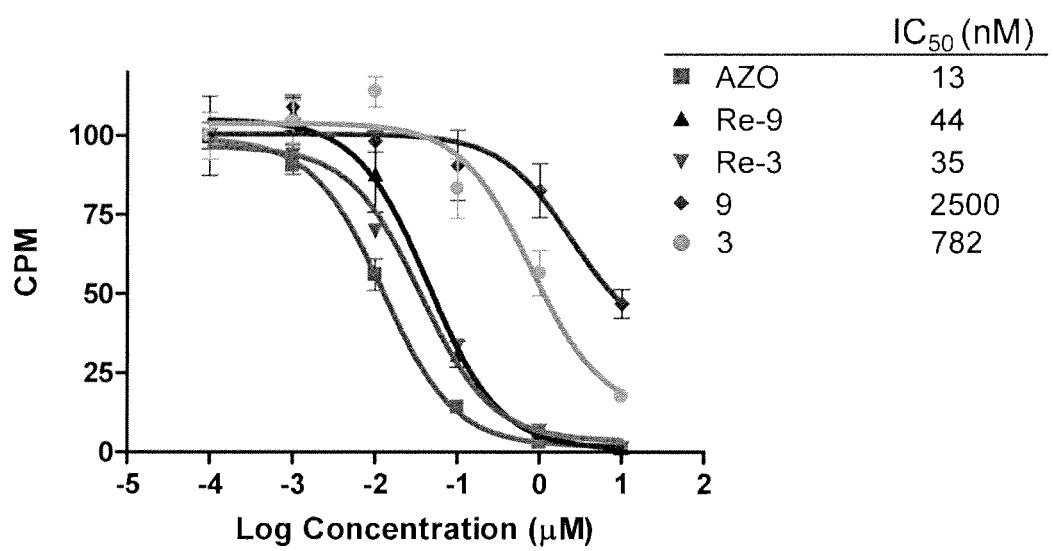
FIG. 1 illustrates CA IX competitive binding curves for representative compounds and complexes according to Formulae I and II respectively.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context.

Alkyl groups include straight chain and branched chain alkyl groups having from 1 to 20 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Alkyl groups may be substituted or unsubstituted. Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "hydroxyalkyl," refers to an alkyl group having the indicated number of carbon atoms wherein one or more of the alkyl group's hydrogen atoms is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof.

The term "aminoalkyl," refers to an alkyl group having the indicated number of carbon atoms wherein one or more of the alkyl group's hydrogen atoms is replaced with an NR$^1$R$^2$ group, wherein R$^1$ and R$^2$ each independently refer to hydrogen, unsubstituted (C$_1$-C$_8$)alkyl, unsubstituted aryl and aryl substituted with one to three substituents selected from -halo, unsubstituted alkoxy, thiol and CN. When R$^1$ and R$^2$ are attached to the same nitrogen atom, they can be combined with the nitrogen atom to form a 5-, 6- or 7-membered ring. Non-limiting examplars of aminoalkyl groups include, but are not limited to, —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$CH$_2$CH$_2$CH$_2$NH$_2$, —CH$_2$CH$_2$CH$_2$CH$_2$CH$_2$CH$_2$NH$_2$, and branched versions thereof.

The term "alkylcarbonyl" denotes an (C$_1$-C$_8$)alkyl-C(O) group in which one or more hydrogen atoms in the C$_1$-C$_8$ alkyl group is replaced with a C(O) group. Representative examples include, but are not limited to, acetyl, propionyl, and CH$_3$(CH$_2$)$_2$C(O)— group.

The term "carboxyalkylene" denotes a divalent (C$_1$-C$_8$) alkyl group in which one or more hydrogen atoms in the C$_1$-C$_8$ alkyl group is replaced with a C(O)$_2$H group. Representative examples include, but are not limited to, —(CH$_2$) COOH, or a —CH$_2$(CH$_2$)$_2$C(O)— group.

Each of the terms "halogen," "halide," and "halo" refers to —F, —Cl, —Br, or —I.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indenyl, pentalenyl, and naphthyl groups. In some embodiments, aryl groups contain 6-14 carbons, and in others from 6 to 12 or even 6-10 carbon atoms in the ring portions of the groups. Aryl group includes both substituted and unsubstituted aryl groups. Substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Heteroaryl groups are monocyclic aromatic ring compounds containing 5 or more ring members, or bicyclic aromatic ring compounds containing 6 or more ring members, of which, one or more is a heteroatom such as, but not limited to, N, O, and S. Heteroaryl groups may be substituted or unsubstituted. Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl (pyrrolopyridyl), indazolyl, benzimidazolyl, imidazopyridyl (azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups.

The term "heteroatom" refers to an atom of any element other than carbon or hydrogen. Illustrative heteroatoms include nitrogen, oxygen, sulfur and phosphorous.

The term "amine or amino" refers to an NR$_a$R$_b$ group wherein R$_a$ and R$_b$ each independently refer to a hydrogen, (C$_1$-C$_8$)alkyl, aryl and heteroaryl group. Additionally, R$_a$ and R$_b$ together with the same nitrogen atom to which they are attached can form a 5-, 6- or 7-membered ring. For example, —NR$_a$R$_b$ is meant to include 1-pyrrolidinyl, pyridinyl or a 4-morpholinyl ring.

The terms "amide" or "amido" are used interchangeably and are art recognized as an amino-substituted carbonyl and includes a moiety that may be represented by the general formula, —C(O)NR$_a$R$_b$ group wherein R$_a$ and R$_b$ are as defined above.

The term "ligand" refers to a species that interacts in some fashion with another species. In one example, a ligand may be a Lewis base that is capable of forming a coordinate bond with a Lewis Acid. In other examples, a ligand is a species, often organic, that forms a coordinate bond with a metal ion. Ligands, when coordinated to a metal ion, may have a variety of binding modes know to those of skill in the art, which include, for example, terminal (i.e., bound to a single metal ion) and bridging (i.e., one atom of the Lewis base bound to more than one metal ion).

The term "chelating agent" refers to a molecule, often an organic one, and often a Lewis base, having two or more unshared electron pairs available for donation to a metal ion. The metal ion is usually coordinated by two or more electron pairs to the chelating agent. The terms, "bidentate chelating agent", "tridentate chelating agent", and "tetradentate chelating agent" are art-recognized and refer to chelating agents having, respectively, two, three, and four electron pairs readily available for simultaneous donation to a metal ion coordinated by the chelating agent. Usually, the electron pairs of a chelating agent forms coordinate bonds with a single metal ion; however, in certain examples, a chelating agent may form coordinate bonds with more than one metal ion, with a variety of binding modes being possible.

The term "coordination" refers to an interaction in which one multi-electron pair donor coordinatively bonds (is "coordinated") to one metal ion.

The term "complex" refers to a compound formed by the union of one or more electron-rich and electron-poor molecules or atoms capable of independent existence with one or more electronically poor molecules or atoms, each of which is also capable of independent existence.

The phrase "poly(carboxyl)amine" refers to chemical group that can co-ordinate transition metals. The poly(carboxyl)amine comprises a phenylsulfonamide group that provides binding selectivity to CA IX and which is conjugated via a linker to a metal chelatig group. The metal chelating group usually contains from about 1 to about 10 carboxyl or carboxy(C$_1$-C$_6$)alkylene groups as further defined herein. Exemplary of metal chelating groups include the following:

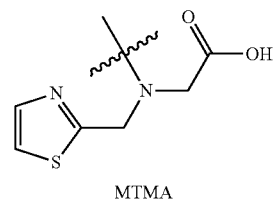

MTMA

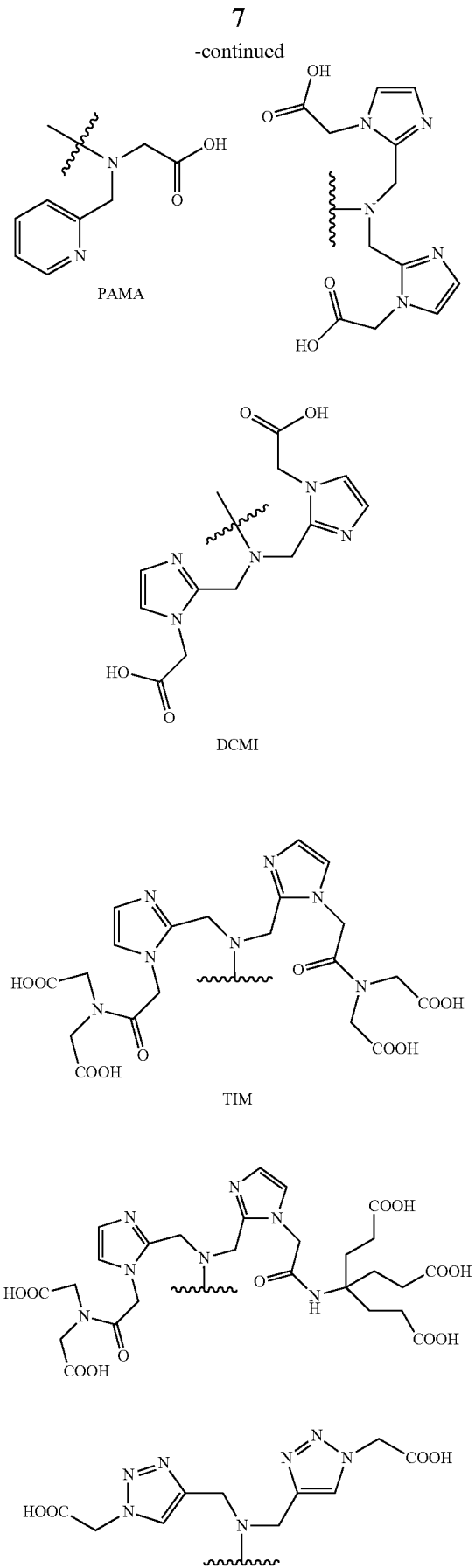
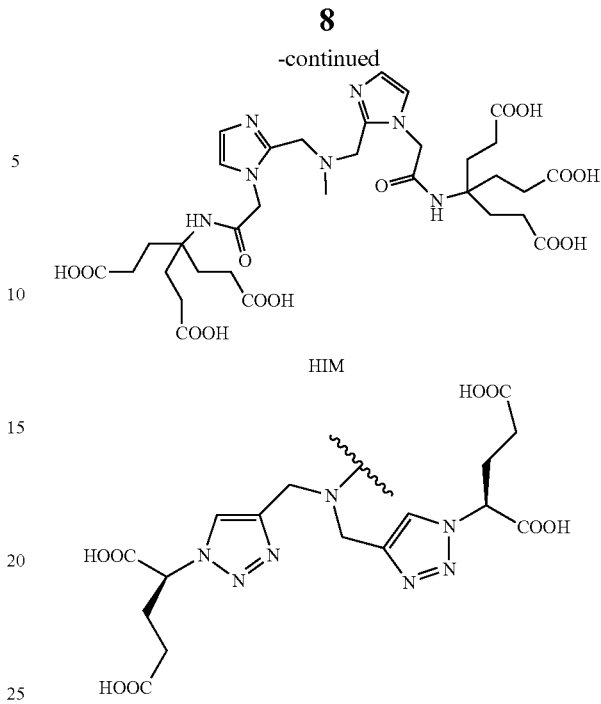

The phrase "therapeutically-effective amount" as used herein means that amount of a compound, material, or composition comprising a compound which is effective for producing some desired therapeutic effect in at least a sub-population of cells in an animal at a reasonable benefit/risk ratio applicable to any medical treatment.

As used herein, the terms "treating" or "treatment" is intended to encompass also diagnosis, prophylaxis, therapy and cure. The patient receiving this treatment is any animal in need, including primates, in particular humans, and other mammals such as equines, cattle, swine and sheep; and poultry and pets in general.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 3$^{rd}$ ed.; Wiley: New York, 1999).

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given that structure, then the depicted structure controls. Additionally, if the stereochemistry of a structure or a portion of a structure is not indicated with, for example, bold or dashed lines, the structure or portion of the structure is to be interpreted as encompassing all stereoisomers of it.

A "patient" or subject" includes an animal, such as a human, cow, horse, sheep, lamb, pig, chicken, turkey, quail, cat, dog, mouse, rat, rabbit or guinea pig. The animal can be a mammal such as a non-primate and a primate (e.g., monkey and human). In one embodiment, a patient is a human, such as a human infant, child, adolescent or adult.

Compounds and their Metal Complexes

The present invention relates to poly(carboxyl)amine-containing ligands and their metal complexes, including radionuclide and non-radionuclide metal complexes, as well as to methods for their synthesis and the use of the inventive complexes in diagnoistic and therapeutic methods, including the radioimaging of tumor tissue, which expresses CA IX, and chemotherapy. More specifically, the present invention relates to a poly(carboxyl)amine-containing compound/ligand according to Formula I, or a pharmaceutically acceptable salt, tautomer, or prodrug thereof

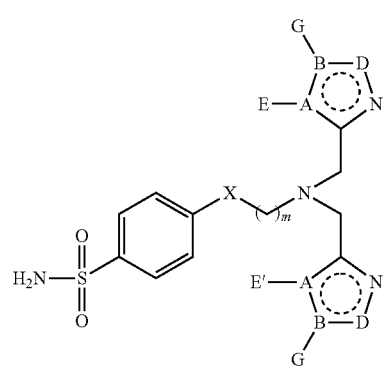

I

For Formula I compounds, X is selected from the group consisting of —(CH$_2$)$_n$—, —(CH$_2$)$_n$—O—, —(CH$_2$)—N(R$_g$)—, —(CH$_2$)$_n$—N(R$_g$)—C(O)— and —O—, each R$_g$ is hydrogen or (C$_1$-C$_6$)alkyl and groups A, B and D are each independently —(CH)—, or —N—.

Substituent E is —(CH$_2$)—Z-Q, while E' is —(CH$_2$)—Z-Q'. Group Z is —(CH$_2$)$_p$—, or —C(O)—. In Formula I, Q is selected from —H, —OR$_g$, or NR$_a$R$_b$ and Q' is selected from —H, —OR$_g$, or NR$_d$R$_e$. Substituent groups R$_a$, R$_b$ R$_d$ and R$_e$ each are independently hydrogen, (C$_1$-C$_6$)alkyl, or carboxy (C$_1$-C$_6$)alkylene, while substituent G is —(CH(R$_m$)$_n$—R$_h$—, or —(CH$_2$)$_p$—C(O)—R$_h$.

Group R$_h$ in Formula I is —H, —OH, NR$_a$R$_b$, or —CO$_2$H, while R$_m$ is —H, —COOH, —COO(C$_1$-C$_6$)alkyl. Subscripts m, n and p independently are integers between 0 to 10 inclusive and Formula I provides for aromatic or non-aromatic compounds by representing the option of having one or more double bonds using the symbol

In Formula I any alkyl, heteroaryl, amine, or carboxyalkyl can be optionally substituted with one or more members selected from the group consisting of hydrogen, carboxy(C$_1$-C$_6$)alkylene, hydroxy(C$_1$-C$_6$)alkylene and amino(C$_1$-C$_6$)alkylene.

In some embodiments, substituent groups R$_a$ and R$_b$ are each independently

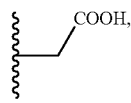

R$_d$ is hydrogen and substituent group R$_e$ is

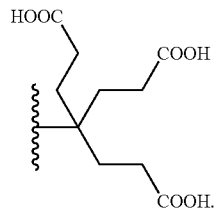 [SMILES: *C(CCC(=O)O)(CCC(=O)O)CCC(=O)O]

For certain compounds according to Formula I R$_a$ and R$_d$ are each independently hydrogen, and R$_b$ and R$_e$ (C$_1$-C$_6$)alkyl, for example, an alkyl group that is further substituted with carboxyalkylene groups. Exemplary of such a Formula I compound is one in which R$_a$ and R$_d$ are each independently hydrogen, and R$_b$ and R$_e$ are

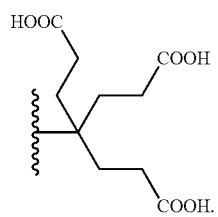 [SMILES: *C(CCC(=O)O)(CCC(=O)O)CCC(=O)O]

As mentioned above herein, compounds according to Formula I are inhibitors of the enzyme Ca IX. Complexes of a Formula I compound with radionuclides, therefore, are candidate radioimaging agents for detecting and monitoring the progression of cancers.

Exemplary poly(carboxyl)amine-containing Formula I compounds include without limitation those illustrated in Table 1.

TABLE 1
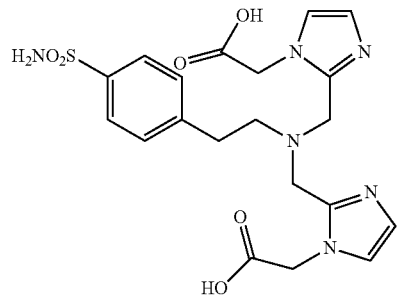 [SMILES: NS(=O)(=O)c1ccc(CCN(Cc2nccn2CC(=O)O)Cc2nccn2CC(=O)O)cc1]
(1)
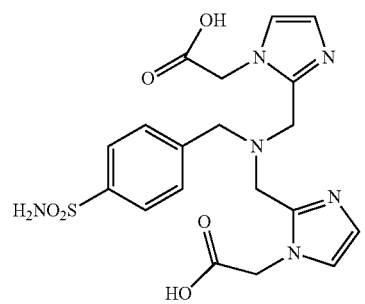 [SMILES: NS(=O)(=O)c1ccc(CN(Cc2nccn2CC(=O)O)Cc2nccn2CC(=O)O)cc1]
(2)
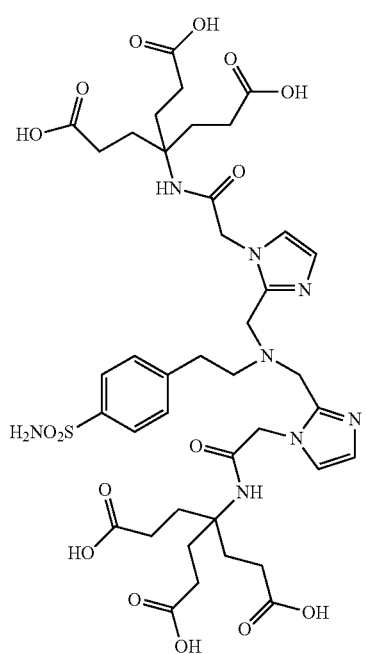 [SMILES: NS(=O)(=O)c1ccc(CCN(Cc2nccn2CC(=O)NC(CCC(=O)O)(CCC(=O)O)CCC(=O)O)Cc2nccn2CC(=O)NC(CCC(=O)O)(CCC(=O)O)CCC(=O)O)cc1]
(3)

TABLE 1-continued
(4)
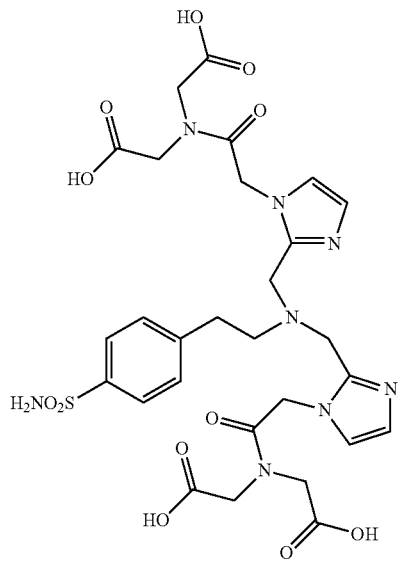 [SMILES: NS(=O)(=O)c1ccc(CCN(Cc2nccn2CC(=O)N(CC(=O)O)CC(=O)O)Cc2nccn2CC(=O)N(CC(=O)O)CC(=O)O)cc1]
(5)
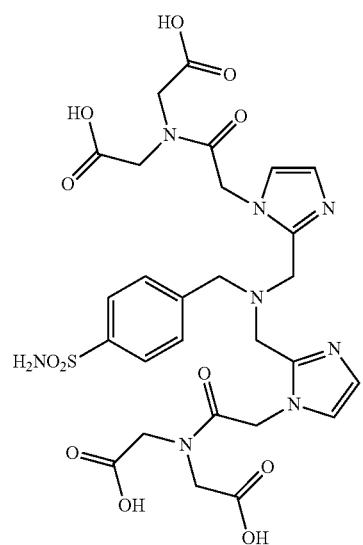 [SMILES: NS(=O)(=O)c1ccc(CN(Cc2nccn2CC(=O)N(CC(=O)O)CC(=O)O)Cc2nccn2CC(=O)N(CC(=O)O)CC(=O)O)cc1]
(6)
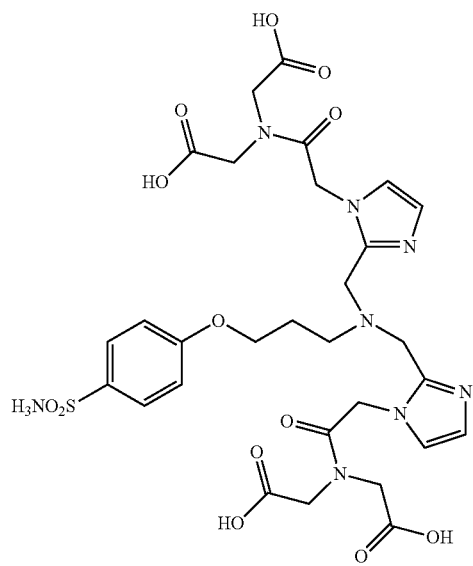

TABLE 1-continued
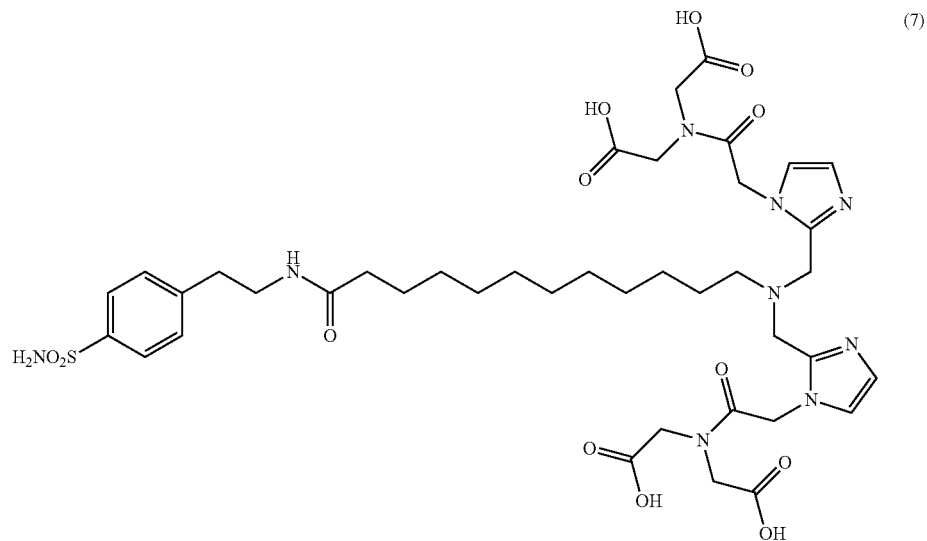
(7)
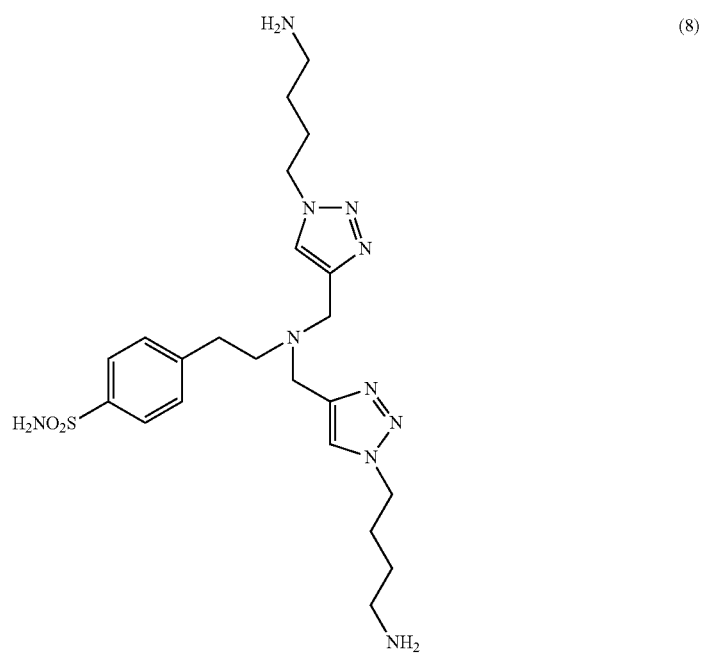
(8)

TABLE 1-continued
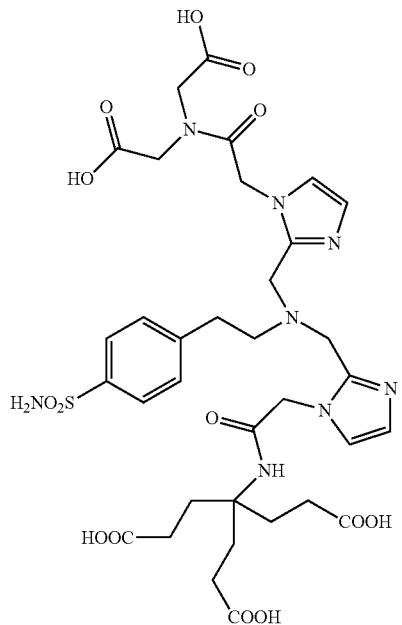 [SMILES: NS(=O)(=O)c1ccc(CCN(Cc2nccn2CC(=O)NC(CCC(=O)O)(CCC(=O)O)CCC(=O)O)Cc2nccn2CC(=O)N(CC(=O)O)CC(=O)O)cc1]
(9)
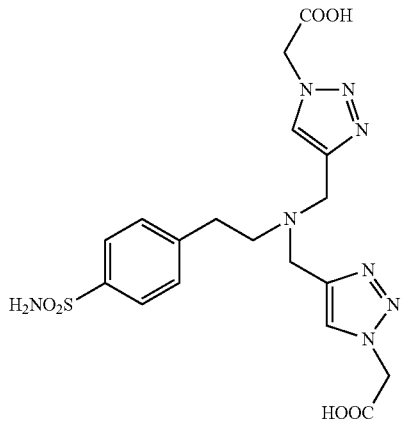 [SMILES: NS(=O)(=O)c1ccc(CCN(Cc2cn(CC(=O)O)nn2)Cc2cn(CC(=O)O)nn2)cc1]
(10)
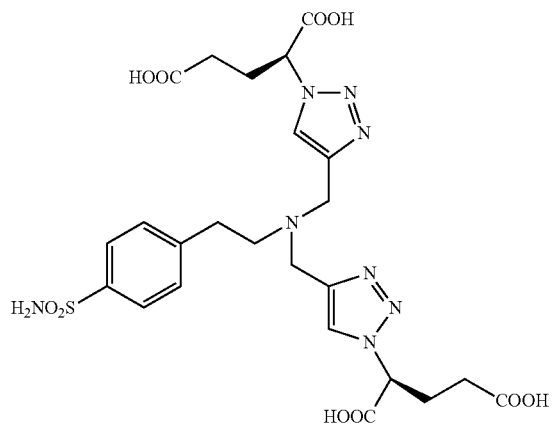 [SMILES: NS(=O)(=O)c1ccc(CCN(Cc2cn([C@@H](CCC(=O)O)C(=O)O)nn2)Cc2cn([C@@H](CCC(=O)O)C(=O)O)nn2)cc1]
(11)

The present invention is also directed to the synthesis and use of metal complexes of poly(carboxyl)amine-containing Formula I compounds. According to an embodiment of the present invention, metal complexes that conform to Formula II are provided, including radionuclide and non-radionuclide metal complexes.

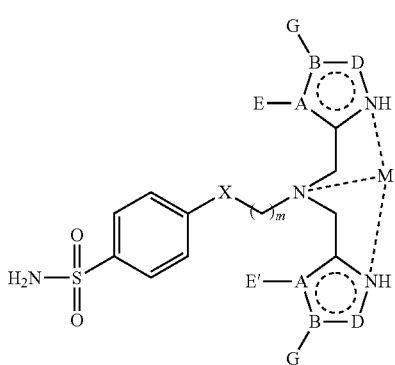

For complexes according to Formula II, X is selected from the group consisting of —(CH$_2$)$_n$—, —(CH$_2$)$_n$—O—, —(CH$_2$)$_n$—N(R$_g$)—, —(CH$_2$)$_n$—N(R$_g$)—C(O)— and —O—, each R$_g$ is hydrogen or (C$_1$-C$_6$)alkyl and groups A, B and D are each independently —(CH)—, or —N—.

Substituent E is —(CH$_2$)—Z-Q, while E' is —(CH$_2$)—Z—V. Group Z is β(CH$_2$)$_p$—, or —C(O)—. In Formula II, Q is selected from —H, —OR$_g$, or NR$_a$R$_b$ and Q' is selected from —H, —OR$_g$, or NR$_d$R$_e$. Substituent groups R$_a$, R$_b$ R$_d$ and R$_e$ each are independently hydrogen, (C$_1$-C$_6$)alkyl, or carboxy (C$_1$-C$_6$)alkylene, while substituent G is —(CH(R$_m$))$_n$—R$_h$—, or —(CH$_2$)$_p$—C(O)—R$_h$.

Group R$_h$ in Formula II is —H, —OH, NR$_a$R$_b$, or CO$_2$H, while R$_m$ is —H, —COOH, —COO(C$_1$-C$_6$)alkyl. Subscripts m, n and p independently are integers between 0 to 10 inclusive. Formula II also provides for aromatic or non-aromatic compounds by providing the option of having one or more double bonds using the symbol ⌒. M can be any radionuclide or non-radionuclide metal, preferably, rhenium-186, rhenium-188, copper-64, technetium-99m, platinum, manganese, zinc and the like.

In Formula II, moreover, any alkyl, heteroaryl, amine, or carboxyalkyl can be optionally substituted with one or more members selected from the group consisting of hydrogen, carboxy(C$_1$-C$_6$)alkylene, hydroxy(C$_1$-C$_6$)alkylene and amino(C$_1$-C$_6$)alkylene.

Exemplary Formula II complexes, in this case, rhenium tricarbonyl complexes include without limitation those illustrated in Table 2.

TABLE 2

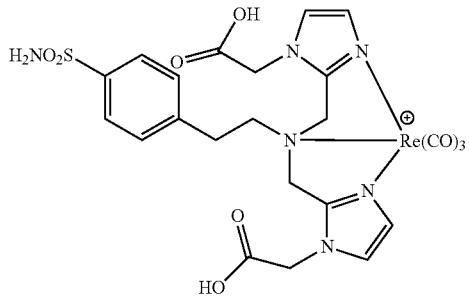

Re-(1)

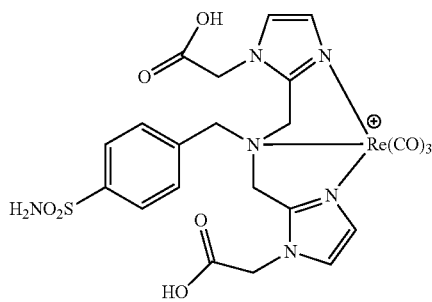

Re-(2)

TABLE 2-continued
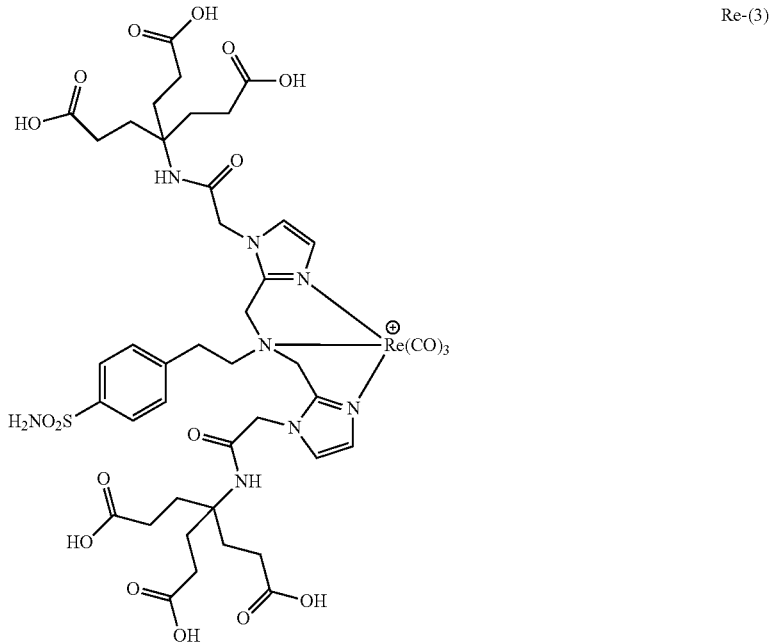
Re-(3)
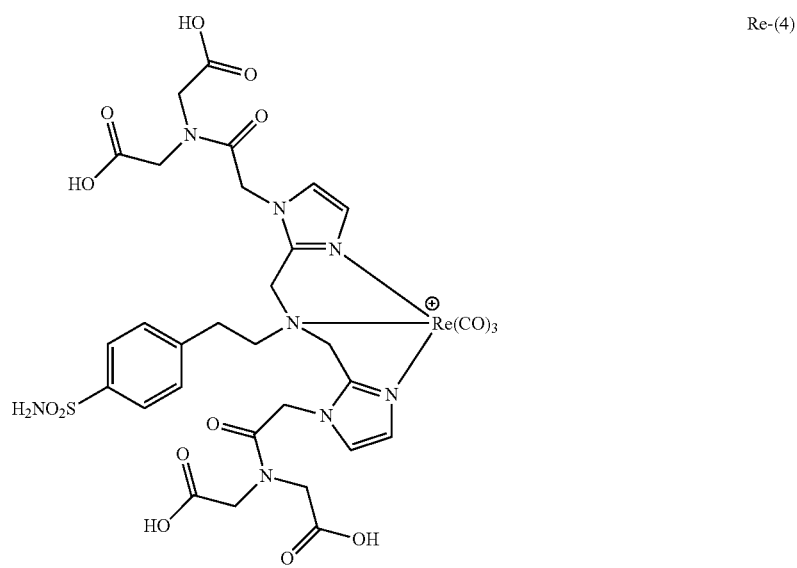
Re-(4)

TABLE 2-continued
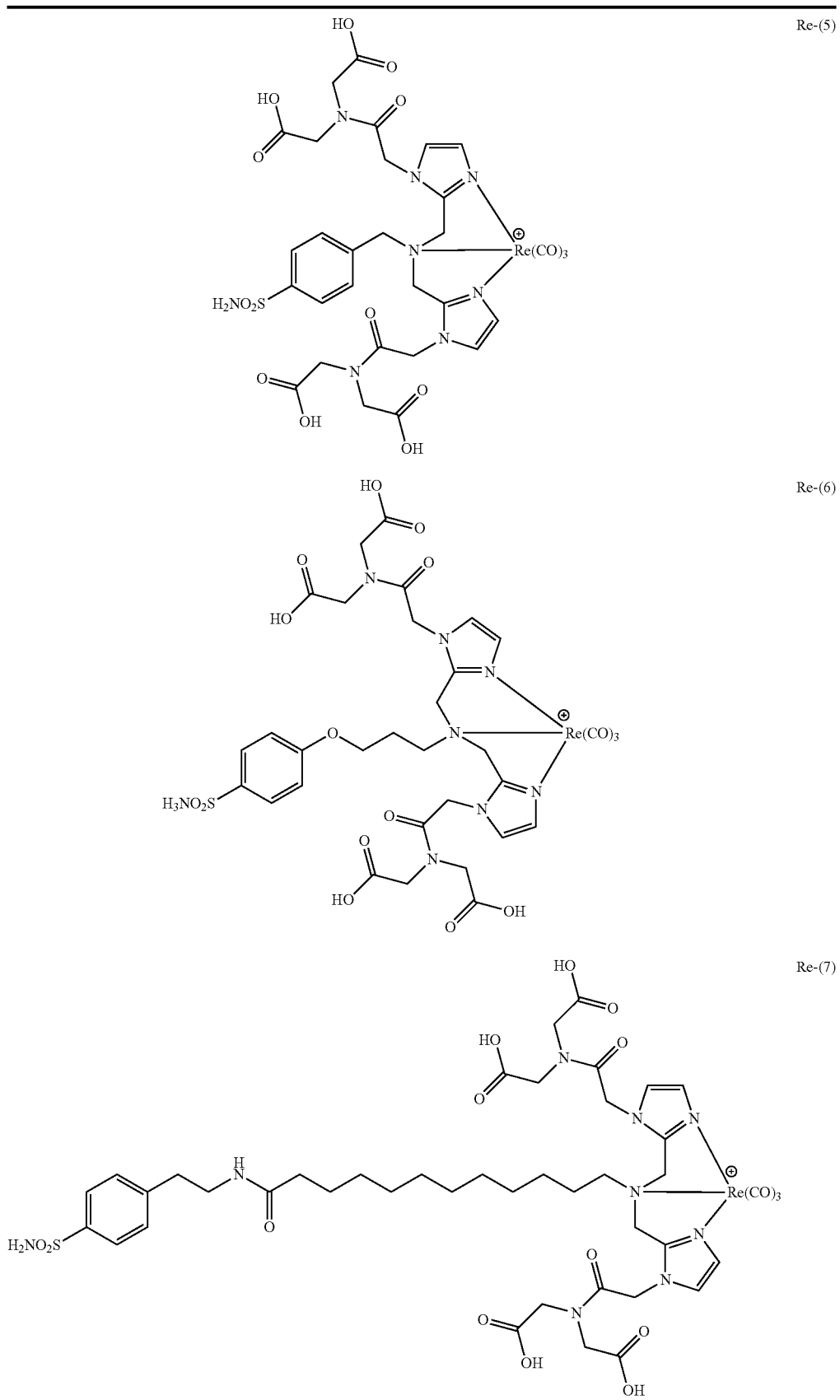

TABLE 2-continued
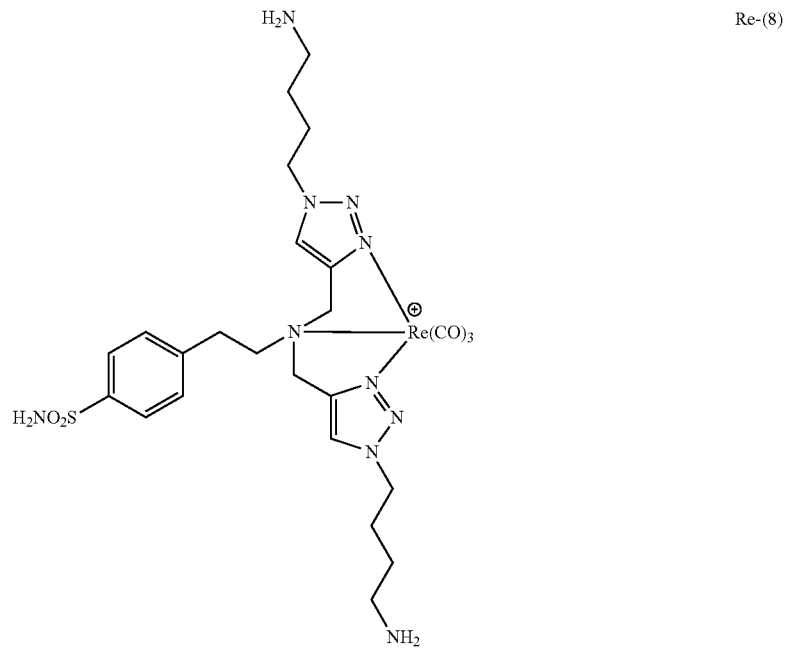
Re-(8)
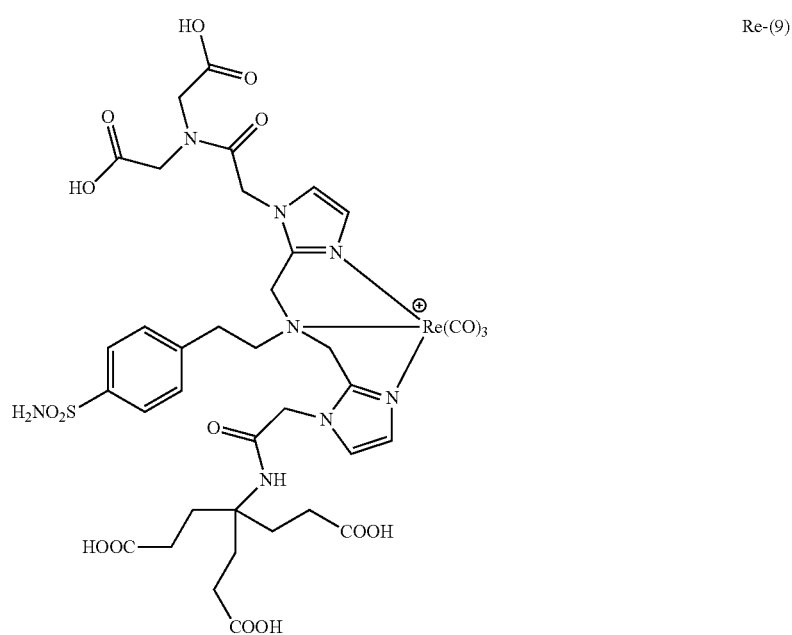
Re-(9)

TABLE 2-continued

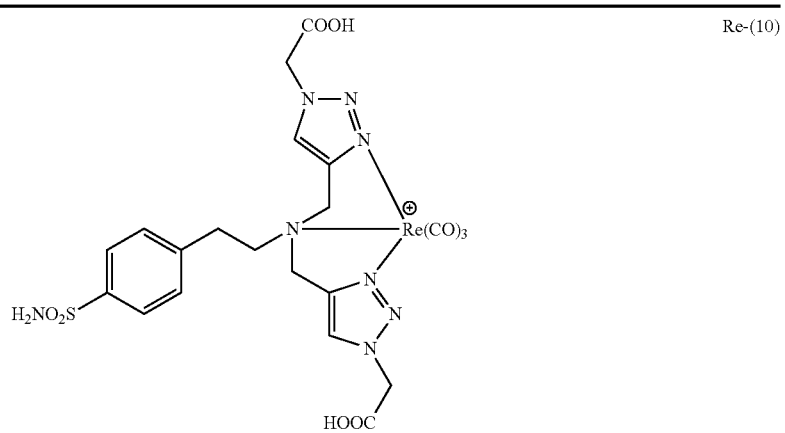

Re-(10)

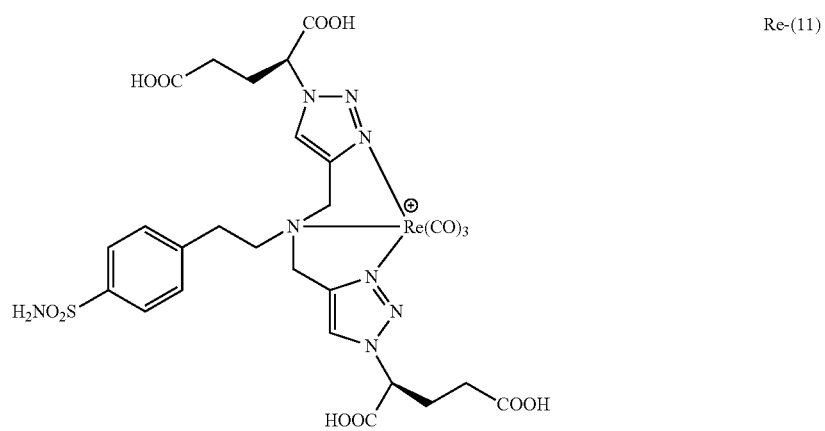

Re-(11)

According to another embodiment, the present invention provides a method of preparing an imaging or therapeutic agent for targeting CA IX expressing tumor tissue using a Formula II complex. The inventive method comprises contacting a metal selected from the group consisting of Pt, Zn, $^{64}$Cu, $^{186}$Re, $^{188}$Re and $^{99m}$Tc with excess of a compound according to Formula I using a pharmaceutically acceptable carrier, to provide a mixture that comprises the desired Formula II metal complex as well as quantities of the corresponding free, uncomplexed Formula I compound.

In one embodiment, the percent amount of the metal-complexed Formula I compound in the reaction mixture is from about 0.01% to about 100%. According to some embodiments, the inventive method for of preparing an imaging agent for targeting CA IX expressing tumor tissue provides a mixture that has from about 0.01% to about 90%, from about 0.01% to about 80%, from about 0.01% to about 60%, from about 0.01% to about 50%, from about 0.01% to about 40%, from about 0.01% to about 30%, from about 0.01% to about 20%, from about 0.01% to about 10%, from about 0.01% to about 5%, from about 0.01% to about 1.0% of the metal-complexed Formula I compound.

As further described below, formation of the metal complexes with Pt, Zn $^{64}$Cu, $^{186}$Re, $^{188}$Re or $^{99m}$Tc improves binding affinity for CA IX. That is, the metal complex of a Formula I compound was found to bind more tightly (lower $IC_{50}$) to CA IX expressed in HeLa cells than the corresponding free, uncomplexed compound, at times, by one or two or more orders of magnitude To explore the molecular basis of tight binding, the present inventors synthesized and tested Formula I compounds (and contemplate additional variations) (a) to investigate the role of linker length (the distance of the radionuclide chelator group from the sulfonamide group) in modulating CA IX inhibition; (b) to investigate the role of the type (chemical nature) of radionuclide chelator groups in modulating CA IX inhibition; and (c) to investigate the role of the chemical nature of the linker that separates the radionuclide chelator group from the sulfonamide group.

Illustratively, these predictors of tight-binding interactions are shown in Schemes I-III below.
Investigation of the Linker
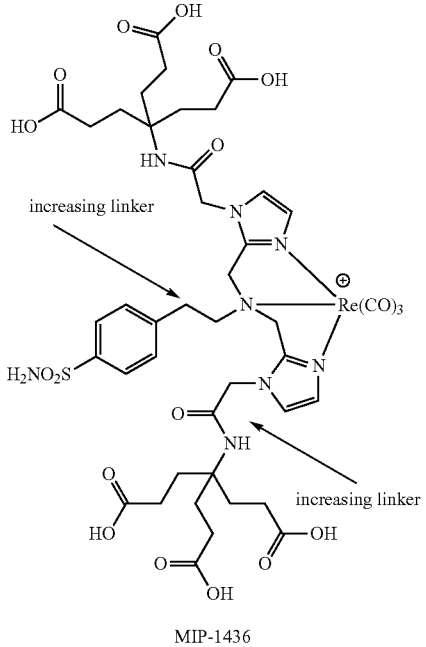
MIP-1436
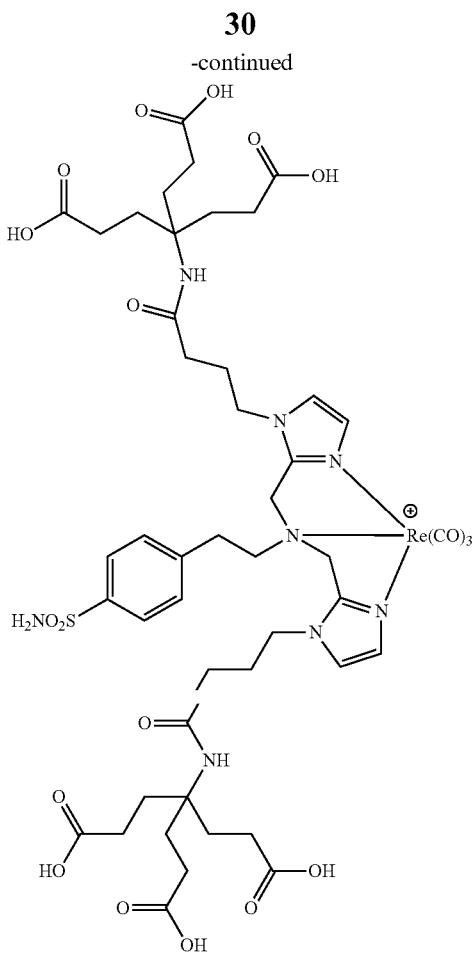
-continued
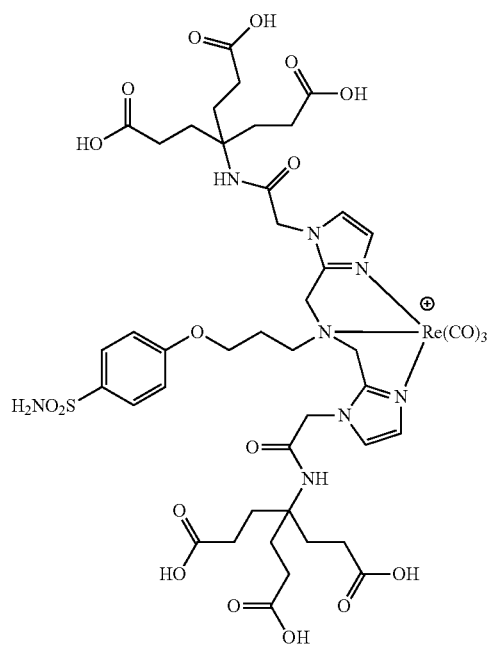
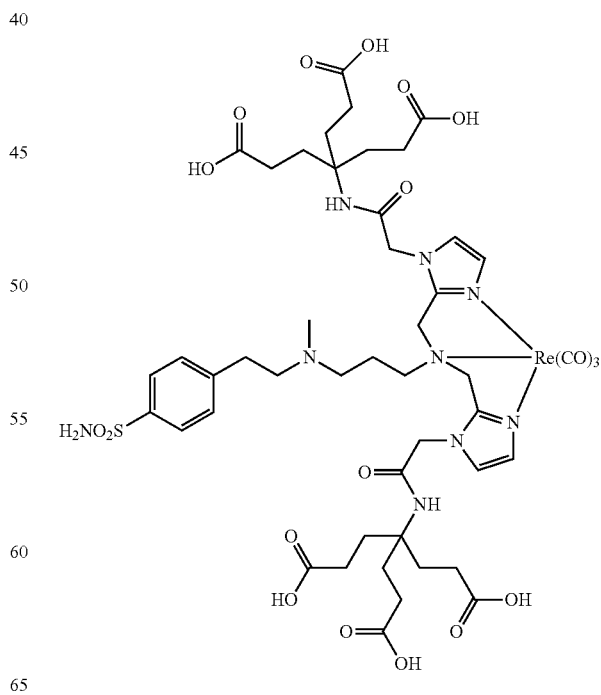

Bis(triazole) Series
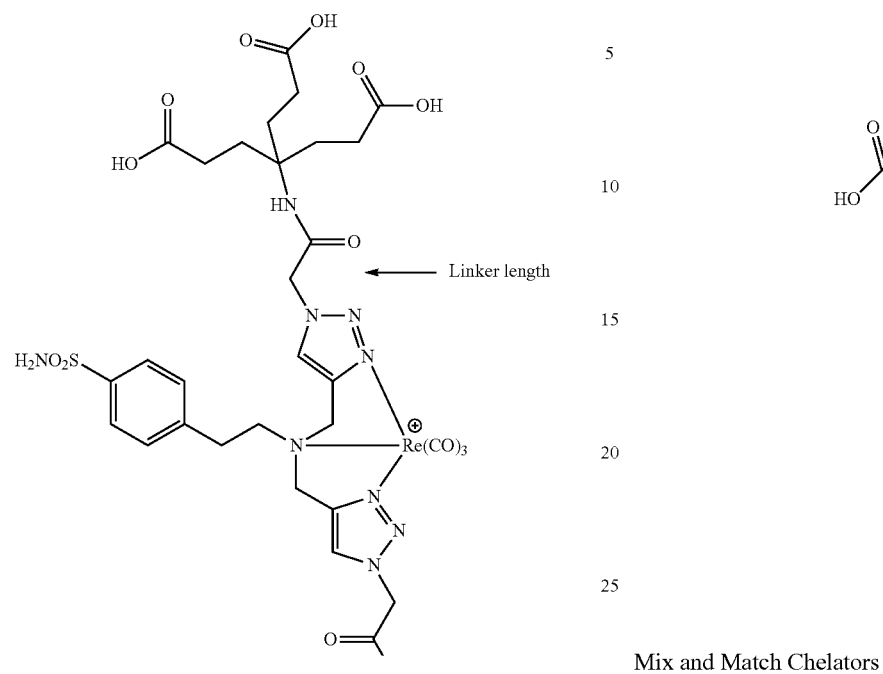
← Linker length
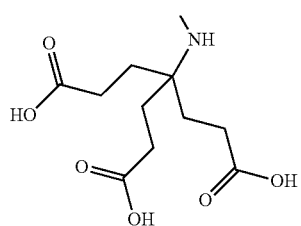
Mix and Match Chelators

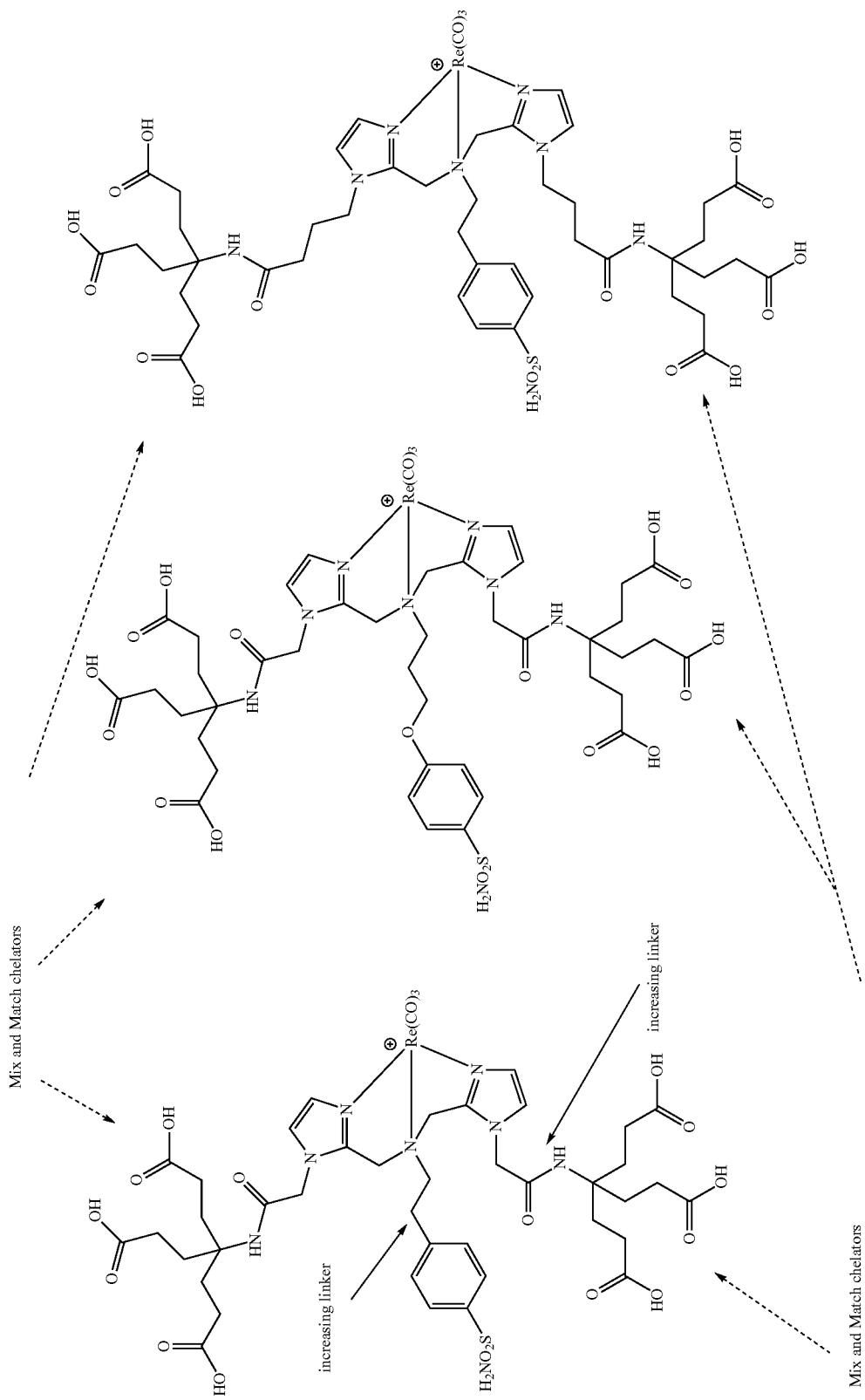

As shown by the structures below, for radionuclide complexes of Formula I compounds having an imidazole moiety as the chelator group, changing the length of the linker from a two carbon spacer to a single carbon spacer decreased the $IC_{50}$ by more than 12-fold. See, for example, Re-(1) and Re-(2).

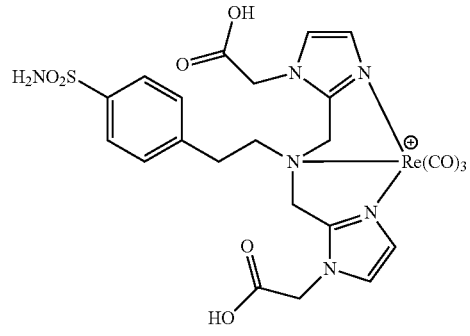

Re-1

$IC_{50}$ (HeLa cells) = 3.8 nM

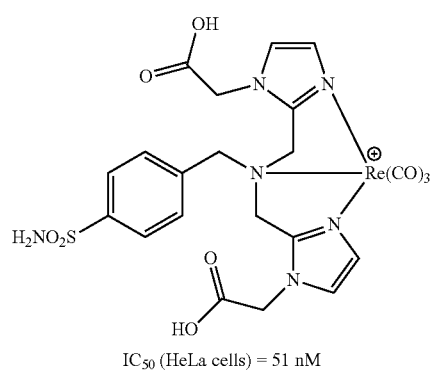

Re-2

$IC_{50}$ (HeLa cells) = 51 nM

A similar decrease in $IC_{50}$ value is observed when the $IC_{50}$ of rhenium complex for Re-(4) is compared to Re-(5).

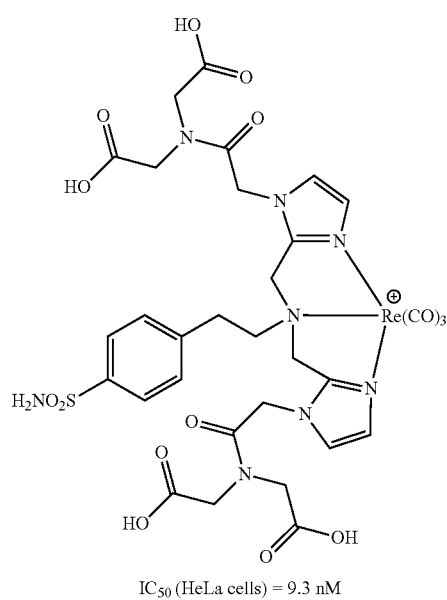

Re-4

$IC_{50}$ (HeLa cells) = 9.3 nM

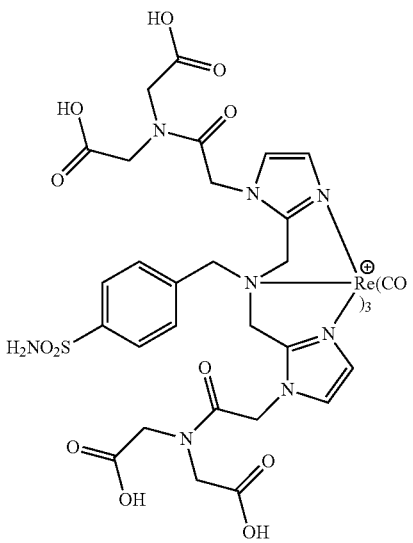

Re-5

$IC_{50}$ (HeLa cells) = 116 nM

Further increase in the length of the linker abrogates binding activity. For instance, reacting the amino group of 4-(2-aminoethyl)benzenesulfonamide with 12-aminododecanoic acid to obtain a 15-atom linker (see MIP 1442) weakened binding to CA IX protein by 500-fold. Taken together, these results indicate that the distance by which the chelator group is separated from the sulfonamide moiety is important in binding to CA IX as shown by the $IC_{50}$ values for complexes of Formula I compounds.

Substitution of the bis(imidazolemethyl) group with a bis (1H-1,2,3-triazolemethylene) moiety as the chelating group gave Formula I compounds which upon complexation with rhenium tricarbonyl gave CA IX inhibitors with $IC_{50}$ values in the 50 nM to 300 nM range. Exemplary triazolo compounds that conform to Formula I and their rhenium tricarbonyl complexes conforming to Formula II are shown below.

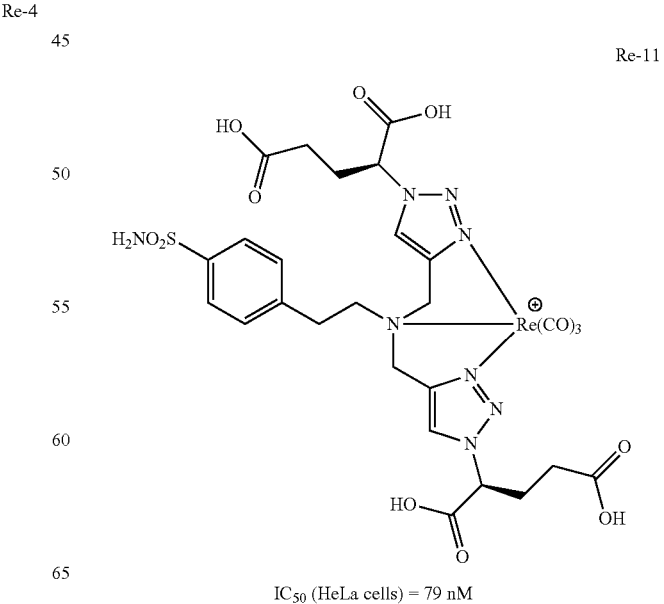

Re-11

$IC_{50}$ (HeLa cells) = 79 nM

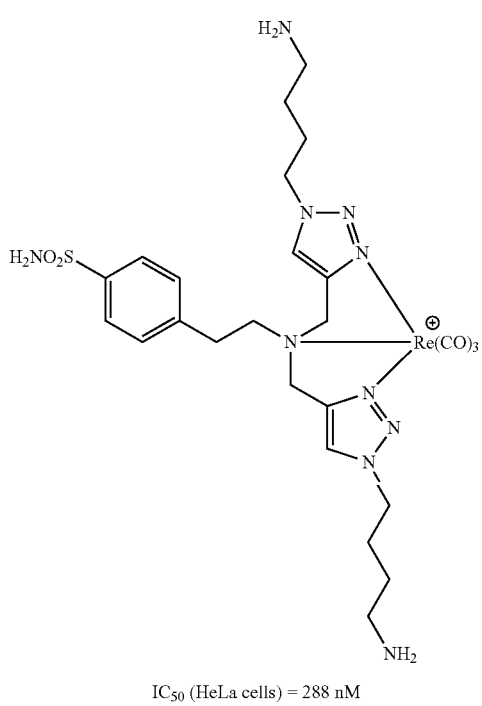

Re-8

IC$_{50}$ (HeLa cells) = 288 nM

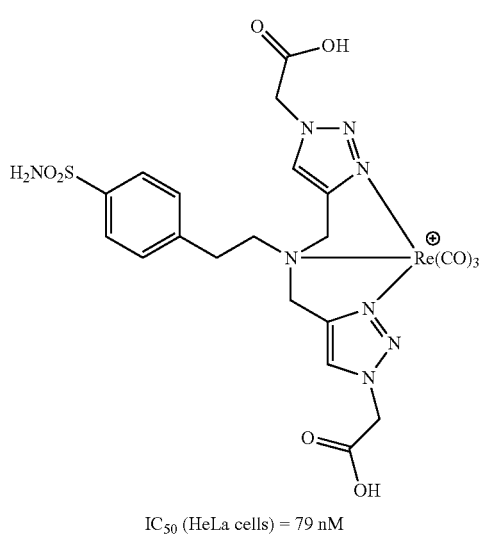

Re-10

IC$_{50}$ (HeLa cells) = 79 nM

Commercially, the inventive therapeutic or imaging agent will be provided to a physician or a qualified licensed medical practitioner in the form of a kit that will contain a Formula I compound its pharmaceutically acceptable salt, tautomer or ester. The compound can be in the form a dry lyophilized powder that is appropriately packaged, or can be provided in a sealed sterile vial that is opened prior to administration to a patient in need. According to one embodiment, the kit will contain an inventive therapeutic or imaging agent that has been dissolved in a suitable pharmaceutically acceptable carrier and is provided as a solution in a sealed sterile vial or scored ampule. Whether the Formula I compound is provided as a powder or in solution form, it optionally can contain other pharmaceutically acceptable reagents such as sodium boranocarbonate, sodium carbonate, sodium tartarate and sodium borate that help stabilize, buffer and increase the shelf life of the Formula I compounds.

When the inventive therapeutic or imaging agent is provided as a dry lyophilized powder, the medical practitioner will reconstitute the powder in an appropriate volume of a pharmaceutically acceptable solvent at the site of administration. Whatever the form of the inventive Formula I compound in the kit, a solution of this compound is combined with an appropriate radionuclide precursor prior to administration to the patient.

Instructions for reconstitution of the powder in a suitable solvent, along with instructions for complexing the reconstituted Formula I compound with a radionuclide source, such as pertechnetate which is exemplary of a convenient water-soluble source of isotopes of the radioactive element technetium, will generally be included within the kit.

SYNTHESIS

A. General Experimental:

All reactions were carried out in dry glassware under an atmosphere of argon or nitrogen unless otherwise noted. Reactions were purified by flash column chromatography, medium pressure using a Biotage SP4 or by preparative high pressure liquid chromatography. $^1$H NMR was recorded on a Bruker 400 MHz instrument. Spectra are reported as ppm δ and are referenced to the solvent resonances in CDCl$_3$, DMSO-d$_6$ or methanol-d$_4$. All solvents were purchased from Sigma-Aldrich. Reagents were purchased from Sigma Aldrich, Bachem, Fisher, Alfa Aesar, and Acros. The following abbreviations are used dichloromethane (DCM), ethyl acetate (EA), hexanes (Hex), dichloroethane (DCE), dimethyl formamide (DMF), trifluoroacetic acid (TFA), tetrahydrofuran (THF), carbonyldiimidazole (CDI), dicyclohexyl carbodiimide (DCC), dimethylaminopyridine (DMAP), t-butyloxycarbonyl (BOC), diisopropylethylamine (DIPEA), triethylamine (TEA), benzyloxycarbonyl (CBZ), ethanol (EtOH), methanol (MeOH).

B. General Radiolabeling Procedure

[$^{99m}$Tc(CO)$_3$(H$_2$O)$_3$]$^+$ was prepared using the Isolink® radiolabeling kits by the methods published in the literature. Sodium Pertechnetate, 7400 MBq (200 mCi), in saline (2.5 mL) was added to an Isolink® radiolabeling kit and the vial was placed in an oil bath at 100° C. The reaction was heated for 45 minutes and 1N HCl (200 μL) was then added to neutralize the reaction mixture. The product, [$^{99m}$Tc(CO)$_3$(H$_2$O)$_3$]$^+$, was removed from the vial via syringe and added to another vial containing the desired free ligand (200 μL of a 1 mg/mL solution in methanol) followed by an additional amount of methanol (0.3 mL). The reaction was heated for 1 hour at 80° C. and the crude reaction was injected on the HPLC to determine radiochemical purity (RCP) of the crude reaction product was followed by Sep Pak purification to afford the desired product with a RCP of >90%.

Example 1

[Re(CO)₃][4,4'-((2,2'-(2,2'-(((4-sulfamoylphenethyl)azanediyl)bis(methylene))bis(1H-imidazole-2,1-diyl))bis(acetyl))bis(azanediyl))bis(4-(2-carboxyethyl)heptanedioic acid)] (Re-(3))

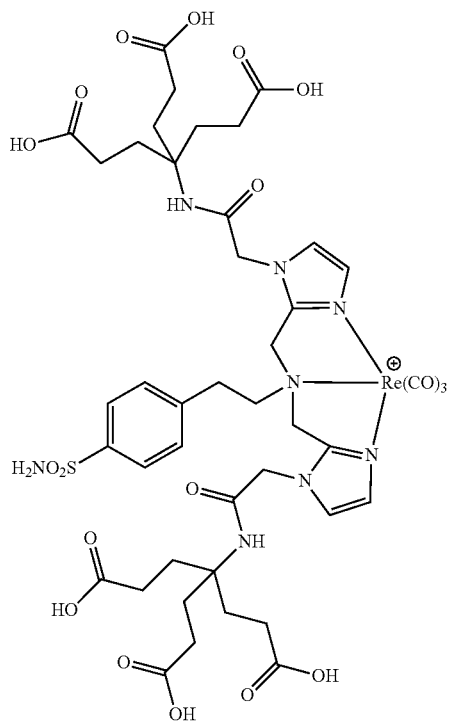

Step 1. di-tert-butyl 4-(2-bromoacetamido)-4-(3-(tert-butoxy)-3-oxopropyl) heptanedioate

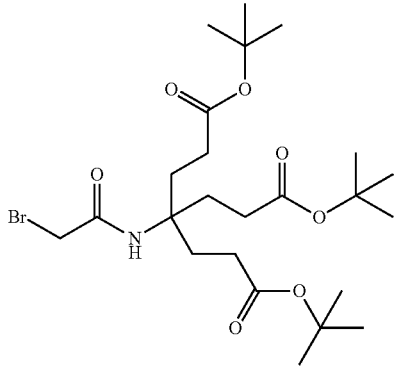 [SMILES: CC(C)(C)OC(=O)CCC(CCC(=O)OC(C)(C)C)(CCC(=O)OC(C)(C)C)NC(=O)CBr]

To a solution of di-tert-butyl 4-amino-4-(3-(tert-butoxy)-3-oxopropyl)heptanedioate (5.00 g, 12.0 mmol) and 2-bromoacetyl bromide (1.46 mL, 3.40 g, 16.80 mmol) in DCM (60 mL) was added Et₃N (2.5 mL) at room temperature. The reaction mixtures were stirred at room temperature for overnight. The reaction mixtures were diluted with DCM (300 mL), washed with 1N HCl solution, and dried over Na₂SO₄. Solvent was evaporated under reduce pressure to afford a residue, which was purified by biotage eluting with 10% EtOC in hexanes to 100% EtOAc to afford di-tert-butyl 4-(2-bromoacetamido)-4-(3-(tert-butoxy)-3-oxopropyl)heptanedioate (2.58 g, 40%). $^1$H NMR (400 MHz, CDCl₃) 6.43 (s, 1H), 3.76 (s, 2H), 2.20 (t, J=8.0 Hz, 2H), 1.98 (t, J=8.0 Hz, 6H), 1.43 (s, 27H); MS (ESI), 558, 560 (M+Na)⁺.

Step 2. di-tert-butyl 4-(3-(tert-butoxy)-3-oxopropyl)-4-(2-(2-formyl-1H-imidazol-1-yl)acetamido)heptanedioate

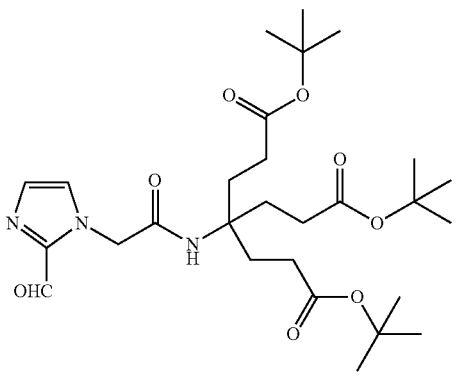 [SMILES: CC(C)(C)OC(=O)CCC(CCC(=O)OC(C)(C)C)(CCC(=O)OC(C)(C)C)NC(=O)Cn1ccnc1C=O]

A solution of di-tert-butyl 4-(2-bromoacetamido)-4-(3-(tert-butoxy)-3-oxopropyl)heptanedioate (1.397 g, 2.61 mmol), 1H-imidazole-2-carbaldehyde (0.30 g, 3.13 mmol), DIPEA (2.0 mL), and KI (0.30 g) in DMF (5.0 mL) was stirred at 80° C. for 5 hrs. The solvent was evaporated under reduced pressure to afford a residue, which was purified by biotage eluting with 20% EtOAc in hexanes to 100% EtOAc to give di-tert-butyl 4-(3-(tert-butoxy)-3-oxopropyl)-4-(2-(2-formyl-1H-imidazol-1-yl)acetamido)heptanedioate (0.90 g, 63%). $^1$H NMR (400 MHz, CDCl₃) 9.78 (s, 1H), 7.32 (s, 1H), 7.23 (s, 1H), 6.65 (s, 1H), 4.90 (s, 2H), 2.19 (t, J=7.8 Hz, 6H), 1.94 (t, J=7.8 Hz, 6H), 1.42 (s, 9H); MS (ESI), 552 (M+H)⁺.

Step 3. tetra-tert-butyl 4,4'-((2,2'-(2,2'-(((4-sulfamoylphenethyl)azanediyl)bis(methylene))bis(1H-imidazole-2,1-diyl))bis(acetyl))bis(azanediyl))bis(4-(3-(tert-butoxy)-3-oxopropyl)heptanedioate

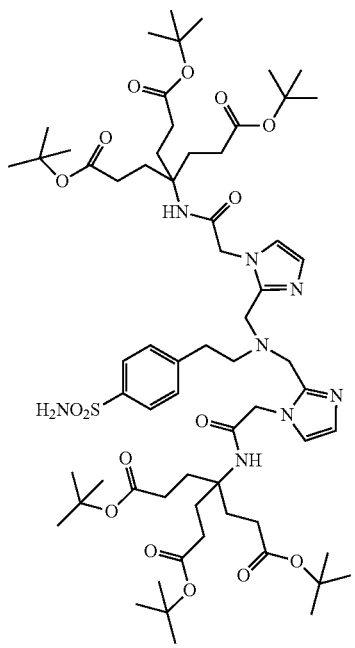 [SMILES: CC(C)(C)OC(=O)CCC(CCC(=O)OC(C)(C)C)(CCC(=O)OC(C)(C)C)NC(=O)Cn1ccnc1CN(CCc1ccc(S(N)(=O)=O)cc1)Cc1nccn1CC(=O)NC(CCC(=O)OC(C)(C)C)(CCC(=O)OC(C)(C)C)CCC(=O)OC(C)(C)C]

A solution of 4-(2-aminoethyl)benzenesulfonamide (80 mg, 0.40 mmol), AcOH (0.05 mL) and di-tert-butyl 4-(2-bromoacetamido)-4-(3-(tert-butoxy)-3-oxopropyl)heptanedioate (447 mg, 0.81 mmol) in DCE (20 mL) was stirred at 80° C. for 30 min under nitrogen. The reaction mixture was cooled to 0° C., and treated with NaBH(OAc)$_3$ (0.254 g, 1.2 mmol). The reaction mixture was stirred at room temperature for overnight and decomposed with water. The reaction mixture was extracted with DCM. The organic layer was dried and concentrated under reduced pressure. The residue was purified by biotage over silica gel to afford the desired product (322 mg, 63%). $^1$H NMR (400 MHz, DMSO-d$_6$) 7.77 (s, 2H), 7.64 (d, J=8.0 Hz, 2H), 7.23 (s, 2H), 7.21 (d, J=8.4 Hz, 2H), 7.01 (s, 2H), 6.80 (s, 2H), 4.57 (s, 4H), 3.61 (s, 4H), 2.79-2.62 (m, 4H), 2.09 (t, J=8.0 Hz, 12H), 1.76 (t, J=8.0 Hz, 12H), 1.32 (s, 54H); MS (ESI), 636.5 (M/2+H)$^+$.

Step 4. Re(CO)$_3$][4,4'-((2,2'-(2,2'-(((4-sulfamoylphenethyl)azanediyl)bis(methylene))bis(1H-imidazole-2,1-diyl))bis(acetyl))bis(azanediyl))bis(4-(2-carboxyethyl)heptanedioic acid)] (Re-(3))

A solution of tetra-tert-butyl 4,4'-((2,2'-(2,2'-(((4-sulfamoylphenethyl)azanediyl)bis(methylene))bis(1H-imidazole-2,1-diyl))bis(acetyl))bis(azanediyl))bis(4-(3-(tert-butoxy)-3-oxopropyl)heptanedioate (167 mg, 0.131 mmol) and [NEt$_4$]$_2$[ReBr$_3$(CO)$_3$] (116 mg, 0.15 mmol) in MeOH (5.0 mL) was stirred at 95° C. for 4 hrs at a pressure tube. Solvent was evaporated under reduced pressure to give crude product. A solution of crude product in TFA (1.0 mL) and DCM (1.0 mL) was stirred at room temperature for overnight. Solvent was removed under reduced pressure to give a residue, which was purified by HPLC to give desired product as a white solid (75 mg, 48%). $^1$H NMR (400 MHz, DMSO-d$_6$) 12.10 (brs, 6H), 7.78 (d, J=8.4 Hz, 2H), 7.71 (s, 2H), 7.55 (d, J=8.0 Hz, 2H), 7.27 (s, 2H), 7.17 (s, 2H), 7.03 (s, 2H), 4.72 (s, 4H), 4.64 (d, J=16.4 Hz, 2H), 4.52 (d, J=16.4 Hz, 2H), 3.86-3.82 (m, 2 yl), 3.13-3.09 (m, 2H), 2.14 (t, J=8.0 Hz, 6H), 1.85 (t, J=8.0 Hz, 6H); MS (ESI), 601.2 M$^-$.

Example 2

[Re(CO)$_3$][2,2',2'',2'''-((2,2'-(2,2'-(((4-(4-sulfamoylphenoxy)butyl)azanediyl)bis(methylene))bis(1H-imidazole-2,1-diyl))bis(acetyl))bis(azanetriyl))tetraacetic acid] (Re-(12))

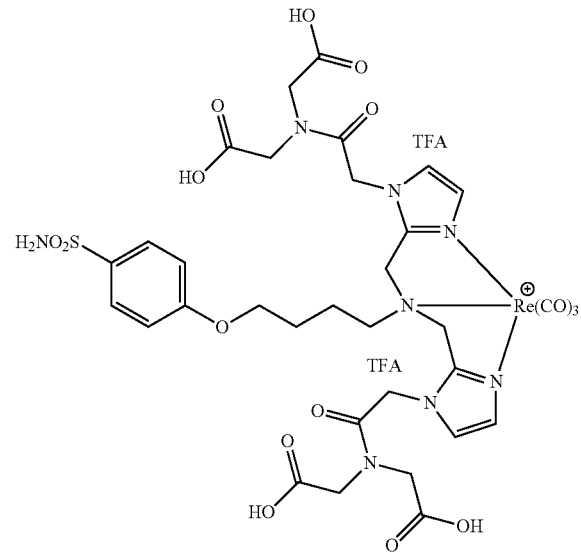

Step 1. tert-butyl(4-(4-sulfamoylphenoxy)butyl)carbamate

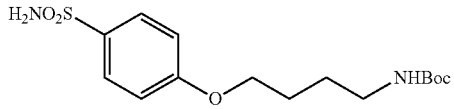 [SMILES: CC(C)(C)OC(=O)NCCCCOc1ccc(S(N)(=O)=O)cc1]

To a solution of 4-hydroxybenzenesulfonamide (1.211 g, 7.0 mmol) and tert-butyl(4-bromobutyl)carbamate (1.26 g, 5.0 mmol) in acetonitrile (50 mL) was added anhydrous K$_2$CO$_3$ (1.38 g, 10 mmol). The reaction mixtures were stirred at 75° C. for overnight. Solvent was evaporated under reduced pressure to give a residue. The residue was diluted with 1 N HCl (20 mL), extracted with DCM, and dried over Na$_2$SO$_4$. Solvent was evaporated under reduce pressure to afford a residue, which was purified by biotage eluting with DCM to 10% MeOH in DCM to afford tert-butyl(4-(4-sulfamoylphenoxy)butyl)carbamate as a white solid (0.720 g, 42%). $^1$H NMR (400 MHz, DMSO) 7.70 (d, J=8.8 Hz, 2H), 7.16 (s, 2H), 7.04 (d, J=8.8 Hz, 2H), 6.82 (brs, 1H), 4.01 (t, J=6.6 Hz, 2H), 2.94 (q, J=6.4 Hz, 2 II), 1.69-1.64 (m, 2H), 1.52-1.46 (m, 2H), 1.35 (s, 9H); MS (ESI), 367.1 (M+Na)$^+$.

Step 2. 4-(4-aminobutoxy)benzenesulfonamide

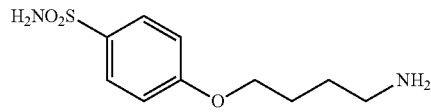 [SMILES: NCCCCOc1ccc(S(N)(=O)=O)cc1]

A solution of tert-butyl(4-(4-sulfamoylphenoxy)butyl)carbamate (0.72 g, 2.09 mmol) in TFA (5.0 mL) and DCM (5.0 mL) was stirred at rt for overnight. After the solvent was evaporated under a steam of N$_2$, the reaction mixture was dissolved in water (20.0 mL) and acetonitrile (5.0 mL) and lyophilized to afford 4-(4-aminobutoxy)benzenesulfonamide as a yellow solid (0.906 g) containing TFA. $^1$H NMR (400 MHz, DMSO) 7.74-7.72 (m, 4H), 7.20 (s, 2H), 7.06 (d, 2H), 4.06 (t, 2H), 2.89-2.82 (m, 2H), 1.80-1.75 (m, 2H), 1.71-1.65 (m, 2H); MS (ESI), 245.1 (M+H)$^+$.

Step 3. tetra-tert-butyl 2,2',2'',2'''-((2,2'-(2,2'-(((4-(4-sulfamoylphenoxy)butyl)azanediyl)bis(methylene))bis(1H-imidazole-2,1-diyl))bis(acetyl))bis(azanetriyl))tetraacetate

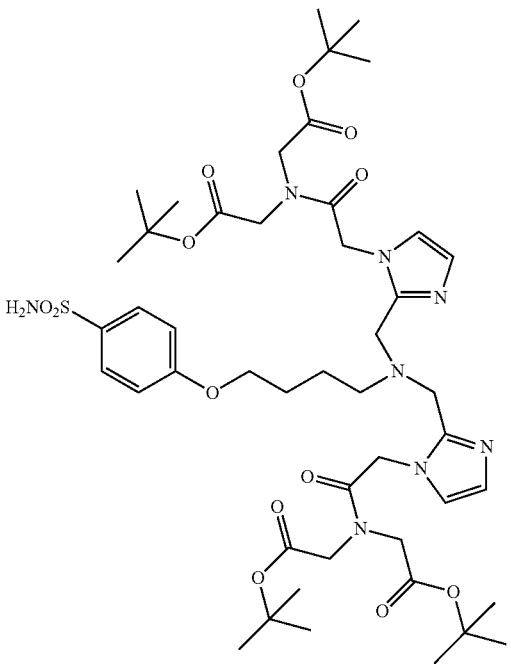 [SMILES: CC(C)(C)OC(=O)CN(CC(=O)OC(C)(C)C)C(=O)Cn1ccnc1CN(CCCCOc1ccc(S(N)(=O)=O)cc1)Cc1nccn1CC(=O)N(CC(=O)OC(C)(C)C)CC(=O)OC(C)(C)C]

A solution of 4-(4-aminobutoxy)benzenesulfonamide (437 mg, 1.0 mmol), AcOH (0.10 mL) and tert-butyl 2,2'-(2-(2-formyl-1H-imidazol-1-yl)acetylazanediyl)diacetate (838 mg, 2.2 mmol) in DCE (40 mL) was stirred at 75° C. for 45 min under nitrogen. The reaction mixture was cooled to 0° C., and treated with NaBH(OAc)$_3$ (0.423 g, 2.0 mmol). The reaction mixture was stirred at room temperature for overnight and decomposed with water. The reaction mixture was concentrated under reduced pressure to give a residue. The residue was purified by biotage over silica gel to afford tetra-tert-butyl 2,2',2'',2'''-((2,2'-(2,2'-(((4-(4-sulfamoylphenoxy) butyl)azanediyl)bis(methylene))bis(1H-imidazole-2,1-diyl)) bis(acetyl))bis(azanetriyl))tetraacetate (560 mg, 57%). MS (ESI), 975.3 (M+H)$^+$.

Step 4. [Re(CO)$_3$][2,2',2'',2'''-((2,2'-(2,2'-(((4-(4-sulfamoylphenoxy)butyl)azanediyl)bis(methylene)) bis(1H-imidazole-2,1-diyl))bis(acetyl))bis(azan-etriyl))tetraacetic acid] (Re-(12))

A solution of tetra-tert-butyl 2,2',2'',2'''-((2,2'-(2,2'-(((4-(4-sulfamoylphenoxy)butyl)azanediyl)bis(methylene))bis(1H-imidazole-2,1-diyl))bis(acetyl))bis(azanetriyl))tetraacetate (97.4 mg, 0.10 mmol) and [NEt$_4$]$_2$[ReBr$_3$(CO)$_3$] (80 mg, 0.10 mmol) in acetonitrile (5.0 mL) was stirred at 90° C. for 4 hrs at a pressure tube. Solvent was evaporated under reduce pressure to give crude product. A solution of crude product in TFA (2.0 mL) and DCM (2.0 mL) was stirred at room temperature for overnight. Solvent was removed under a stream of nitrogen to give a residue, which was purified by HPLC to give desired product as a white solid (70 mg, 69%). $^1$H NMR (400 MHz, DMSO-d$_6$) 7.73 (d, J=9.2 Hz, 2H), 7.18 (s, 2H), 7.11 (d, J=2.4 Hz, 2H), 7.10 (d, J=9.2 Hz, 2H), 7.03 (d, J=1.6 Hz, 2H), 5.00 (s, 4H), 4.39 (d, J=16.4 Hz, 2H), 4.29 (d, J=16.4 Hz, 2H), 4.23 (s, 4H), 4.12 (t, J=6.0 Hz, 2H), 4.02 (s, 4H), 3.79-3.75 (m, 2H), 1.92-1.80 (m, 4H); MS (ESI), 1021 M$^+$.

Example 3

[Re(CO)$_3$][4-(2-(2-((((1-(2-(bis(carboxymethyl) amino)-2-oxoethyl)-1H-imidazol-2-yl)methyl)(4-sulfamoylphenethyl)amino)methyl)-1H-imidazol-1-yl)acetamido)-4-(2-carboxyethyl)heptanedioic acid] (Re-(9))

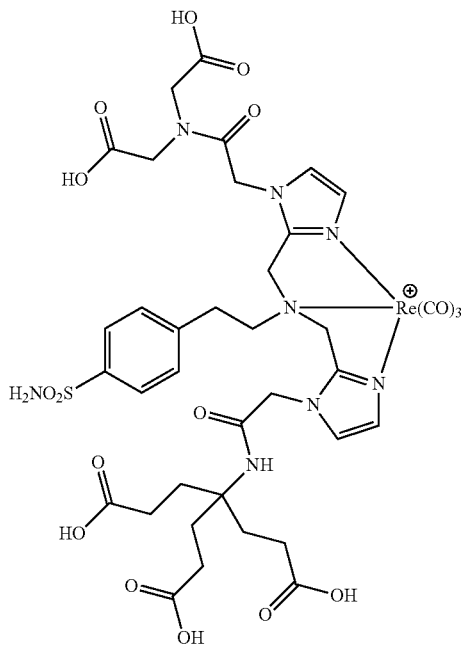

Step 1. di-tert-butyl 2,2'-((2-(2-(((4-sulfamoylphen-ethyl)amino)methyl)-1H-imidazol-1-yl)acetyl) azanediyl)diacetate

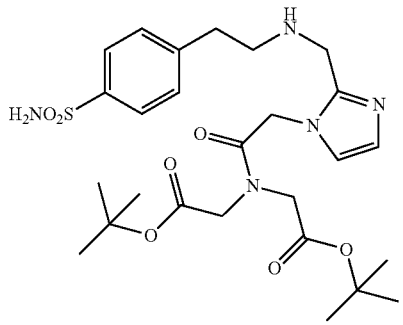 [SMILES: CC(C)(C)OC(=O)CN(CC(=O)OC(C)(C)C)C(=O)Cn1ccnc1CNCCc1ccc(S(N)(=O)=O)cc1]

A solution of 4-(4-aminobutoxy)benzenesulfonamide (2.40, 12.0 mmol), AcOH (0.40 mL) and tert-butyl 2,2'-(2-(2-formyl-1H-imidazol-1-yl)acetylazanediyl)diacetate (1.524 g, 4.0 mmol) in DCE (100 mL) was stirred at 75° C. for 30 min under nitrogen. The reaction mixture was cooled to 0° C., and treated with NaBH(OAc)$_3$ (1.64 g, 8.0 mmol). The reaction mixture was stirred at room temperature for overnight and decomposed with water. The reaction mixture was concentrated under reduced pressure to give a residue. The residue was purified by biotage over silica gel to afford di-tert-butyl 2,2'-((2-(2-(((4-sulfamoylphenethyl)amino)methyl)-1H-imidazol-1-yl)acetyl)azanediyl)diacetate as a white solid (547 mg, 24%). $^1$H NMR (400 MHz, DMSO-d$_6$) 7.68 (d, J=8.0 Hz, 2H), 7.32 (d, J=8.0 Hz, 2H), 7.24 (s, 2H), 6.94 (s, 1H), 6.72 (s, 1H), 4.95 (s, 2H), 4.25 (s, 2H), 3.95 (s, 2H), 3.61 (s, 2H), 2.70-2.67 (m, 4H), 1.43 (s, 9H), 1.35 (s, 9H); MS (ESI), 566.2 (M+H)$^+$.

Step 2. di-tert-butyl 4-(2-(2-((((1-(2-(bis(2-(tert-bu-toxy)-2-oxoethyl)amino)-2-oxoethyl)-1H-imidazol-2-yl)methyl)(4-sulfamoylphenethyl)amino)methyl)-1H-imidazol-1-yl)acetamido)-4-(3-(tert-butoxy)-3-oxopropyl)heptanedioate

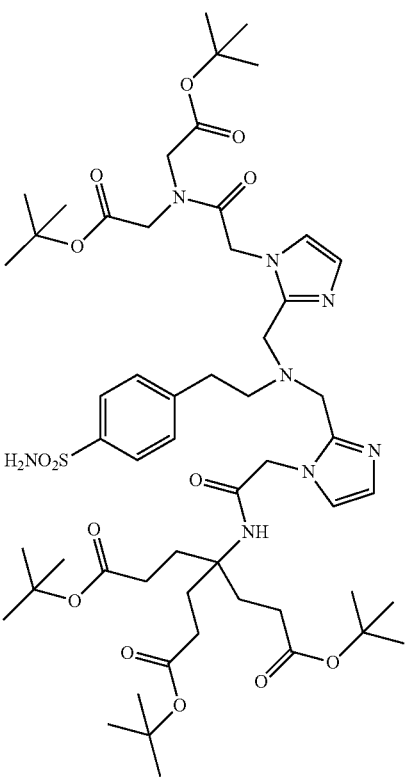 [SMILES: CC(C)(C)OC(=O)CCC(CCC(=O)OC(C)(C)C)(CCC(=O)OC(C)(C)C)NC(=O)Cn1ccnc1CN(CCc1ccc(S(N)(=O)=O)cc1)Cc1nccn1CC(=O)N(CC(=O)OC(C)(C)C)CC(=O)OC(C)(C)C]

To a solution of di-tert-butyl 2,2'-((2-(2-(((4-sulfamoylphenethyl)amino)methyl)-1H-imidazol-1-yl)acetyl)azanediyl)diacetate (200 mg, 0.353 mmol), di-tert-butyl 4-(3-(tert-butoxy)-3-oxopropyl)-4-(2-(2-formyl-1H-imidazol-1-yl)acetamido)heptanedioate (195 mg, 0.353 mmol), AcOH (0.10 mL) in DCE (10 mL) at 0° C. was treated with NaBH(OAc)$_3$ (148 mg, 0.70 mmol). The reaction mixture was stirred at 0° C. for 30 minutes and at room temperature for overnight and decomposed with water. The reaction mixture was concentrated under reduced pressure to give a residue. The residue was purified by biotage over silica gel to afford di-tert-butyl 4-(2-(2-((((1-(2-(bis(2-(tert-butoxy)-2-oxoethyl)amino)-2-oxoethyl)-1H-imidazol-2-yl)methyl)(4-sulfamoylphenethyl)amino)methyl)-1H-imidazol-1-yl)acetamido)-4-(3-(tert-butoxy)-3-oxopropyl)heptanedioate (237 mg, 61%). $^1$H NMR (400 MHz, DMSO-d$_6$) 7.76 (s, 1H), 7.66 (d, J=8.4 Hz, 1H), 7.23 (d, J=8.4 Hz, 2H), 7.22 (s, 2H), 7.01 (d, J=1.2 Hz, 1H), 6.99 (d, J=1.6 Hz, 2H), 6.83 (d, J=0.8 Hz, 1H), 6.80 (d, J=0.8 Hz, 1H), 5.02 (s, 2H), 4.55 (s, 2H), 4.31 (s, 2H), 3.97 (s, 2H), 3.63 (s, 2H), 3.60 (s, 2H), 2.77-2.73 (m, 2H), 2.66-2.60 (m, 2H), 2.10 (t, J=8.2 Hz, 6H), 1.78 (t, J=8.2 Hz, 6H), 1.36 (s, 45H); MS (ESI), 551.4 (M/2+H)$^+$.

Step 3. [Re(CO)$_3$][4-(2-(2-((((1-(2-(bis(carboxymethyl)amino)-2-oxoethyl)-1H-imidazol-2-yl)methyl)(4-sulfamoylphenethyl)amino)methyl)-1H-imidazol-1-yl)acetamido)-4-(2-carboxyethyl)heptanedioic acid] (Re-(9))

A solution of di-tert-butyl 4-(2-(2-((((1-(2-(bis(2-(tert-butoxy)-2-oxoethyl)amino)-2-oxoethyl)-1H-imidazol-2-yl)methyl)(4-sulfamoylphenethyl)amino)methyl)-1H-imidazol-1-yl)acetamido)-4-(3-(tert-butoxy)-3-oxopropyl)heptanedioate (80 mg, 0.0726 mmol) and [NEt$_4$]$_2$[ReBr$_3$(CO)$_3$] (58 mg, 0.075 mmol) in CH$_3$CN (5.0 mL) was stirred at 85° C. for 4 hrs at a pressure tube. Solvent was evaporated under reduced pressure to give crude product. A solution of crude product in TFA (1.0 mL) and DCM (1.0 mL) was stirred at room temperature for 6 hrs. Solvent was removed under a steam of nitrogen to give a residue, which was purified by HPLC and lyophilized to give Re-(9) as a white solid (62.8 mg, 80%). $^1$H NMR (400 MHz, DMSO-d$_6$) 7.80 (d, J=8.4 Hz, 1H), 7.71 (s, 1H), 7.58 (d, J=8.4 Hz, 2H), 7.29 (s, 2H), 7.20 (d, J=1.6 Hz, 1H), 7.14 (d, J=1.2 Hz, 2H), 7.14-7.05 (m, 2H), 5.09 (s, 2H), 4.71 (s, 2H), 4.67-3.86 (m, 10H), 3.13-3.11 (m, 2H), 2.19 (t, J=8.2 Hz, 6H), 1.86 (t, J=8.2 Hz, 6H); MS (ESI), 1091.1 (M+H)$^+$.

Example 4

[Re(CO)$_3$][4,4'-((2,2'-(2,2'-(((4-(4-sulfamoylphenoxy)butyl)azanediyl)bis(methylene))bis(1H-imidazole-2,1-diyl))bis(acetyl))bis(azanediyl))bis(4-(2-carboxyethyl)heptanedioic acid)] (Re-(13))

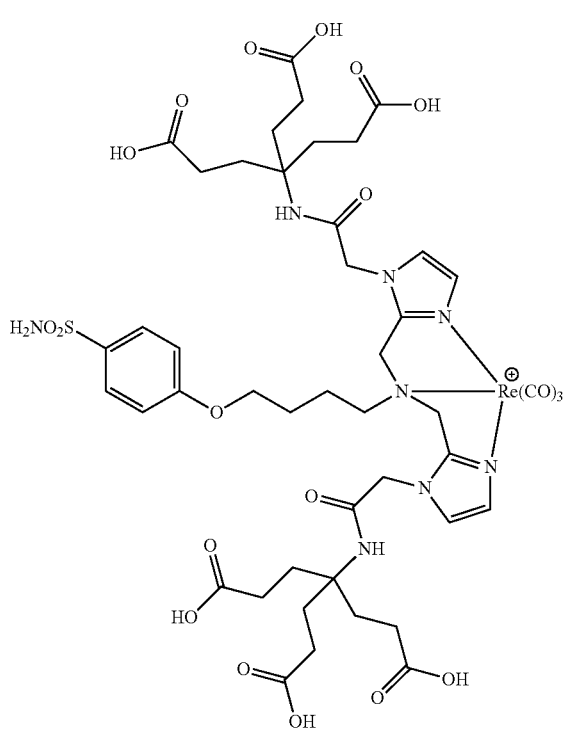

Step 1. tetra-tert-butyl 4,4'-((2,2'-(2,2'-(((4-(4-sulfamoylphenoxy)butyl)azanediyl)bis(methylene))bis(1H-imidazole-2,1-diyl))bis(acetyl))bis(azanediyl))bis(4-(3-(tert-butoxy)-3-oxopropyl)heptanedioate

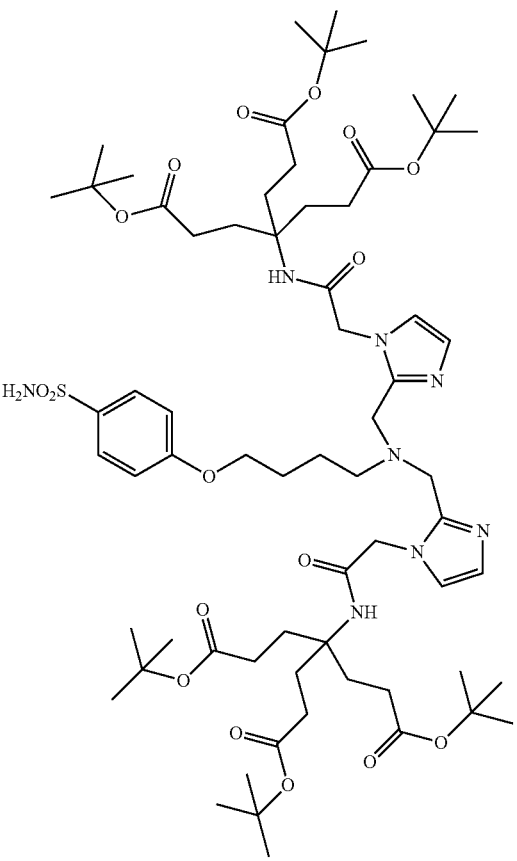 [SMILES: CC(C)(C)OC(=O)CCC(CCC(=O)OC(C)(C)C)(CCC(=O)OC(C)(C)C)NC(=O)Cn1ccnc1CN(CCCCOc1ccc(S(N)(=O)=O)cc1)Cc1nccn1CC(=O)NC(CCC(=O)OC(C)(C)C)(CCC(=O)OC(C)(C)C)CCC(=O)OC(C)(C)C]

A solution of 4-(4-aminobutoxy)benzenesulfonamide TFA salt (216 mg, 0.59 mmol) and di-tert-butyl 4-(3-(tert-butoxy)-3-oxopropyl)-4-(2-(2-formyl-1H-imidazol-1-yl)acetamido)heptanedioate (570 mg, 1.033 mmol) in DCE (20 mL) was stirred at 75° C. for 30 min under nitrogen. The reaction mixture was cooled to 0° C., and treated with NaBH(OAc)$_3$ (0.395 g). The reaction mixture was stirred at room temperature for overnight and decomposed with water. The reaction mixture was concentrated under reduced pressure to give a residue. The residue was purified by biotage over silica gel to afford tetra-tert-butyl 4,4'-((2,2'-(2,2'-(((4-(4-sulfamoylphenoxy)butyl)azanediyl)bis(methylene))bis(1H-imidazole-2,1-diyl))bis(acetyl))bis(azanediyl))bis(4-(3-(tert-butoxy)-3-oxopropyl)heptanedioate (186 mg). MS (ESI), 658.4 (M/2+H)$^+$.

Step 2. [Re(CO)$_3$][4,4'-((2,2'-(2,2'-(((4-(4-sulfamoylphenoxy)butyl)azanediyl)bis(methylene))bis(1H-imidazole-2,1-diyl))bis(acetyl))bis(azanediyl))bis(4-(2-carboxyethyl)heptanedioic acid)] (Re-(13))

A solution of tetra-tert-butyl 4,4'-((2,2'-(2,2'-(((4-(4-sulfamoylphenoxy)butyl)azanediyl)bis(methylene))bis(1H-imidazole-2,1-diyl))bis(acetyl))bis(azanediyl))bis(4-(3-(tert-butoxy)-3-oxopropyl)heptanedioate (114 mg, 0.0867 mmol) and [NEt$_4$]$_2$[ReBr$_3$(CO)$_3$] (66.8 mg, 0.0867 mmol) in acetonitrile (5.0 mL) was stirred at 95° C. for 5 hrs at a pressure tube. Solvent was evaporated under reduce pressure to give crude product. A solution of crude product in TFA (1.0 mL) and DCM (1.0 mL) was stirred at room temperature for overnight. Solvent was removed under a stream of nitrogen to give a residue, which was purified by HPLC and lyophilized to give Re-(13) as a white solid (57.7 mg, 53%). $^1$H NMR (400 MHz, DMSO-d$_6$) 12.11 (brs, 6H), 7.73 (d, J=8.8 Hz, 2H), 7.71 (s, 2H), 7.18 (s, 2H), 7.16 (d, J=1.6 Hz, 2H), 7.06 (d, J=9.2 Hz, 2H), 7.03 (d, J=1.6 Hz, 2H), 4.72 (d, J=17.6 Hz, 2H), 4.67 (d, J=16.8 Hz, 2H), 4.35 (d, J=16.4 Hz, 2H), 4.36 (d, J=16.4 Hz, 2H), 4.09 (t, J=6.0 Hz, 2H), 3.78-3.70 (m, 2H), 2.13 (t, J=7.8 Hz, 12H), 1.84 (t, J=7.8 Hz, 12H); MS (ESI), 1249 M$^+$.

Example 5

[Re(CO)$_3$][4,4'-((2,2'-(2,2'-(((3-(4-sulfamoylphenyl)propyl)azanediyl)bis(methylene))bis(1H-imidazole-2,1-diyl))bis(acetyl))bis(azanediyl))bis(4-(2-carboxyethyl)heptanedioic acid))] (Re-(14))

Step 1. tetra-tert-butyl 4,4'-((2,2'-(2,2'-(((3-(4-sulfamoylphenyl)propyl)azanediyl)bis(methylene))bis(1H-imidazole-2,1-diyl))bis(acetyl))bis(azanediyl))bis(4-(3-(tert-butoxy)-3-oxopropyl)heptanedioate A solution of 4-(3-aminopropyl)benzenesulfonamide HCl salt (201 mg, 0.80 mmol), di-tert-butyl 4-(3-(tert-butoxy)-3-oxopropyl)-4-(2-(2-formyl-1H-imidazol-1-yl)acetamido)heptanedioate (883 mg, 1.60 mmol) and AcOH (0.05 mL) in DCE (20 mL) was stirred at 75° C. for 30 min under nitrogen. The reaction mixture was cooled to 0° C., and treated with NaBH(OAc)$_3$ (0.395 g). The reaction mixture was stirred at 0° C. for 1 h and at room temperature for overnight and decomposed with water. The reaction mixture was concentrated under reduced pressure to give a residue. The residue was purified by biotage over silica gel to afford the desired product (648 mg). MS (ESI), 643.4 (M/2+H)⁺.

Step 2. [Re(CO)₃][4,4'-((2,2'-(2,2'-(((3-(4-sulfamoylphenyl)propyl)azanediyl)bis(methylene))bis(1H-imidazole-2,1-diyl))bis(acetyl))bis(azanediyl))bis(4-(2-carboxyethyl)heptanedioic acid)] (Re-(14))

A solution of tetra-tert-butyl 4,4'-((2,2'-((2,2'-(((3-(4-sulfamoylphenyl)propyl)azanediyl)bis(methylene))bis(1H-imidazole-2,1-diyl))bis(acetyl))bis(azanediyl))bis(4-(3-(tert-butoxy)-3-oxopropyl)heptanedioate (198 mg, 0.154 mmol) and [NEt₄]₂[ReBr₃(CO)₃] (118 mg, 0.154 mmol) in acetonitrile (5.0 mL) was stirred at 95° C. for 5 hrs at a pressure tube. Solvent was evaporated under reduce pressure to give crude product. A solution of crude product in TFA (1.0 mL) and DCM (1.0 mL) was stirred at room temperature for overnight. Solvent was removed under a stream of nitrogen to give a residue, which was purified by biotage SP4 using KP-C18-HS Cartridge and lyophilized to give Re-(14) as a white solid (91 mg). ¹H NMR (400 MHz, DMSO-d₆) 12.13 (brs, 6H), 7.75 (d, J=8.4 Hz, 2H), 7.70 (s, 2H), 7.43 (d, J=8.4 Hz, 2H), 7.27 (s, 2H), 7.16 (d, J=1.2 Hz, 2H), 7.02 (d, J=1.2 Hz, 2H), 4.70 (d, J=17.6, 2H), 4.64 (d, J=16.8, 2H), 4.48 (d, J=16.4 Hz, 2H), 4.35 (d, J=16.4 Hz, 2H), 3.72-3.70 (m, 2H), 2.74-2.69 (m, 2H), 2.16-2.06 (m, 14H), 1.86-1.83 (m, 12H); MS (ESI), 1219 M⁺.

Example 6

[Re(CO)₃][4,4'-((2,2'-(2,2'-(((6-(4-sulfamoylphenoxy)hexyl)azanediyl)bis(methylene))bis(1H-imidazole-2,1-diyl))bis(acetyl))bis(azanediyl))bis(4-(2-carboxyethyl)heptanedioic acid)] (Re-(15))

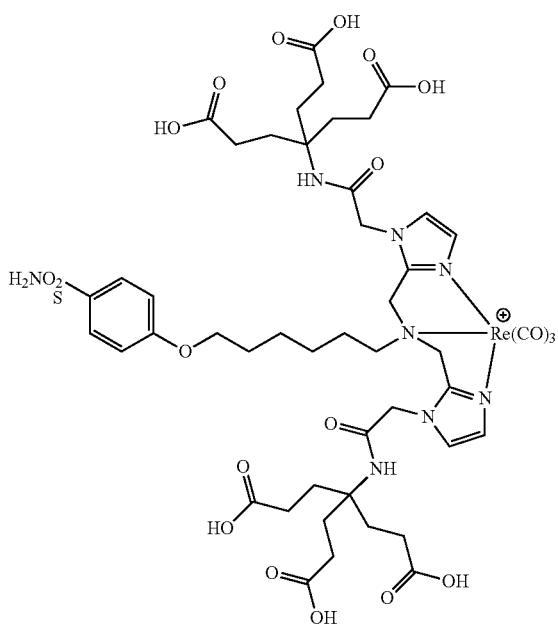

Step 1.
tert-butyl(6-(4-sulfamoylphenoxy)hexyl)carbamate

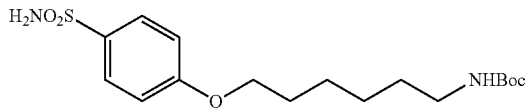 [SMILES: CC(C)(C)OC(=O)NCCCCCCOc1ccc(S(N)(=O)=O)cc1]

To a solution of 4-hydroxybenzenesulfonamide (1.73 g, 10.0 mmol) and tert-butyl(6-bromohexyl)carbamate (2.1 g, 7.5 mmol) in acetonitrile (50 mL) was added anhydrous K₂CO₃ (2.07 g, 15 mmol). The reaction mixtures were stirred at 75° C. for overnight. Solvent was evaporated under reduced pressure to give a residue. The residue was diluted with 1 N HCl (40 mL), extracted with DCM, and dried over Na₂SO₄. Solvent was evaporated under reduce pressure to afford a residue, which was purified by biotage eluting with DCM to 10% MeOH in DCM to afford tert-butyl(6-(4-sulfamoylphenoxy)hexyl)carbamate (1.192 g, 43%).

Step 2. 4-((6-aminohexyl)oxy)benzenesulfonamide

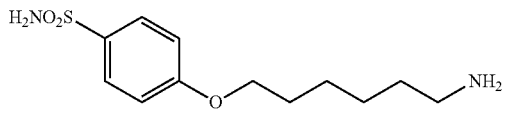 [SMILES: NCCCCCCOc1ccc(S(N)(=O)=O)cc1]

A solution of tert-butyl(6-(4-sulfamoylphenoxy)hexyl)carbamate (1.178 g, 3.16 mmol) in TFA (5.0 mL) and DCM (5.0 mL) was stirred at rt for overnight. After the solvent was evaporated under a steam of N₂, the reaction mixture was dissolved in water (5.0 mL) and acetonitrile (5.0 mL) and lyophilized to afford 4-((6-aminohexyl)oxy)benzenesulfonamide (1.664 g) containing TFA. MS (ESI), 273.1 (M+H)⁺.

Step 3. tetra-tert-butyl 4,4'-((2,2'-(2,2'-(((6-(4-sulfamoylphenoxy)hexyl)azanediyl)bis(methylene))bis(1H-imidazole-2,1-diyl))bis(acetyl))bis(azanediyl))bis(4-(3-(tert-butoxy)-3-oxopropyl)heptanedioate A solution of 4-((6-aminohexyl)oxy)benzenesulfonamide (1.664 g) containing TFA (346 mg, 0.659 mmol), di-tert-butyl 4-(3-(tert-butoxy)-3-oxopropyl)-4-(2-(2-formyl-1H-imidazol-1-yl)acetamido)heptanedioate (727 mg, 1.32 mmol) and AcOH (0.05 mL) in DCE (50 mL) was stirred at 75° C. for 30 min under nitrogen. The reaction mixture was cooled to 0° C., and treated with NaBH(OAc)₃ (0.422 g). The reaction mixture was stirred at room temperature for overnight and decomposed with water. The reaction mixture was concentrated under reduced pressure to give a residue. The residue was purified by biotage over silica gel to afford the desired product (153 mg). MS (ESI), 672.4 (M/2+H)⁺.

Step 4. [Re(CO)₃][4,4'-((2,2'-(2,2'-(((6-(4-sulfamoylphenoxy)hexyl)azanediyl)bis(methylene))bis(1H-imidazole-2,1-diyl))bis(acetyl))bis(azanediyl))bis(4-(2-carboxyethyl)heptanedioic acid)] (Re-(15))

A solution of tetra-tert-butyl 4,4'-((2,2'-(2,2'-(((6-(4-sulfamoylphenoxy)hexyl)azanediyl)bis(methylene))bis(1H-imidazole-2,1-diyl))bis(acetyl))bis(azanediyl))bis(4-(3-(tert-butoxy)-3-oxopropyl)heptanedioate (81 mg, 0.060 mmol) and [NEt₄]₂[ReBr₃(CO)₃] (47 mg, 0.060 mmol) in acetonitrile (5.0 mL) was stirred at 95° C. for 4 hrs at a pressure tube. Solvent was evaporated under reduce pressure to give crude product. A solution of crude product in TFA (1.0 mL) and DCM (1.0 mL) was stirred at room temperature for overnight. Solvent was removed under a stream of nitrogen to give a residue, which was purified by Biotage using C18 Cartridge and lyophilized to give MIP-1506 as a white solid (12.2 mg). MS (ESI), 1277.1 M⁺.

Example 7

[Re(CO)₃][2,2',2",2"',2",2",2,2"'-((2,2',2",2"-(((2,2'-(((4-sulfamoylphenethyl)azanediyl)bis(methylene))bis(1H-imidazole-2,1-diyl))bis(propane-3,1-diyl))bis(azanetriyl))tetrakis(acetyl))tetrakis(azanetriyl))-octaacetic acid] (Re-(16))

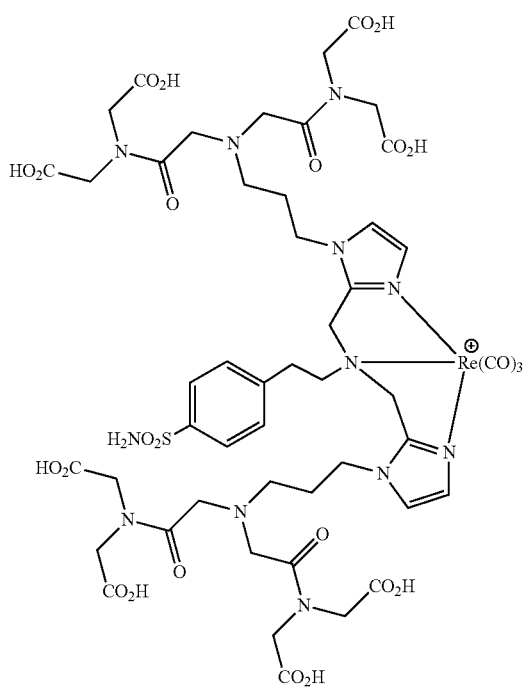

Step 1. tetra-tert-butyl 2,2',2",2"'-((2,2'((3-hydroxypropyl)azanediyl)bis(acetyl))bis(azanetriyl))tetraacetate

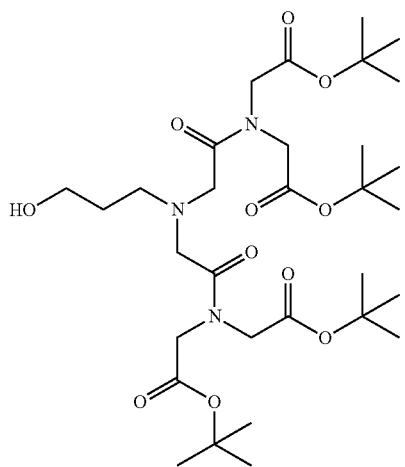 [SMILES: CC(C)(C)OC(=O)CN(CC(=O)OC(C)(C)C)C(=O)CN(CCCO)CC(=O)N(CC(=O)OC(C)(C)C)CC(=O)OC(C)(C)C]

To a solution of 3-aminopropan-1-ol (0.702 g, 9.35 mmol) and di-tert-butyl bromoacetyl)azanediyl)diacetate (6.847 g, 18.70 mmol) in acetonitrile (150 mL) was added DIPEA (15 mL). The reaction mixtures were stirred at it for 6 hrs. Solvent was evaporated under reduced pressure to give a residue, which was purified by biotage SP4 eluting with DCM to 5% MeOH in DCM to afford tetra-tert-butyl 2,2',2",2",2"'-((2,2'-((3-hydroxypropyl)azanediyl)bis(acetyl))bis(azanetriyl))tetraacetate (5.10 g, 85%). MS (ESI), 646 (M+H)⁺.

Step 2. tetra-tert-butyl 2,2',2",2"'-((2,2'-((3-(tosyloxy)propyl)azanediyl)bis(acetyl))bis(azanetriyl))tetraacetate

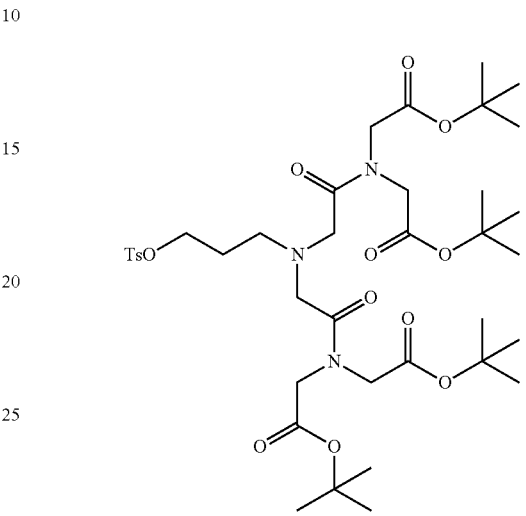

To a solution of tetra-tert-butyl 2,2',2",2",2"'-((2,2'((3-hydroxypropyl)azanediyl)bis(acetyl))bis(azanetriyl))tetraacetate (5.00 g, 7.75 mmol), Et₃N (20 mL) and trimethylamine HCl salt (74 mg, 0.78 mmol) in acetonitrile (60 mL) was added TsCl (1.625 g, 8.52 mmol) at 0° C. The reaction mixture was stirred at 0° C. for 1 h and at it for 1 h. After the solvent was evaporated, the reaction mixture was added sat. sodium bicarbonate (50 mL) and extracted with EtOAc (3×). Solvent was evaporated under reduced pressure to give a residue, which was purified by biotage SP4 eluting with 10% EtOAc in hexane to EtOAc to afford tetra-tert-butyl 2,2',2",2"',2"'-((2,2'-(3-(tosyloxy)propyl)azanediyl)bis(acetyl))bis(azanetriyl))tetraacetate (5.6624 g, 91%). MS (ESI), 800.4 (M+H)⁺.

Step 3. tetra-tert-butyl 2,2',2",2"'-((2,2'-((3-(2-formyl-1H-imidazol-1-yl)propyl)azanediyl)bis(acetyl))bis(azanetriyl))tetraacetate

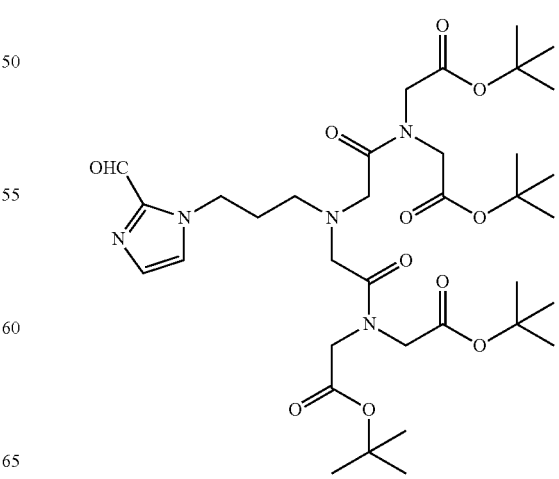

A solution of tetra-tert-butyl 2,2',2",2'"-((2,2'-((3-(tosyloxy)propyl)azanediyl)bis(acetyl))bis(azanetriyl))tetraacetate (1.6224 g, 2.028 mmol), 1H-imidazole-2-carbaldehyde (0.1948 g, 2.028 mmol), DIPEA (1.0 mL), and KI (0.066 g) in DMF (10 mL) was stirred at 75° C. for 6 hrs. The solvent was evaporated under reduced pressure to afford a residue, which was purified by biotage eluting with DCM to 10% MeOH in DCM to give tetra-tert-butyl 2,2',2",2'"-((2,2'-((3-(2-formyl-1H-imidazol-1-yl)propyl)azanediyl)bis(acetyl))bis(azanetriyl))tetraacetate (0.65 g, 44%). MS (ESI), 724.4 (M+H)⁺.

Step 4. octa-tert-butyl 2,2',2",2'",2"",2""',2""",2"""",2"""""-((2,2',2",2'"-(((2,2'-(((4-sulfamoylphenethyl)azanediyl)bis(methylene))bis(1H-imidazole-2,1-diyl))-bis(propane-3,1-diyl))bis(azanetriyl))tetrakis(acetyl))tetrakis(azanetriyl))-octaacetate

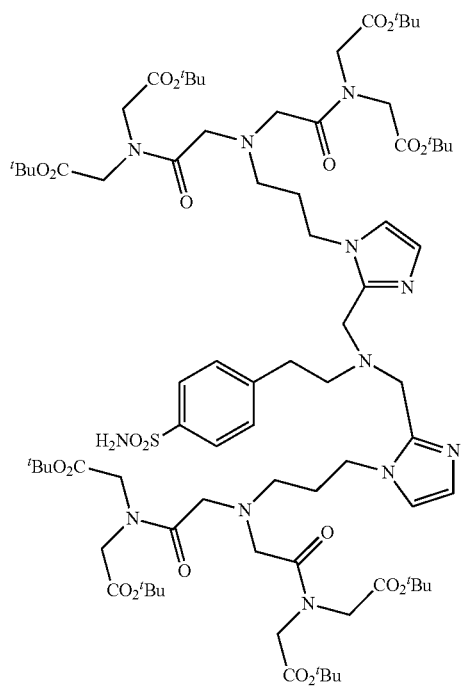 [SMILES: CC(C)(C)OC(=O)CN(CC(=O)OC(C)(C)C)C(=O)CN(CCCn1ccnc1CN(CCc1ccc(S(N)(=O)=O)cc1)Cc1nccn1CCCN(CC(=O)N(CC(=O)OC(C)(C)C)CC(=O)OC(C)(C)C)CC(=O)N(CC(=O)OC(C)(C)C)CC(=O)OC(C)(C)C)CC(=O)N(CC(=O)OC(C)(C)C)CC(=O)OC(C)(C)C]

A solution of 4-(2-aminoethyl)benzenesulfonamide (88 mg, 0.44 mmol), AcOH (0.10 mL) and tetra-tert-butyl 2,2',2",2'"-((2,2'-((3-(2-formyl-1H-imidazol-1-yl)propyl)azanediyl)bis(acetyl))bis(azanetriyl))tetraacetate (640 mg, 0.88 mmol) in DCE (20 mL) was stirred at 80° C. for 30 min under nitrogen. The reaction mixture was cooled to 0° C., and treated with NaBH(OAc)₃ (0.254 g, 1.2 mmol). The reaction mixture was stirred at room temperature for overnight and decomposed with water. The reaction mixture was extracted with DCM. The organic layer was dried and concentrated under reduced pressure. The residue was purified by biotage over silica gel to afford the desired product (237 mg). MS (ESI), 808.5 (M/2+H)⁺.

Step 5. [Re(CO)₃][2,2',2",2'",2"",2""',2""",2"""",2"""""-((2,2',2",2'"-(((2,2'-(((4-sulfamoylphenethyl)azanediyl)bis(methylene))bis(1H-imidazole-2,1-diyl))bis(propane-3,1-diyl))bis(azanetriyl))tetrakis(acetyl))tetrakis(azanetriyl))-octaacetic acid] (Re-(16))

A solution of octa-tert-butyl 2,2',2",2'",2"",2""',2""",2"""",2"""""-((2,2',2",2'"-(((2,2'-((((4-sulfamoylphenethyl)azanediyl)bis(methylene))bis(1H-imidazole-2,1-diyl))-bis(propane-3,1-diyl))bis(azanetriyl))tetrakis(acetyl))tetrakis(azanetriyl))-octaacetate (70 mg, 0.0433 mmol) and [NEt₄]₂[ReBr₃(CO)₃] (34 mg, 0.0433 mmol) in acetonitrile (5.0 mL) was stirred at 90° C. for 4 hrs at a pressure tube. Solvent was evaporated under reduce pressure to give crude product. A solution of crude product in TFA (1.0 mL) and DCM (1.0 mL) was stirred at room temperature for overnight. Solvent was removed under a stream of nitrogen to give a residue, which was purified by biotage using C18 Cartridge and lyophilized to give Re-(16) as a white solid (14.0 mg). MS (ESI), 719.2 (M+H)/2⁺.

Example 8

[Re(CO)₃][4-(2-(2-(((((1H-imidazol-2-yl)methyl)(4-sulfamoylphenethyl)amino)methyl)-1H-imidazol-1-yl)acetamido)-4-(2-carboxyethyl)heptanedioic acid] (Re-(17))

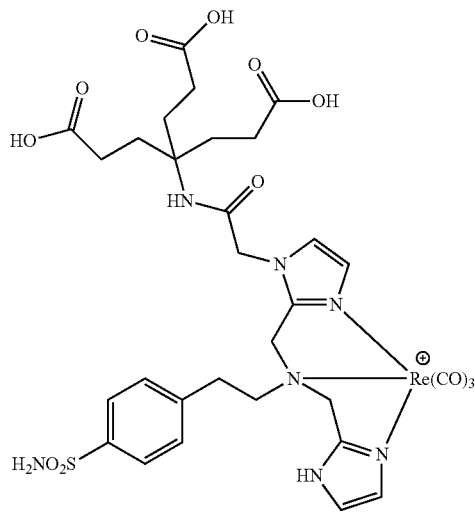

A solution of di-tert-butyl 4-(2-(2-(((((1H-imidazol-2-yl)methyl)(4-sulfamoylphenethyl)amino)methyl)-1H-imidazol-1-yl)acetamido)-4-(3-(tert-butoxy)-3-oxopropyl)heptanedioate (250 mg) and [NEt₄]₂[ReBr₃(CO)₃] (154 mg) in acetonitrile (6.0 mL) was stirred at 95° C. for 4 hrs at a pressure tube. Solvent was evaporated under reduce pressure to give crude product. A solution of crude product in TFA (2.0 mL) and DCM (3.0 mL) was stirred at room temperature for overnight. Solvent was removed under a stream of nitrogen to give a residue, which was purified by biotage using C18 Cartridge and lyophilized to give Re-(17) as a white solid (97.7 mg). ¹H NMR (400 MHz, DMSO-d₆) 13.06 (s, 1H), 12.12 (brs, 3H), 7.80 (d, J=8.4 Hz, 2H), 7.76 (s, 1H), 7.57 (d, J=8.4 Hz, 2H), 7.29 (s, 2H), 7.24-7.07 (m, 2H), 7.07-7.05 (m, 2H), 4.95-4.48 (m, 6H), 3.86 (d, J=8.4 Hz, 2H), 3.21-3.08 (m, 2H), 2.16 (t, J=8.0 Hz, 6H), 1.92-1.84 (m, 6H); MS (ESI), 918.0 M+.

Example 9

[Re(CO)₃][4-(2-(bis((1-(4-aminobutyl)-1H-1,2,3-triazol-4-yl)methyl)amino)ethyl)benzenesulfonamide] (Re-(8))

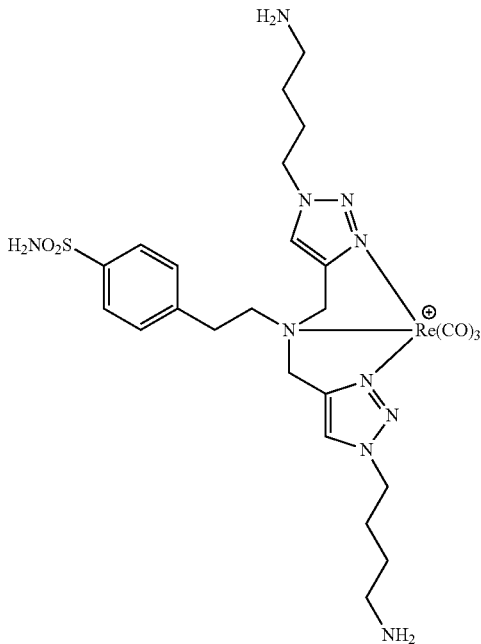

Step 1. 4-(2-(di(prop-2-yn-1-yl)amino)ethyl)benzenesulfonamide

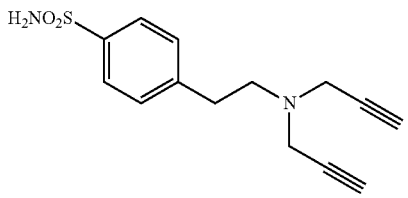 [SMILES: C#CCN(CC#C)CCc1ccc(S(N)(=O)=O)cc1]

To a solution of 4-(2-aminoethyl)benzenesulfonamide (2.00 g, 10 mmol), 3-bromoprop-1-yne (2.16 mL, 20 mmol, 80% in toluene) in acetonitrile (50 mL) was added DIPEA (3.0 mL). The reaction mixtures were stirred at room temperature for overnight and concentrated under reduced pressure to give a residue. The residue was purified by biotage over silica gel eluting with DCM to 10% MeOH in DCM to afford 4-(2-(di(prop-2-yn-1-yl)amino)ethyl)benzenesulfonamide as a yellow oil (2.40 g, 87%). MS (ESI), 277.1 (M+H)+.

Step 2. di-tert-butyl((4,4'-(((4-sulfamoylphenethyl)azanediyl)bis(methylene))bis(1H-1,2,3-triazole-4,1-diyl))bis(butane-4,1-diyl))dicarbamate

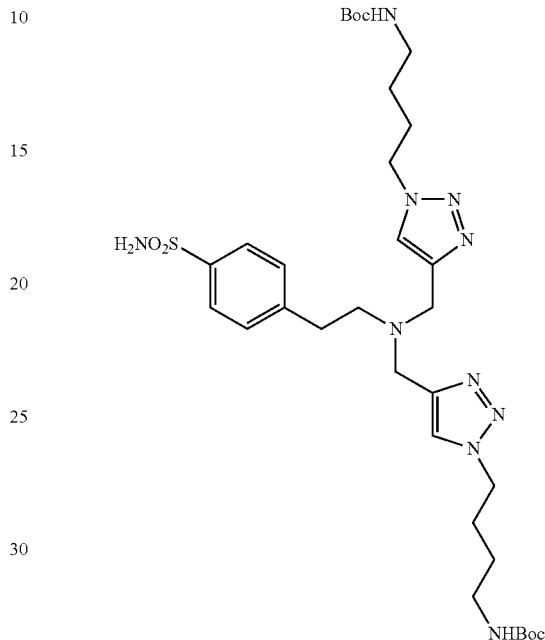

To a solution of 4-(2-(di(prop-2-yn-1-yl)amino)ethyl)benzenesulfonamide (0.155 g, 0.56 mmol), tert-butyl(4-azidobutyl)carbamate (0.458 g, 2.14 mmol) in THF (4.0 mL) and water (1.0 mL) was added Cu powder (64 mg, 1 mmol) and 1 N CuSO₄ (0.10 mL). The reaction mixtures were stirred at room temperature for overnight, dilute with DCM (50 mL) and washed with saturated EDTA solution. Solvent was evaporated under reduced pressure to give a residue, which was purified by biotage over silica gel eluting with DCM to 40% MeOH in DCM to afford di-tert-butyl((4,4'-(((4-sulfamoylphenethyl)azanediyl)bis(methylene))bis(1H-1,2,3-triazole-4,1-diyl))bis(butane-4,1-diyl))dicarbamate (0.176 g, 45%). MS (ESI), 705.3 (M+H)+.

Step 3. [Re(CO)₃][4-(2-(bis((1-(4-aminobutyl)-1H-1,2,3-triazol-4-yl)methyl)amino)ethyl)benzenesulfonamide] (Re-(8))

A solution of di-tert-butyl((4,4'-(((4-sulfamoylphenethyl)azanediyl)bis(methylene))bis(1H-1,2,3-triazole-4,1-diyl))bis(butane-4,1-diyl))dicarbamate (78 mg, 0.11 mmol) and [NEt₄]₂[ReBr₃(CO)₃] (100 mg, 0.129 mmol) in MeOH (3.0 mL) was stirred at 90° C. for 4 hrs under a pressure tube. Solvent was evaporated under reduced pressure to give crude product. A solution of crude product in TFA (2.0 mL) and DCM (2.0 mL) was stirred at room temperature for 3 hrs. Solvent was removed under reduced pressure to give a residue, which was purified by HPLC to give Re-(17) as a white solid (44.8 mg, 53%). ¹H NMR (400 MHz, DMSO-d₆) 8.33 (s, 2H), 7.82 (d, J=8.4 Hz, 2H), 7.78 (s, 4H), 7.60 (d, J=8.4 Hz, 2H), 7.32 (s, 2H), 4.82 (d, J=15.6 Hz, 2H), 4.67 (d, J=16.4 Hz, 2H), 4.41 (t, J=7.2 Hz, 4H), 3.98-3.94 (m, 2H), 3.26-3.22 (m, 2H), 2.81 (dd, J=12.0, 6.0 Hz, 4H), 1.85-1.78 (m, 4H), 1.50-1.44 (m, 4H); MS (ESI), 775.1 M⁻.

Example 10

[Re(CO)₃][2,2'-(4,4'-(((4-sulfamoylphenethyl)azanediyl)bis(methylene))bis(1H-1,2,3-triazole-4,1-diyl))diacetic acid] (Re-(10))

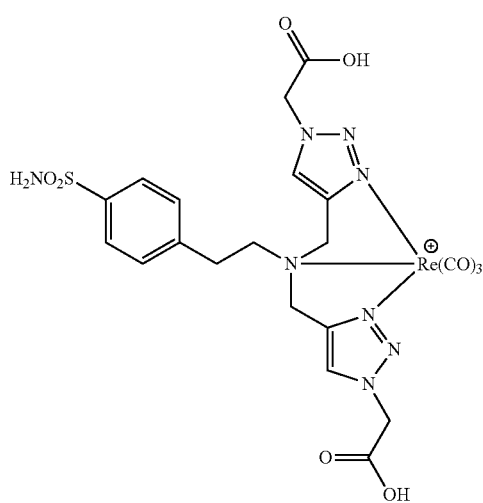

Step 1. di-tert-butyl 2,2'-(4,4'-(((4-sulfamoylphenethyl)azanediyl)bis(methylene))bis(1H-1,2,3-triazole-4,1-diyl))diacetate (MIP-1479)

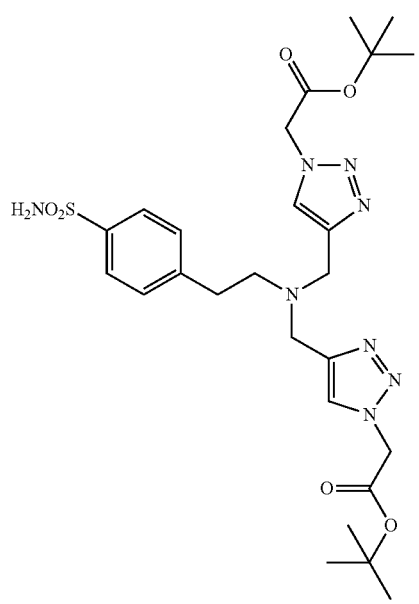 [SMILES: CC(C)(C)OC(=O)Cn1cc(CN(CCc2ccc(S(N)(=O)=O)cc2)Cc2cn(CC(=O)OC(C)(C)C)nn2)nn1]

To a solution of 4-(2-(di(prop-2-yn-1-yl)amino)ethyl)benzenesulfonamide (0.2272 g, 0.823 mmol), tert-butyl 2-azidoacetate (0.46 g, 3.292 mmol) in THF (8.0 mL) and water (2.0 mL) was added Cu powder (64 mg, 1 mmol) and 1 N CuSO₄ (0.20 mL). The reaction mixtures were stirred at room temperature for overnight, dilute with DCM (50 mL) and washed with saturated EDTA solution. Solvent was evaporated under reduced pressure to give a residue, which was purified by Biotage over silica gel eluting with DCM to 10% MeOH in DCM to afford di-tert-butyl 2,2'-(4,4'-(((4-sulfamoylphenethyl)azanediyl)bis(methylene))bis(1H-1,2,3-triazole-4,1-diyl))diacetate as a pale yellow solid (0.191 g, 39%). ¹H NMR (400 MHz, DMSO-d₆) 7.96 (s, 2H), 7.71 (d, J=8.4 Hz, 2H), 7.37 (d, J=8.4 Hz, 2H), 7.27 (s, 2H), 5.26 (s, 4H), 3.75 (s, 4H), 2.89 (t, J=7.6 Hz, 2H), 2.57 (d, J=7.4 Hz, 2H), 1.43 (s, 18H); MS (ESI), 591.2 (M+H)⁺.

Step 2. [Re(CO)₃][2,2'-(4,4'-(((4-sulfamoylphenethyl)azanediyl)bis(methylene))bis(1H-1,2,3-triazole-4,1-diyl))diacetic acid] (Re-(10))

A solution of di-tert-butyl 2,2'-(4,4'-(((4-sulfamoylphenethyl)azanediyl)bis(methylene))bis(1H-1,2,3-triazole-4,1-diyl))diacetate (46.4 mg, 0.078 mmol) and [NEt₄]₂[ReBr₃(CO)₃] (70 mg, 0.090 mmol) in CH₃CN (5.0 mL) was stirred at 95° C. for 2 hrs under a pressure tube. Solvent was evaporated under reduced pressure to give crude product. A solution of crude product in TFA (1.0 mL) and DCM (2.0 mL) was stirred at room temperature for 5 hrs. Solvent was removed under reduced pressure to give a residue, which was purified by HPLC to give Re-(10) as a white solid (52.8 mg, 90%). ¹H NMR (400 MHz, DMSO-d₆) 8.28 (s, 2H), 7.82 (d, J=8.4 Hz, 2H), 7.61 (d, J=8.4 Hz, 2H), 7.31 (s, 2H), 5.36 (d, J=17.2 Hz, 2H), 5.28 (d, J=17.2 Hz, 2H), 4.89 (d, J=16.0 Hz, 2H), 4.69 (d, J=16.0 Hz, 2H), 4.02-3.98 (m, 2H), 3.24-3.20 (m, 2H); MS (ESI), 749.0 M⁻.

Example 11

[Re(CO)₃][(2S,2'S)-2,2'-(4,4'-(((4-sulfamoylphenethyl)azanediyl)bis(methylene))bis(1H-1,2,3-triazole-4,1-diyl))dipentanedioic acid] (Re-(11))

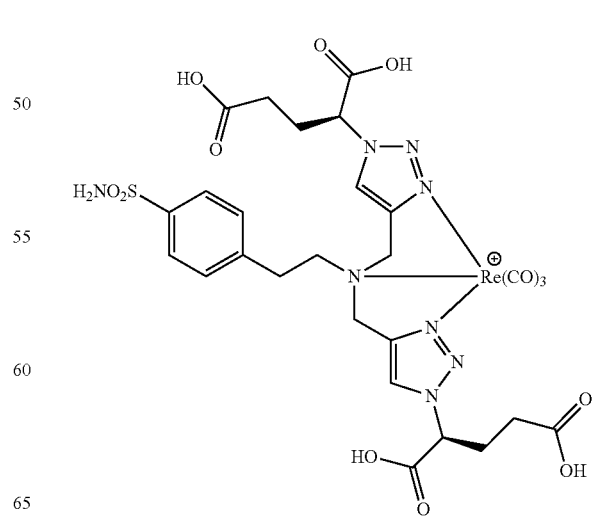

Step 1. (2S,2'S)-tetra-tert-butyl 2,2'-(4,4'-(((4-sulfamoylphenethyl)azanediyl)bis(methylene))bis(1H-1,2,3-triazole-4,1-diyl))dipentanedioate

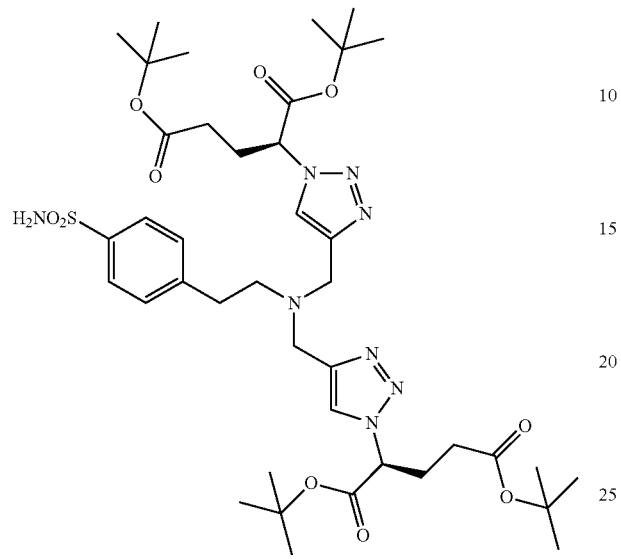

To a solution of 4-(2-(di(prop-2-yn-1-yl)amino)ethyl)benzenesulfonamide (0.112 g, 0.406 mmol), (S)-di-tert-butyl 2-azidopentanedioate (0.5895 g, 2.07 mmol) in THF (6.0 mL) and water (1.0 mL) was added Cu powder (64 mg, 1 mmol) and 1 N $CuSO_4$ (0.10 mL). The reaction mixtures were stirred at room temperature for 3 hrs, dilute with DCM (50 mL) and washed with saturated EDTA solution. Solvent was evaporated under reduced pressure to give a residue, which was purified by Biotage over silica gel eluting with DCM to 6% MeOH in DCM to afford (2S,2'S)-tetra-tert-butyl 2,2'-(4,4'-(((4-sulfamoylphenethyl)azanediyl)bis(methylene))bis(1H-1,2,3-triazole-4,1-diyl))dipentanedioate (0.226 g, 66%). $^1$H NMR (400 MHz, DMSO-$d_6$) 8.11 (s, 2H), 7.68 (d, J=8.4 Hz, 2H), 7.31 (d, J=8.4 Hz, 2H), 7.24 (s, 2H), 5.39 (dd, J=10.0, 5.2 Hz, 2H), 3.76 (s, 4H), 2.86 (t, J=7.4 Hz, 2H), 2.55 (d, J=7.4 Hz, 2H), 2.43-1.78 (m, 8H), 1.38 (s, 36H); MS (ESI), 847.3 $(M+H)^+$.

Step 2. [Re(CO)$_3$][(2S,2'S)-2,2'-(4,4'-(((4-sulfamoylphenethyl)azanediyl)bis(methylene))bis(1H-1,2,3-triazole-4,1-diyl))dipentanedioic acid] (Re-(11))

A solution of 2S,2'S)-tetra-tert-butyl 2,2'-(4,4'-(((4-sulfamoylphenethyl)azanediyl)bis(methylene))bis(1H-1,2,3-triazole-4,1-diyl))dipentanedioate (50 mg, 0.059 mmol) and [Na$_4$]$_2$[ReBr$_3$(CO)$_3$] (50 mg, 0.065 mmol) in CH$_3$CN (5.0 mL) was stirred at 85° C. for overnight under a pressure tube. Solvent was evaporated under reduced pressure to give crude product. A solution of crude product in TFA (2.0 mL) and DCM (2.0 mL) was stirred at room temperature for 4 hrs. Solvent was removed under reduced pressure to give a residue, which was purified by HPLC to give Re-(11) as an yellow solid (23.8 mg, 45%). $^1$H NMR (400 MHz, DMSO-$d_6$) 8.56 (s, 1H), 8.45 (s, 1H), 7.82 (d, J=8.4 Hz, 2H), 7.61 (d, J=8.0 Hz, 2H), 7.31 (s, 2H), 5.60-5.56 (m, 1H), 5.45-5.40 (m, 1H), 4.98-4.70 (m, 4H), 4.03-3.97 (m, 2H), 3.28-3.20 (m, 2H), 2.55-1.94 (m, 8H); MS (ESI), 893.0 M$^-$.

Example 12

[Re(CO)$_3$][2,2'-(2-(2-(((4-sulfamoylphenethyl)(thiazol-2-ylmethyl)amino)methyl)-1H-imidazol-1-yl)acetylazanediyl)diacetic acid] (Re-(17))

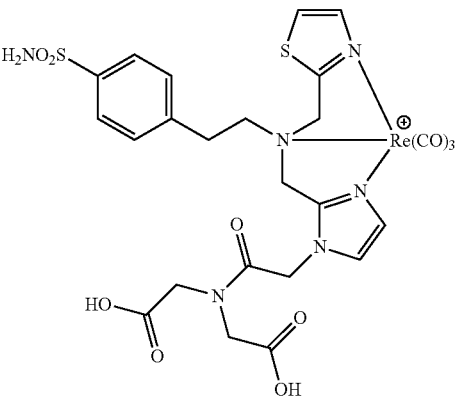

Step 1. di-tert-butyl 2,2'-((2-(2-(((4-sulfamoylphenethyl)amino)methyl)-1H-imidazol-1-yl)acetyl)azanediyl)diacetate

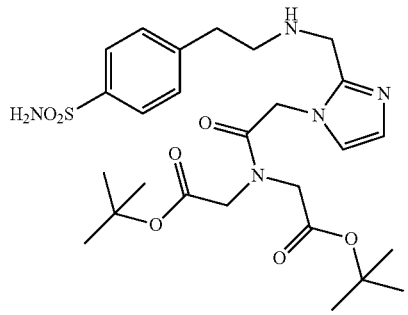 [SMILES: CC(C)(C)OC(=O)CN(CC(=O)OC(C)(C)C)C(=O)Cn1ccnc1CNCCc1ccc(S(N)(=O)=O)cc1]

A solution of 4-(4-aminobutoxy)benzenesulfonamide (2.40, 12.0 mmol), AcOH (0.40 mL) and tert-butyl 2,2'-(2-(2-formyl-1H-imidazol-1-yl)acetylazanediyl)diacetate (1.524 g, 4.0 mmol) in DCE (100 mL) was stirred at 75° C. for 30 min under nitrogen. The reaction mixture was cooled to 0° C., and treated with NaBH(OAc)$_3$ (1.64 g, 8.0 mmol). The reaction mixture was stirred at room temperature for overnight and decomposed with water. The reaction mixture was concentrated under reduced pressure to give a residue. The residue was purified by biotage over silica gel to afford di-tert-butyl 2,2'-((2-(2-(((4-sulfamoylphenethyl)amino)methyl)-1H-imidazol-1-yl)acetyl)azanediyl)diacetate as a white solid (547 mg, 24%). $^1$H NMR (400 MHz, DMSO-$d_6$) 7.68 (d, J=8.0 Hz, 2H), 7.32 (d, J=8.0 Hz, 2H), 7.24 (s, 2H), 6.94

(s, 1H), 6.72 (s, 1H), 4.95 (s, 2H), 4.25 (s, 2H), 3.95 (s, 2H), 3.61 (s, 2H), 2.70-2.67 (m, 4H), 1.43 (s, 9H), 1.35 (s, 9H); MS (ESI), 566.2 (M+H)+.

Step 2. di-tert-butyl 2,2'-((2-(2-(((4-sulfamoylphenethyl)(thiazol-2-ylmethyl)amino)methyl)-1H-imidazol-1-yl)acetyl)azanediyl)diacetate

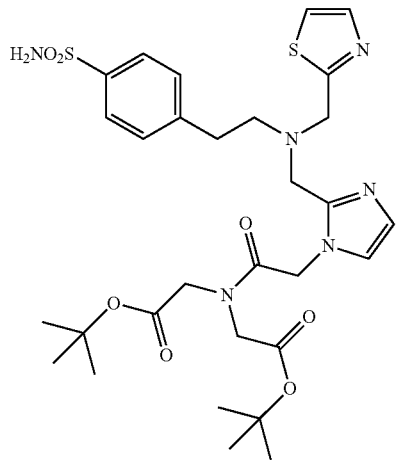 [SMILES: CC(C)(C)OC(=O)CN(CC(=O)OC(C)(C)C)C(=O)Cn1ccnc1CN(CCc1ccc(S(N)(=O)=O)cc1)Cc1nccs1]

To a solution of di-tert-butyl 2,2'-((2-(2-(((4-sulfamoylphenethyl)amino)methyl)-1H-imidazol-1-yl)acetyl)azanediyl)diacetate (244 mg, 0.43 mmol), thiazole-2-carbaldehyde (68 mg, 0.61 mmol), AcOH (0.05 mL) in DCE (10 mL) at 0° C. was treated with NaBH(OAc)$_3$ (212 mg, 1.0 mmol). The reaction mixture was stirred at room temperature for 2 hrs and decomposed with water. The reaction mixture was concentrated under reduced pressure to give a residue. The residue was purified by biotage over silica gel to afford di-tert-butyl 2,2'-((2-(2-(((4-sulfamoylphenethyl)(thiazol-2-ylmethyl)amino)methyl)-1H-imidazol-1-yl)acetyl)azanediyl)diacetate as a colorless oil (200 mg, 70%). MS (ESI), 663.3 (M+H)+.

Step 3. [Re(CO)$_3$][2,2'-(2-(2-(((4-sulfamoylphenethyl)(thiazol-2-ylmethyl)amino)methyl)-1H-imidazol-1-yl)acetylazanediyl)diacetic acid] (Re-(17))

A solution of di-tert-butyl 2,2'-(2-(2-(((4-sulfamoylphenethyl)(thiazol-2-ylmethyl)amino)methyl)-1H-imidazol-1-yl)acetyl)azanediyl)diacetate (50 mg, 0.0755 mmol) and [NEt$_4$]$_2$[ReBr$_3$(CO)$_3$] (60 mg, 0.078 mmol) in acetonitrile (5.0 mL) was stirred at 90° C. for 5 hrs at a pressure tube. Solvent was evaporated under reduce pressure to give crude product. A solution of crude product in TFA (0.50 mL) and DCM (0.50 mL) was stirred at room temperature for overnight. Solvent was removed under a stream of nitrogen to give a residue, which was purified by HPLC to give Re-(11) as a white solid (53.8 mg, 87%). $^1$H NMR (400 MHz, DMSO-d$_6$) 7.94 (d, J=3.6 Hz, 1H), 7.88 (d, J=3.2 Hz, 1H), 7.82 (d, J=8.0 Hz, 2H), 7.60 (d, J=8.0 Hz, 2H), 7.33 (s, 2H), 7.21 (d, J=1.2 Hz, 1H), 7.11 (d, J=1.6 Hz, 1H), 5.20-5.09 (m, 3H), 4.96 (d, J=17.2 Hz, 1H), 4.74 (d, J=16.4 Hz, 1H), 4.52 (d, J=16.4 Hz, 1H), 4.36 (d, J=18.8 Hz, 1H), 4.29 (d, J=19.2 Hz, 1H), 3.97-3.85 (m, 2H), 3.18-3.13 (m, 2H); MS (ESI), 821.1 M+.

Example 13

2,2'-((2-(2-((((1-(2-((3-iodophenyl)amino)-2-oxoethyl)-1H-imidazol-2-yl)methyl)(4-sulfamoylphenethyl)amino)methyl)-1H-imidazol-1-yl)acetyl)azanediyl)diacetic acid (18)

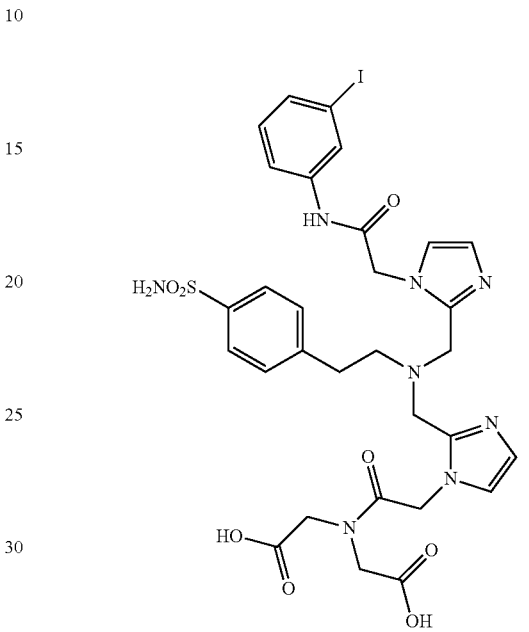

Step 1. 2-bromo-N-(3-iodophenyl)acetamide

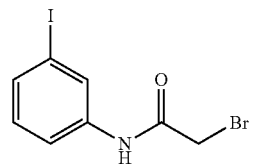 [SMILES: O=C(CBr)Nc1cccc(I)c1]

To a solution of 3-iodoaniline (2.19 g, 10.0 mmol) and 2-bromoacetyl bromide (0.87 mL, 3.40 g, 10.0 mmol) in DCM (100 mL) was added Et$_3$N (1.39 mL) at 0° C. The reaction mixtures were stirred at room temperature for overnight. The reaction mixtures were diluted with DCM (100 mL), washed with water, and dried over Na$_2$SO$_4$. Solvent was evaporated under reduce pressure to afford a residue, which was purified by biotage eluting with 10% EtOC in hexanes to 100% EtOAc to afford 2-bromo-N-(3-iodophenyl)acetamide (2.824 g, 83%). MS (ESI), 340, 342 (M+H)+.

Step 2. 2-(2-formyl-1H-imidazol-1-yl)-N-(3-iodophenyl)acetamide

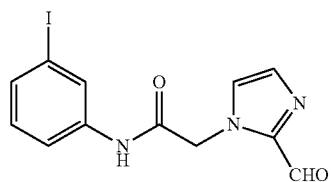 [SMILES: O=Cc1nccn1CC(=O)Nc1cccc(I)c1]

A solution of 2-bromo-N-(3-iodophenyl)acetamide (2.67 g, 7.83 mmol), 1H-imidazole-2-carbaldehyde (0.752 g, 7.83 mmol) and DIPEA (10 mL) in DMF (20 mL) was stirred at 80° C. for 4 hrs. The solvent was evaporated under reduced pressure to afford a residue, which was purified by Biotage eluting with DCM in hexanes to 10% MeOH in DCM to give 2-(2-formyl-1H-imidazol-1-yl)-N-(3-iodophenyl)acetamide (2.60 g, 94%). $^1$H NMR (400 MHz, DMSO) 9.64 (s, 1H), 8.17 (brs, 1H), 8.04 (s, 1H), 7.60 (s, 1H), 7.46 (d, J=8.4 Hz, 1H), 7.40 (d, J=8.0 Hz, 1H), 7.28 (s, 1H), 7.10 (t, J=8.0 Hz, 1H), 5.23 (s, 2H).

Step 3. di-tert-butyl 2,2'-((2-(2-((((1-(2-((3-iodophenyl)amino)-2-oxoethyl)-1H-imidazol-2-yl)methyl)(4-sulfamoylphenethyl)amino)methyl)-1H-imidazol-1-yl)acetyl)azanediyl)diacetate

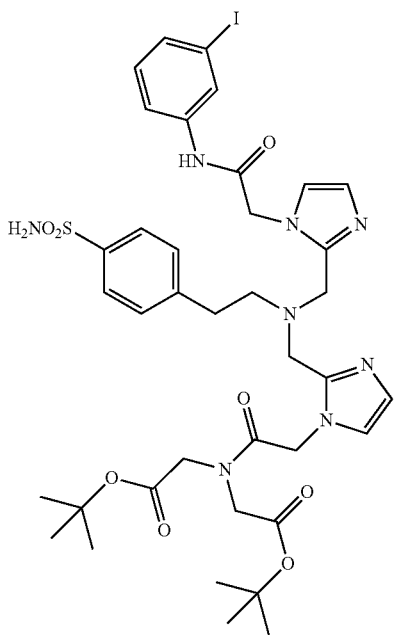 [SMILES: CC(C)(C)OC(=O)CN(CC(=O)OC(C)(C)C)C(=O)Cn1ccnc1CN(CCc1ccc(S(N)(=O)=O)cc1)Cc1nccn1CC(=O)Nc1cccc(I)c1]

To a solution of di-tert-butyl 2,2'-((2-(2-(((4-sulfamoylphenethyl)amino)methyl)-1H-imidazol-1-yl)acetyl)azanediyl)diacetate (283 mg, 0.50 mmol), AcOH (0.10 mL) and 2-(2-formyl-1H-imidazol-1-yl)-N-(3-iodophenyl)acetamide (178 mg, 0.50 mmol) in DCE (20 mL) at 0° C. was added NaBH(OAc)$_3$ (0.30 g, 1.5 mmol). The reaction mixture was stirred at 0° C. for 30 minutes and at room temperature for overnight and decomposed with water. The reaction mixture was extracted with DCM. The organic layer was dried and concentrated under reduced pressure. The residue was purified by biotage over silica gel eluting with DCM to 40% MeOH in DCM to afford di-tert-butyl 2,2'-((2-(2-((((1-(2-((3-iodophenyl)amino)-2-oxoethyl)-1H-imidazol-2-yl)methyl)(4-sulfamoylphenethyl)amino)methyl)-1H-imidazol-1-yl)acetyl)azanediyl)diacetate (254 mg, 56%).

Step 4. 2,2'-((2-(2-((((1-(2-((3-iodophenyl)amino)-2-oxoethyl)-1H-imidazol-2-yl)methyl)(4-sulfamoylphenethyl)amino)methyl)-1H-imidazol-1-yl)acetyl)azanediyl)diacetic acid (18)

A solution of di-tert-butyl 2,2'-((2-(2-((((1-(2-((3-iodophenyl)amino)-2-oxoethyl)-1H-imidazol-2-yl)methyl)(4-sulfamoylphenethyl)amino)methyl)-1H-imidazo 1-yl)acetyl)azanediyl)diacetate (45 mg, 0.0497 mmol) in DCM (1.0 mL) and TFA (1.0 mL) was stirred at room temperature for 5 hrs. Solvent was removed under a stream of nitrogen to give a residue, which was purified by HPLC to give compound (18) as a white solid (29 mg, 74%). $^1$H NMR (400 MHz, DMSO-d$_6$) 10.69 (s, 0.66H), 10.61 (s, 0.34; H), 8.10 (s, 0.66; H), 8.07 (s, 0.34; H), 7.69-7.62 (m, 3H), 7.54 (s, 1H), 7.48-7.44 (m, 2H), 7.27 (s, 2H), 7.30-7.26 (m, 3H), 7.13 (t, J=8.0 Hz, 1H), 5.31 (s, 1.32; H), 5.15 (s, 1.32; H), 5.12 (s, 0.68; H), 4.75 (s, 0.68; H), 4.33 (s, 2H), 4.16 (s, 2H), 4.05 (s, 4H), 2.72-2.68 (m, 4H); MS (ESI), 793.1 (M+H)$^-$.

Example 14

2,2'-(2-(2-(((4-iodobenzyl)(4-sulfamoylphenethyl)amino)methyl)-1H-imidazol-1-yl)acetylazanediyl)diacetic acid (19)

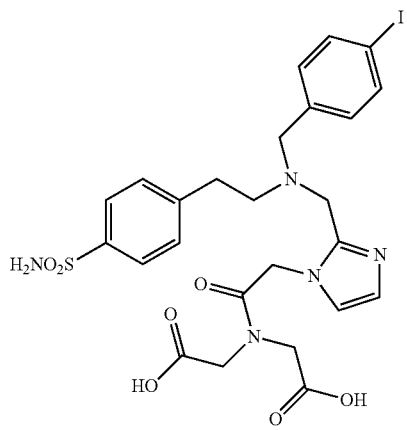 [SMILES: NS(=O)(=O)c1ccc(CCN(Cc2ccc(I)cc2)Cc2nccn2CC(=O)N(CC(=O)O)CC(=O)O)cc1]

Step 1.
4-(2-((4-iodobenzyl)amino)ethyl)benzenesulfonamide

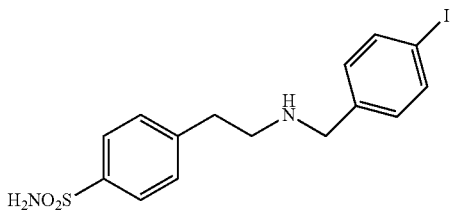 [SMILES: NS(=O)(=O)c1ccc(CCNCc2ccc(I)cc2)cc1]

A solution of 4-(4-aminobutoxy)benzenesulfonamide (2.84, 14.1 mmol), AcOH (1.0 mL) and 4-iodobenzaldehyde (1.09 g, 4.70 mmol) in DCE (100 mL) was stirred at 75° C. for 30 min under nitrogen. The reaction mixture was cooled to 0° C., and treated with NaBH(OAc)$_3$ (2.12 g, 10 mmol). The reaction mixture was stirred at 0° C. for 30 min. and at room temperature for overnight and decomposed with water. The reaction mixture was concentrated under reduced pressure to give a residue. The residue was purified by biotage over silica gel to afford 4-(2-((4-iodobenzyl)amino)ethyl)benzenesulfonamide as a white solid (533 mg, 27%). $^1$H NMR (400 MHz, DMSO-d$_6$) 7.68 (d, J=8.0 Hz, 2H), 7.62 (d, J=8.0 Hz, 2H), 7.35 (d, J=8.4 Hz, 2H), 7.25 (s, 2H), 7.09 (d, J=8.4 Hz, 2H), 3.63 (s, 2H), 2.76-2.65 (m, 4H); MS (ESI), 417.0 (M+H)+.

Step 2. di-tert-butyl 2,2'-((2-(2-(((4-iodobenzyl)(4-sulfamoylphenethyl)amino)methyl)-1H-imidazol-1-yl)acetyl)azanediyl)diacetate

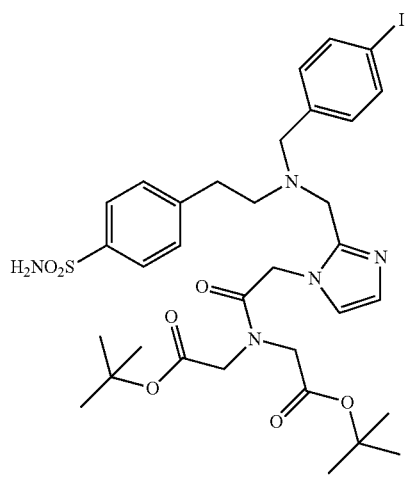 [SMILES: CC(C)(C)OC(=O)CN(CC(=O)OC(C)(C)C)C(=O)Cn1ccnc1CN(CCc1ccc(S(N)(=O)=O)cc1)Cc1ccc(I)cc1]

To a solution of 4-(2-((4-iodobenzyl)amino)ethyl)benzenesulfonamide (253 mg, 0.607 mmol), AcOH (0.10 mL) and tert-butyl 2,2'-(2-(2-formyl-1H-imidazol-1-yl)acetylazanediyl)diacetate (0.305 mg, 0.80 mmol) in DCE (10 mL) at 0° C. was added NaBH(OAc)₃ (0.30 g, 1.5 mmol). The reaction mixture was stirred at 0° C. for 30 minutes and at room temperature for overnight and decomposed with water. The reaction mixture was extracted with DCM. The organic layer was dried and concentrated under reduced pressure. The residue was purified by biotage over silica gel eluting with DCM to 10% MeOH in DCM to afford di-tert-butyl 2,2'-((2-(2-(((4-iodobenzyl)(4-sulfamoylphenethyl)amino)methyl)-1H-imidazol-1-yl)acetyl)azanediyl)diacetate (28.8 mg, 6.1%). MS (ESI), 782.2 (M+H)⁻.

Step 3. 2,2'-(2-(2-(((4-iodobenzyl)(4-sulfamoylphenethyl)amino)methyl)-1H-imidazol-1-yl)acetylazanediyl)diacetic acid (19)

A solution of di-tert-butyl 2,2'-((2-(2-(((4-iodobenzyl)(4-sulfamoylphenethyl)amino)methyl)-1H-imidazol-1-yl)acetyl)azanediyl)diacetate (28.8 mg, 0.0369 mmol) in DCM (0.50 mL) and TFA (0.5 mL) was stirred at room temperature for 5 hrs. Solvent was removed under a stream of nitrogen to give a residue, which was purified by HPLC to give compound (19) as a white solid (25.9 mg, 78.2%). ¹H NMR (400 MHz, DMSO-d₆) 7.70-7.66 (m, 4H), 7.57 (s, 1H), 7.55 (s, 1H), 7.29 (d, J=8.0 Hz, 2H), 7.28 (s, 2H), 7.17 (d, J=8.0 Hz, 2H), 5.26 (s, 2H), 4.34 (s, 2H), 4.06 (s, 2H), 3.91 (s, 2H), 3.69 (s, 2H), 2.82 (t, J=7.8 Hz, 2H), 2.59 (t, J=7.6 Hz, 2H); MS (ESI), 670.1 (M+H)⁻.

Example 15

2 2-(2-(((4-iodobenzyl)(4-sulfamoylphenethyl)amino)methyl)-1,1-imidazol-1-yl)acetic acid (20)

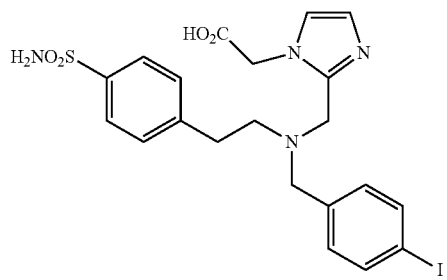 [SMILES: NS(=O)(=O)c1ccc(CCN(Cc2ccc(I)cc2)Cc2nccn2CC(=O)O)cc1]

Step 1. tert-butyl 2-(2-(((4-iodobenzyl)(4-sulfamoylphenethyl)amino)methyl)-1H-imidazol-1-yl)acetate

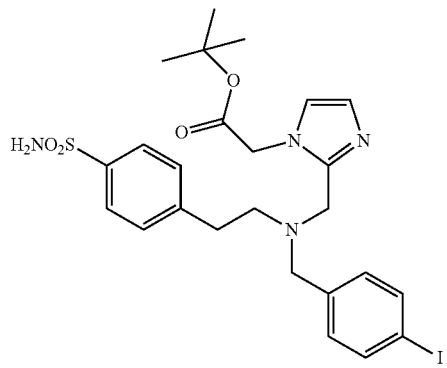 [SMILES: CC(C)(C)OC(=O)Cn1ccnc1CN(CCc1ccc(S(N)(=O)=O)cc1)Cc1ccc(I)cc1]

To a solution of 4-(2-((4-iodobenzyl)amino)ethyl)benzenesulfonamide (208 mg, 0.50 mmol), AcOH (0.05 mL) and tert-butyl 2-(2-formyl-1H-imidazol-1-yl)acetate (0.105 mg, 0.50 mmol) in DCE (10 mL) at 0° C. was added NaBH(OAc)₃ (0.30 g, 1.5 mmol). The reaction mixture was stirred at 0° C. for 30 minutes and at room temperature for overnight and decomposed with water. The reaction mixture was extracted with DCM. The organic layer was dried and concentrated under reduced pressure. The residue was purified by biotage over silica gel eluting with DCM to 10% MeOH in DCM to afford tert-butyl 242404-iodobenzyl)(4-sulfamoylphenethyl)amino)methyl)-1H-imidazol-1-yl)acetate (27.9 mg, 9.1%). ¹H NMR (400 MHz, CDCl₃) 7.78 (d, J=8.4 Hz, 2H), 7.65 (d, J=8.4 Hz, 2H), 7.15 (d, J=8.4 Hz, 2H), 7.03 (d, J=8.0 Hz, 2H), 6.95 (d, J=1.2 Hz, 1H), 6.79 (d, J=0.8 Hz, 1H), 4.78 (s, 2H), 4.31 (s, 2H), 3.62 (s, 2H), 3.57 (s, 2H), 2.82-2.68 (m, 4H), 1.39 (s, 9H); MS (ESI), 611.1 (M+H)⁻.

Step 2. 2-(2-(((4-iodobenzyl)(4-sulfamoylphenethyl)amino)methyl)-1H-imidazol-1-yl)acetic acid (20)

A solution of tert-butyl 2-(2-(((4-iodobenzyl)(4-sulfamoylphenethyl)amino)methyl)-1H-imidazol-1-yl)acetate (24 mg, 0.0393 mmol) in DCM (1.0 mL) and TFA (1.0 mL)

was stirred at room temperature for 5 hrs. Solvent was removed under a stream of nitrogen to give a residue, which was purified by HPLC to give compound (20) containing 2 TFA as a white solid (30 mg, 100%). $^1$H NMR (400 MHz, DMSO-$d_6$) 7.68-7.57 (m, 6H), 7.26 (d, J=8.0 Hz, 2H), 7.25 (s, 2H), 7.13 (d, J=8.4 Hz, 2H), 4.90 (s, 2H), 3.94 (s, 2H), 3.67 (s, 2H), 2.80 (t, J=7.8 Hz, 2H), 2.55 (t, J=7.8 Hz, 2H); MS (ESI), 555.0 (M+H)$^-$.

Biological Studies

Cell Culture

The human cervical cancer cell line, HeLa, was obtained from the American Type Culture Collection (Rockville, Md.). The human renal cancer cell lines, SK-RC-52 which constitutively expresses CA IX, and SK-RC-59 which does not express CA IX, were obtained from Memorial Sloan Kettering Cancer Center. All cells were grown according to the supplier's protocols in a humidified incubator at 37° C./5% $CO_2$. Cells were removed from flasks for passage or for transfer to 12-well assay plates by incubating them with 0.25% trypsin/EDTA (Invitrogen).

Determination of Binding Affinity

The ability of the CA IX inhibitors to compete with [$^{99m}$Tc]-(4) for binding to hypoxic HeLa cells was examined. HeLa cells were plated in 12-well plates at approximately $2.5 \times 10^5$ cells/well and allowed to adhere to the plate for 24 hr. Cells were then incubated under hypoxic conditions (0.1% $O_2$/5% $CO_2$ at 37° C.) for an additional 24 hr. The cells were then removed from hypoxia and incubated for 1 hr in Hank's Balanced Slat Solution (HBSS) with 0.5% BSA and 3 nM [$^{99m}$Tc]-(4) in the presence of 1-10,000 nM test CA IX inhibitor. The assay media was then removed and the cells were washed 2× with cold HBSS/0.5% BSA, collected by adding 0.25 mL of 1% SDS, and transferred to a 1.5 mL tube for counting the amount of radioactivity bound using a Wallac 1282 automated gamma counter. $IC_{50}$ values were determined by non-linear regression using GraphPad Prism software.

As illustrated by the competitive binding curves in FIG. 1, the radionuclide complexes of compounds that conform to Formula I are more potent inhibitors of CA IX with $IC_{50}$ values in the nanomolar range. In sharp contrast, the free (uncomplexed) compounds bind CA IX with $IC_{50}$ values that are at least 2-250-fold greater than the $IC_{50}$ of the corresponding complex.

In one embodiment of the present invention, therefore, complexes according to Formula II bind CA IX at least 2-200-fold more tightly than the corresponding free, uncomplexed compounds. In some embodiments, the binding, or inhibitory potency of the metal complex is at least 2-200-fold, 2-175-fold, 2-150-fold, 2-125-fold, 2-100-fold, 2-90-fold, 2-80-fold, 2-70-fold, 2-60-fold, 2-50-fold, 2-40-fold, 2-30-fold, 2-20-fold, or 2-10-fold greater than the binding, or inhibitory potency of the corresponding free (uncomplexed) compounds.

For instance, rhenium and technetium tricarbonyl metal complexes of certain Formula I compounds competitively bind more tightly (lower inhibition constants ($IC_{50}$) values), to CA IX expressing hypoxic HeLa cells than the corresponding free, uncomplexed Formula I compounds (ligands). Using the same assay conditions, the observed $IC_{50}$ values for the tricarbonyl metal complex is lower than the observed $IC_{50}$ value for free, uncomplexed ligand by a factor of at least 10, by a factor of at least 20, by a factor of at least 30, by a factor of at least 50, by a factor of at least 100, by a factor of at least 150, or by a factor of at least 200.

Accordingly, the tricarbonyl metal complexes of Formula I compounds are suitable candidate agents for imaging tumor tissues that are known to have a high expression of CA IX as compared to non-tumor tissues. as Tissue Biodistribution in Human Xenograft Bearing Mice To influence the pharmacokinetic properties of Formula I compounds and their complexes with radionuclides, the present inventors studied whether the position and number of carboxyl groups or carboxyalkylene groups could influence selective retention of the inventive complexes in Ca IX expressing tumor tissue versus non-tumor tissues.

Briefly, prior to inoculation of mice, Hek293/CA9 cells were trypsinized, counted, and suspended in 50% PBS with 1 mg/ml D-glucose, 36 mg/ml sodium pyruvate, 50% Matrigel (BD Biosciences, Franklin Lakes, N.J.). NCr$^{nu/nu}$ mice were anesthetized by intraperitoneal injection of 0.5 ml Avertin (20 mg/ml) (Sigma-Aldrich) and then inoculated subcutaneously into the hind flank with $2 \times 10^6$ cells suspended in 0.25 ml of buffer.

Studies aimed at measuring tumor uptake were initiated when the tumors reached an average size of 100-200 mm$^3$. Tissue distribution was assesed by administering via the tail vein, a bolus injection of approximately 2 µCi/mouse of the radiolabeled CA IX inhibitor dissolved either in slaine, or in a mixed solvent comprising 10% ethanol in saline, or a mixed solvent having 10% dimethylsulfoxide (DMSO) in saline. Groups of five animals were euthanized by asphyxiation with carbon dioxide at 1, 4, and 24 hours post injection. The ability of the inventive CA IX inhibitors to specifically bind CA IX protein was studied by co-injecting a cohort of mice with acetazolamide (AZO) at a dose of 10 mg/kg.

The distribution of the inventive CA IX inhibitors was measured in the following tissues: tumor, blood, heart, liver, lungs, spleen, large and small intestine, stomach, kidneys and skeletal muscle. Tissues were excised from euthanized mice at the predetermined time point following administration of the inventive CA IX inhibitors. The tissues were weighed (wet), transferred to plastic tubes and the radioactivity counted using an automated γ-counter (LKB Model 1282). The percent radioactivity remaining in a tissue at a specific time interval post administration of the inventive CA IX was expressed as percent injected dose per gram tissue (% ID/g) and percent injected dose per organ (% DPO). Graphically, data from such studies involving different inventive CA IX inhibitors are shown in FIGS. 2-6.

FIGS. 2-6 illustrate the in vivo biodistribution characteristics and pharmacokinetic behavior of certain metal complexes of poly(carboxyl)amine-containing ligands that conform to Formula I as described herein. In particular for each of these Figures, one can determine the ratio of the sum of percent injected dose per gram tissue (% ID/g) values for liver and kidney tissues to the % ID/g value for tumor tissue at two separate time points: (i) one hour post-administration of the metal complex to CA9/293 xenograft mice, and (ii) four hours post-administration of the metal complex to CA9/293 xenograft mice. What one finds is that this ratio decreases between the first time point (1 hour post-administration) and the second time point (4 hours post-administration). For the examples provided in these Figures, the decrease in this ratio ranges from about 2 to about 4.

Figure 2:
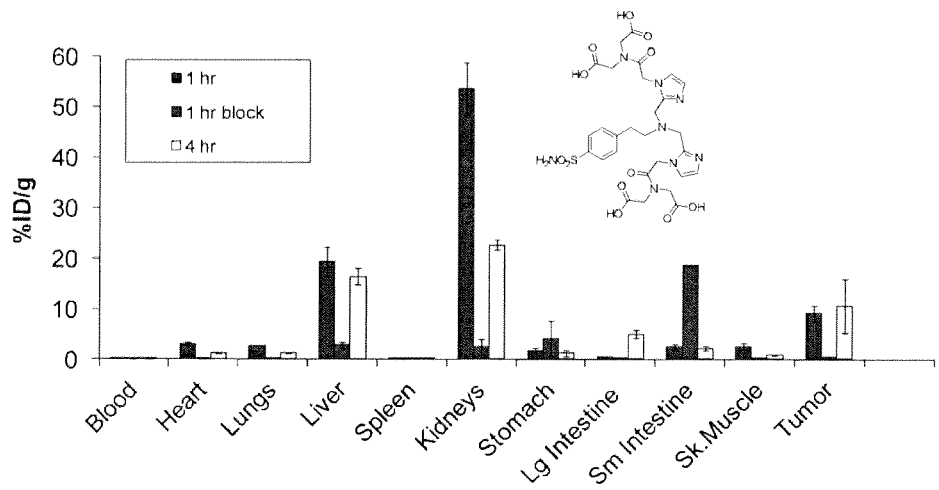
FIGS. 2-6 illustrate tissue biodistribution and bioclearance data for various non-tumor and CA IX expressing tumor tissues. Representative CA IX technitium-99m complexes used in these studies have an ethylene linker connecting the chelator to the sulfonamide moiety.
Figure 3:
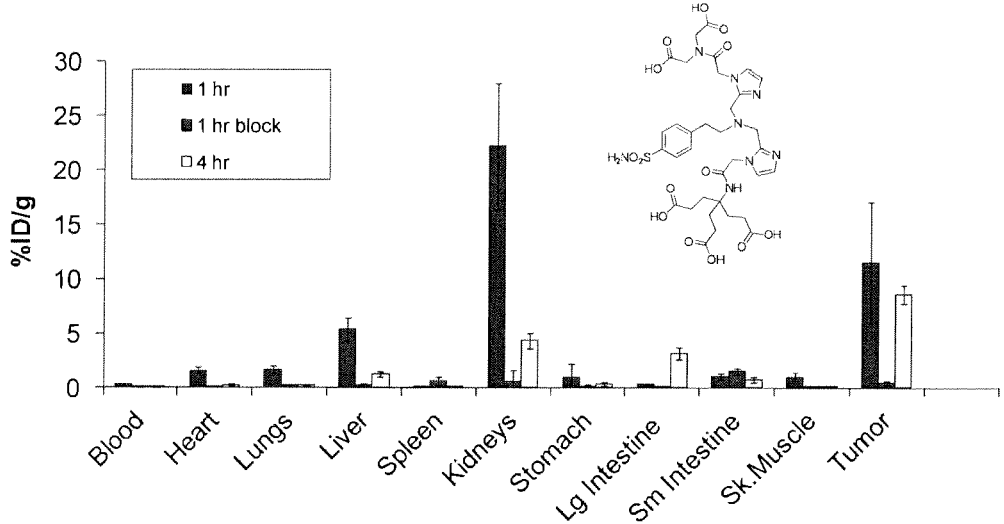
Figure 4:
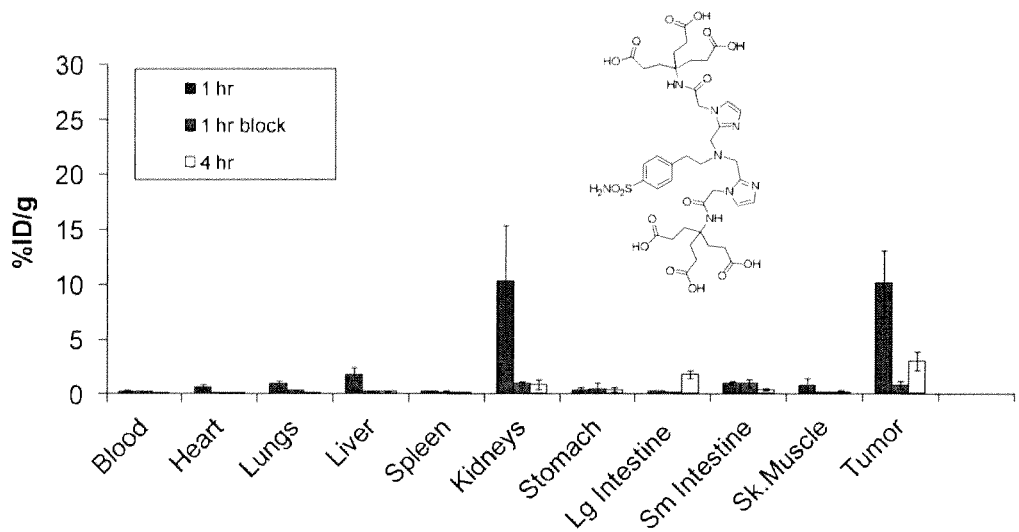

Data presented in FIGS. 2-4 also illustrate a correlation between the number of carboxyl groups that are present in the complex and the pharmacokinetic profile (tissue distribution and clearence) for technicium-99m complexes of certain Formula I compounds. The complex illustrated in FIG. 2 has two methylene carboxyl groups per immidazole chelating group, for a total of four methylene carboxyl groups in the molecule [$^{99m}$Tc]-(5). The complex illustrated in FIG. 3 has a total of five methylene carboxyl groups, while the complex of FIG. 4 has a total of six methylene carboxyl groups.

It is clear from FIGS. 2-4 that CA IX inhibitors according to the present invention can be detected in various tissues tested in this study. In fact, high concentrations of CA IX inhibitors according to the present invention were detected in the kidney and liver of mice. Without being bound to any particular theory, the present inventors believe that the greater concentration of CA IX inhibitor in kidney and liver are primarily due to the role of these two organs in detoxification of drugs and their excretion from the body.

The presence and number of carboxyl groups may also have an effect on the tissue distribution and bioclearance of the inventive CA IX inhibiotors. For instance, at a time interval of one hour post administration of the inventive CA IX inhibitors the % ID/g of tumor tissues remained constant at a measured value of approximately 10% for each of the three CA IX inhibitors tested. In contrast, the % ID/g of liver decreased from a value of 20% for the CA IX inhibitor having a total of four methylene carboxyl groups (FIG. 2), to a value of 5% and 2% in the livers obtained from mice treated with the CA IX inhibitor having a total of five and six methylene carboxyl groups respectively (FIGS. 3 and 4 respectively).

A similar trend was observed for kidneys. That is, at one hour post administration of the inventive CA IX inhibitors, approximately 55% of the injected dose was retained in kidneys for the CA IX inhibitor having a total of four methylene carboxyl groups (FIG. 2). The % ID/g of kidney tissue from mice administered CA IX inhibitors having a total of five and six methylene carboxyl groups was about 22% and 10% respectively, (FIGS. 3 and 4 respectively). Together, the above data implicates a role for the presence of polar carboxyl groups in influencing tumor-specific concentration in vivo.

Data illustrated in FIGS. 2-4 further indicate that while the % ID/g of tumor remains relatively constant at 4 hours post-administration of CA IX inhibitors, these compounds are rapidly cleared from non-tumor tissues. Accordingly, the data in FIGS. 2-4 provides support for a correlation between tissue clearance and the total number methylene carboxyl groups present in the CA IX inhibitor.

Data from these figures indicates that this correlation is more pronounced in non-tumor tissues than in tumor. For instance, while the percent injected dose (% ID/g) remains the same at 1 hour and at 4 hours post-administration (see FIG. 2) in tumors, the % ID/g of kidney decreases by 60% at 4 hours post-administration (FIG. 2). A similar trend is seen in FIGS. 3 and 4, where the % ID/g in kidney decreases by greater than 77% for the inventive CA IX inhibitor having five methylene carboxyl groups (FIG. 3). Analysis of kidney tissue from mice at 4 hours post administration of the CA LX inhibitor having six methylene carboxyl groups, indicates no measurable levels of this inhibitor in the kdneys.

Without being bound to a particular hypothesis, the present inventors believe that a correlation exists between the rate of clearance of inhibitor from tissue and the total number of methylene carboxyl groups that are present. This drug clearance effect is clearly more pronounced in non-tumor tissues.

Figure 5:
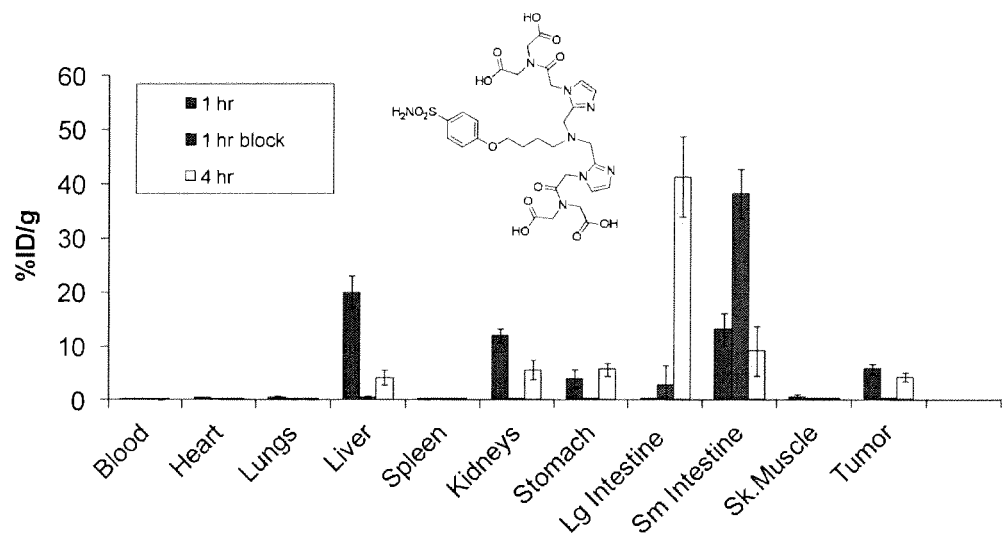
Figure 6:
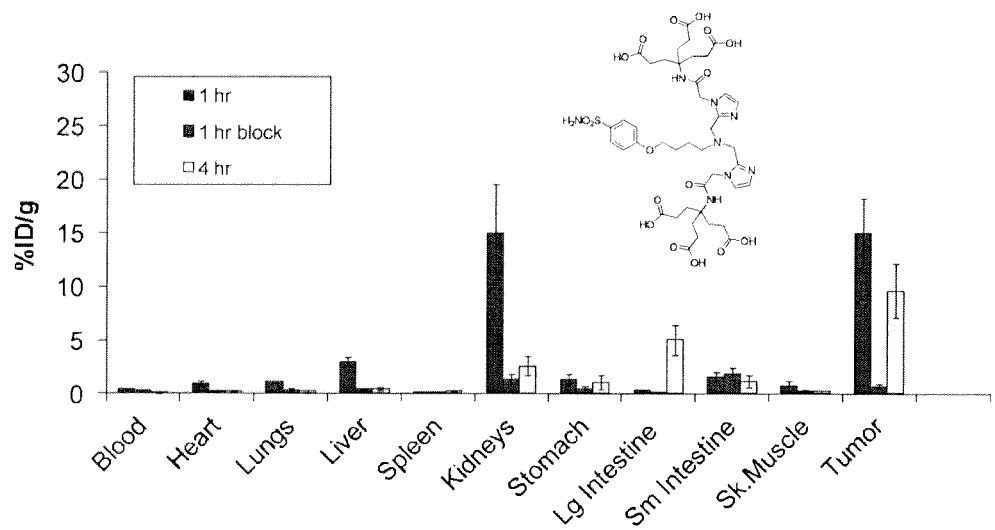

The introduction of a polar oxygen atom in the linker is also believed to influence tissue distribution and clearance. As illustrated in FIG. 5, the concentration of the CA IX inhibitor having a butyloxy group as the linker was greates in the large intestine which has a predominantly aqueous environment. Again the % ID/g is greater in liver and kidneys than in tumor. However, it is clear that bioclearence of the inventive CA IX inhibitor is more rapid from non-tumor tissues than tumor. For example, approximately 75% of injected drug is cleared from liver at 4 hours post-administration and greater than 50% drug clearance is observed at 4 hours from kidneys. The percent of injected drug cleared from tumor at 4 hours is much lower, about 25% ID/g.

Increasing the total number of carboxyl groups increases bioclearence from non-tumor tissues as awell as from tumor (FIG. 6), indicating a role for the carboxyl groups in bioclearence.

It was also observed by the present inventors that the percent bioclearance from tumor for the CA IX inhibitor having a polar linker (FIGS. 5 and 6), is greater than the percent bioclearance from tumor obtained from mice that received CA IX inhibitors having an alkyl linker (FIG. 2).

Summarizing the results from these studies it is clear that the number of carboxyl groups present in a compound of Formula I exerts an apparent effect on the clearance of the metal complex thereof from certain non-target tissues (e.g., liver and kidneys). In particular, FIGS. 2 and 5 illustrate the pharmacokinetic behavior of two different compounds of Formula I, each having four carboxyl groups. One observes that the ratio of the sum of percent injected dose per gram tissue (% ID/g) values for liver and kidney tissues to the % ID/g value for tumor tissue decreases from 1 hour post-administration to 4 hours post-administration by a factor of about 2.5. In contrast, FIG. 3, which illustrates the pharmacokinetic behavior of a compound of Formula I having five carboxyl groups, shows that this ratio decreases by a factor of about 3.9. Consistent with this trend, FIGS. 4 and 6, in which the compound of interest possesses six carboxyl groups, shows that this ratio decreases by a factor of about 4.0. In any case, and regardless of the number of carboxyl groups present in the compound of interest, the metal complexes thereof appear to retain a high value for the percent injected dose per gram tissue (% ID/g) in the target tissue, which is CA IX expressing tumor tissue, over the course of the first four hours post-administration.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third

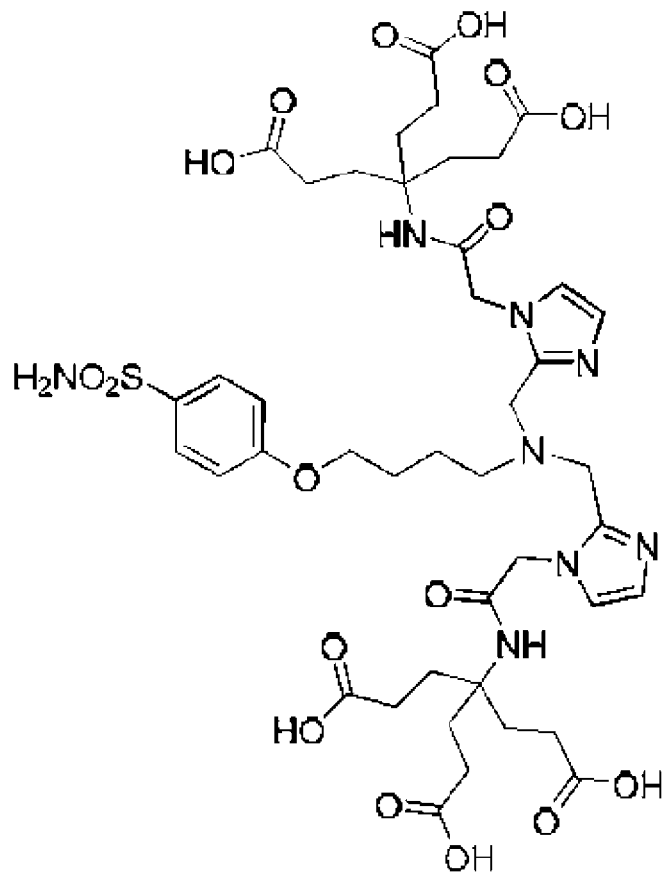

What is claimed is:

1. A compound of Formula I:

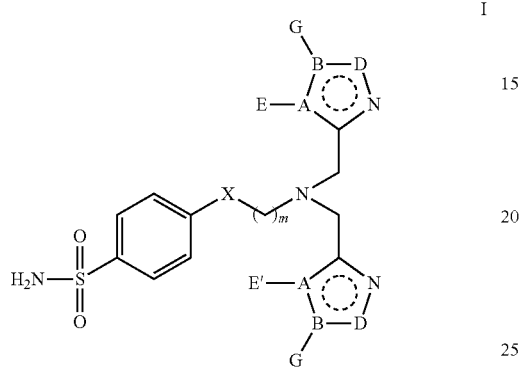

in which
X is selected from the group consisting of —(CH$_2$)$_n$—, —(CH$_2$)$_n$—O—, —(CH$_2$)$_n$—N(R$_g$)—, —(CH$_2$)$_n$—N(R$_g$)—C(O)— and —O—;
R$_g$ is hydrogen or (C$_1$-C$_6$)alkyl;
A is —N—;
B and D are each independently —(CH)—;
E is —(CH$_2$)—Z-Q;
E' is —(CH$_2$)—Z-Q';
Z is —(CH$_2$)$_p$—, or —C(O)—
Q is selected from the group consisting of —H, —OR$_g$, and NR$_a$R$_b$
Q' is NR$_d$R$_e$ and R$_e$ is

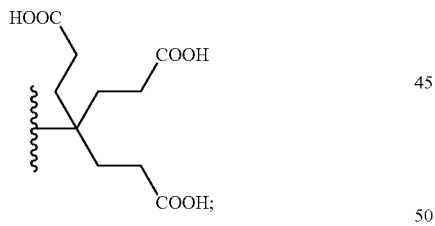

R$_a$, R$_b$, and R$_d$ are each independently hydrogen, substituted or unsubstituted (C$_1$-C$_6$)alkyl, or substituted or unsubstituted carboxy(C$_1$-C$_6$)alkylene;
G is —(CH(R$_m$))$_n$—R$_h$, or —(CH$_2$)$_p$—C(O)—R$_h$;
R$_h$ is selected from the group consisting of —H, —OH, NR$_a$R$_b$ and —CO$_2$H;
R$_m$ is selected from the group consisting of —H, —COOH and substituted or unsubstituted —COO(C$_1$-C$_6$)alkyl;
m, n and p independently are integers between 0 to 10 inclusive; and
⌢ represents the option of having one or more double bonds; or
a pharmaceutically acceptable salt, tautomer, or ester thereof.

2. The compound of claim 1, in which X is —(CH$_2$)$_n$— and m is 2.

3. The compound of claim 1, in which X is —O— and m is 4.

4. The compound of claim 1, in which R$_a$ and R$_b$ are each independently substituted or unsubstituted carboxy(C$_1$-C$_6$) alkylene, and R$_d$ is hydrogen.

5. The compound of claim 4, in which R$_a$ and R$_b$ are each independently

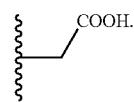

6. The compound of claim 1, in which R$_a$ and R$_d$ are each independently hydrogen, and R$_b$ is substituted or unsubstituted (C$_1$-C$_6$)alkyl.

7. The compound of claim 6, in which R$_b$ is

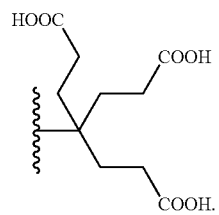

8. The compound of claim 1, in which the compound is an inhibitor of carbonic anhydrase (CA) IX.

9. The compound of claim 1, which is:

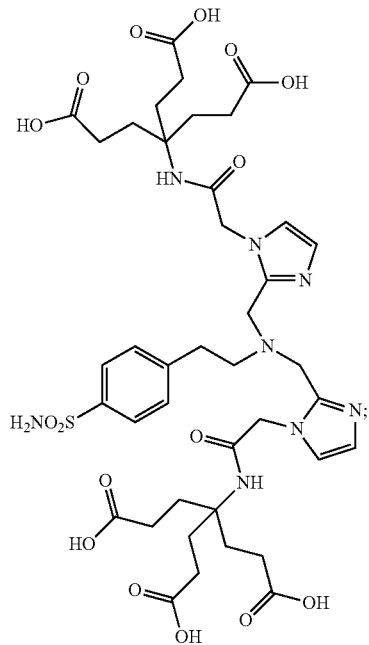 [SMILES: NS(=O)(=O)c1ccc(CCN(Cc2nccn2CC(=O)NC(CCC(=O)O)(CCC(=O)O)CCC(=O)O)Cc2nccn2CC(=O)NC(CCC(=O)O)(CCC(=O)O)CCC(=O)O)cc1]

-continued

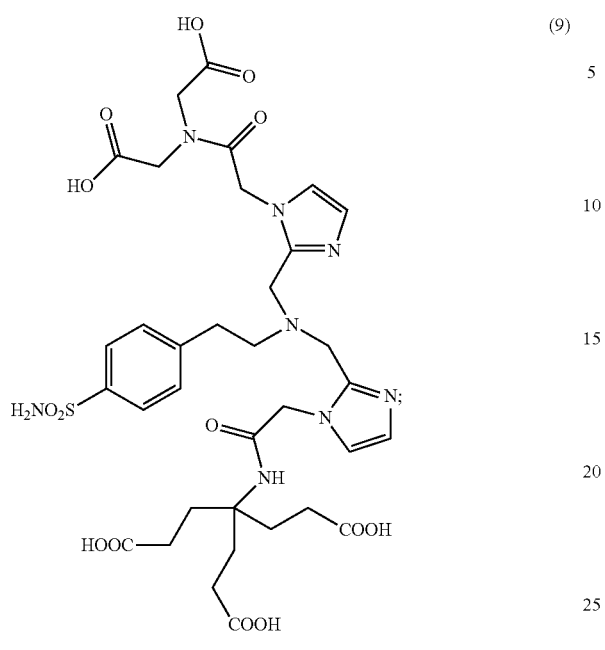

(9)

or a pharmaceutically acceptable salt thereof.

10. A metal complex of Formula II or a pharmaceutically acceptable salt, tautomer, or ester thereof:

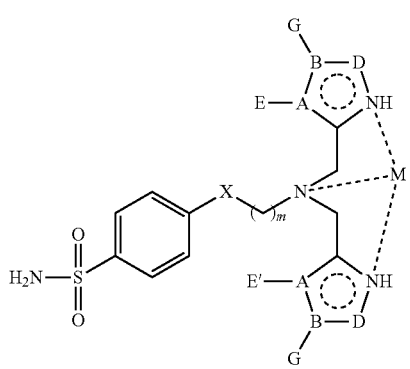

II wherein:
X is selected from the group consisting of —$(CH_2)_n$—, —$(CH_2)_n$—O—, —$(CH_2)_n$—N($R_g$)—, —$(CH_2)_n$—N($R_g$)—C(O)— and —O—;
$R_g$ is hydrogen or ($C_1$-$C_6$)alkyl;
A is —N—;
B and D are each independently —(CH)—;
E is —$(CH_2)$—Z-Q;
E' is —$(CH_2)$—Z-Q';
Z is —$(CH_2)_p$—, or —C(O)—
Q is selected from the group consisting of —H, —$OR_g$, and $NR_aR_b$ Q' is $NR_dR_e$ and $R_e$ is

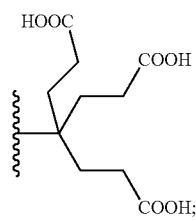 [SMILES: *C(CCC(=O)O)(CCC(=O)O)CCC(=O)O]

$R_a$, $R_b$, and $R_d$ are each independently hydrogen, substituted or unsubstituted ($C_1$-$C_6$)alkyl, or substituted or unsubstituted carboxy($C_1$-$C_6$)alkylene;
G is —$(CH(R_m))_n$—$R_h$—, or —$(CH_2)_p$—C(O)—$R_h$;
$R_h$ is selected from the group consisting of —H, —OH, $NR_aR_b$ and —$CO_2H$;
$R_m$ is selected from the group consisting of —H, —COOH and substituted or unsubstituted —COO ($C_1$-$C_6$)alkyl;
m, n and p independently are integers between 0 to 10 inclusive;
⸺ represents the option of having one or more double bonds; and
M is Pt, Zn, $^{64}Cu$, $^{186}Re$, $^{188}Re$ or $^{99m}Tc$.

11. The metal complex of claim 10, wherein M is $^{99m}Tc$, $^{186}Re$, or $^{188}Re$.

12. The metal complex of claim 10 which is:

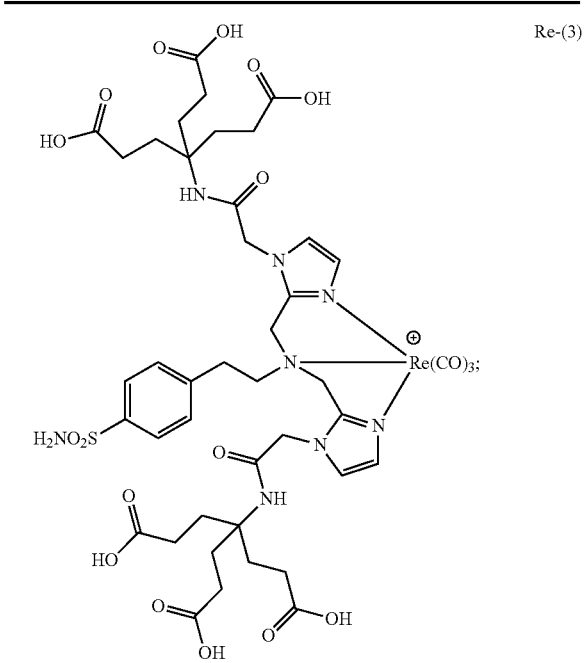

Re-(3)

-continued

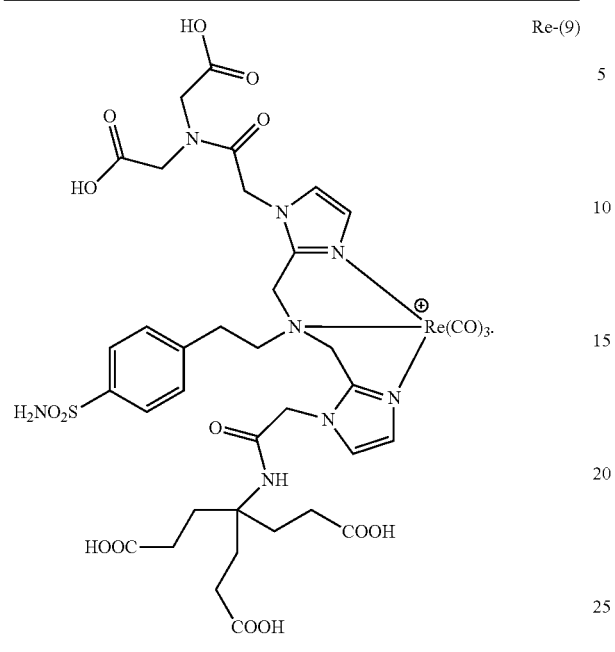

Re-(9)

13. The metal complex of claim 10, in which the ratio of the sum of percent injected dose per gram tissue (% ID/g) values for liver and kidney tissues to the % ID/g value for tumor tissue decreases when observed at a first time point, which is one hour post-administration of the metal complex to CA9/293 xenograft mice, and at a second time point, which is four hours post-administration of the metal complex to CA9/293 xenograft mice.

14. The metal complex of claim 13, in which the decrease in the ratio ranges from about a factor of about 2 to a factor of about 4.

15. A pharmaceutical composition comprising at least one compound of claim 1 and a pharmaceutically acceptable carrier.

16. A pharmaceutical composition comprising at least one metal complex of a compound of claim 10 and a pharmaceutically acceptable carrier.

17. A method for imaging a patient suspected of harboring CA IX expressing tumor tissue, the method comprising:
   administering to a patient suspected of harboring CA IX expressing tumor tissue a diagnostically effective amount of a radionuclide metal complex of a compound of Formula I, or a pharmaceutically acceptable salt, tautomer, or ester thereof; and
   obtaining an image of the patient, including any CA IX expressing tumor tissue, if any;

wherein:
the compound of Formula I is:

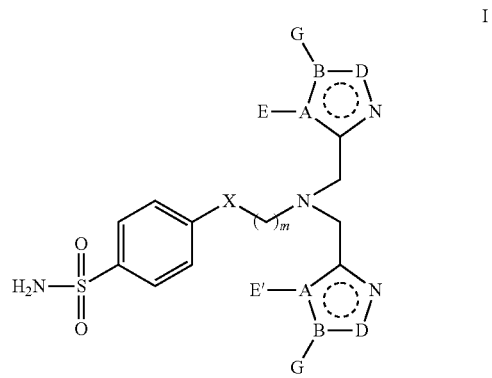

I

X is selected from the group consisting of —(CH$_2$)$_n$—, —(CH$_2$)$_n$—O—, —(CH$_2$)$_n$—N(R$_g$)—, —(CH$_2$)$_n$—N(R$_g$)—C(O)— and —O—;

R$_g$ is hydrogen or (C$_1$-C$_6$)alkyl;

A is —N—;

B and D are each independently —(CH)—;

E is —(CH$_2$)—Z-Q;

E' is —(CH$_2$)—Z-Q';

Z is —(CH$_2$)$_p$—, or —C(O)—

Q is selected from the group consisting of —H, —OR$_g$, and NR$_a$R$_b$

Q' is NR$_d$R$_e$ and R$_e$ is

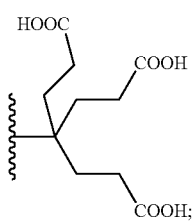

R$_a$, R$_b$, and R$_d$ are each independently hydrogen, substituted or unsubstituted (C$_1$-C$_6$)alkyl, or substituted or unsubstituted carboxy(C$_1$-C$_6$)alkylene;

G is —(CH(R$_m$))$_n$—R$_h$—, or —(CH$_2$)$_p$—C(O)—R$_h$;

R$_h$ is selected from the group consisting of —H, —OH, NR$_a$R$_b$ and —CO$_2$H;

R$_m$ is selected from the group consisting of —H, —COOH and substituted or unsubstituted —COO(C$_1$-C$_6$)alkyl;

m, n and p independently are integers between 0 to 10 inclusive; and

⌒ represents the option of having one or more double bonds.

18. A kit for the preparation of an agent targeting CA IX expressing tumor tissue comprising:
a compound according to Formula I, or a pharmaceutically acceptable salt, tautomer, or ester thereof:

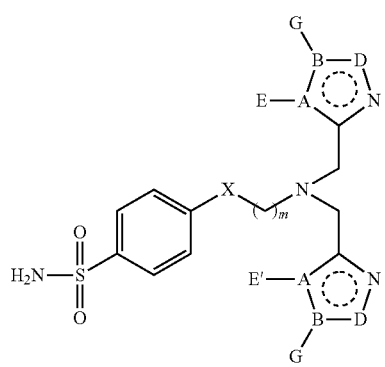

wherein:
X is selected from the group consisting of —(CH$_2$)$_n$—, —(CH$_2$)$_n$—O—, —(CH$_2$)$_n$—N(R$_g$)—, —(CH$_2$)$_n$—N(R$_g$)—C(O)— and —O—;
R$_g$ is hydrogen or (C$_1$-C$_6$)alkyl;
A is —N—;
B and D are each independently —(CH)—;
E is —(CH$_2$)—Z-Q;
E' is —(CH$_2$)—Z-Q';
Z is —(CH$_2$)$_p$—, or —C(O)—
Q is selected from the group consisting of —H, —OR$_g$, and NR$_a$R$_b$
Q' is NR$_d$R$_e$ and R$_e$ is

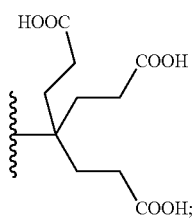

R$_a$, R$_b$, and R$_d$ are each independently hydrogen, substituted or unsubstituted (C$_1$-C$_6$)alkyl, or substituted or unsubstituted carboxy(C$_1$-C$_6$)alkylene;
G is —(CH(R$_m$))$_n$—R$_h$—, or —(CH$_2$)$_p$—C(O)—R$_h$;
R$_h$ is selected from the group consisting of —H, —OH, NR$_a$R$_b$ and —CO$_2$H;
R$_m$ is selected from the group consisting of —H, —COOH and substituted or unsubstituted —COO(C$_1$-C$_6$)alkyl;
m, n and p independently are integers between 0 to 10 inclusive; and
⌒ represents the option of having one or more double bonds.

19. The kit of claim 18 further comprising sodium boranocarbonate, sodium carbonate, sodium tartrate and sodium borate.

20. A method of preparing a metal complex for targeting CA IX expressing tumor tissue in a subject comprising:
contacting a metal-containing precursor, comprising a metal selected from the group consisting of Pt, Zn, $^{64}$Cu, $^{186}$Re, $^{188}$Re and $^{99m}$Tc, with an excess of free, uncomplexed compound of Formula I to provide a mixture comprising: free, uncomplexed compound of Formula I, and a metal complex of Formula I;
wherein:
the compound of Formula I is:

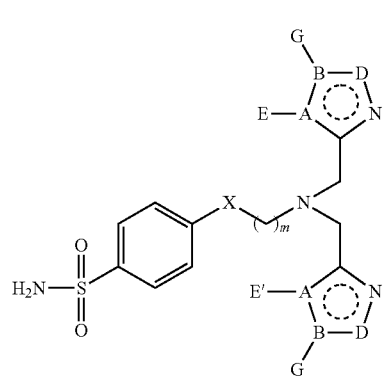

X is selected from the group consisting of —(CH$_2$)$_n$—, —(CH$_2$)$_n$—O—, —(CH$_2$)$_n$—N(R$_g$)—, —(CH$_2$)$_n$—N(R$_g$)—C(O)— and —O—;
R$_g$ is hydrogen or (C$_1$-C$_6$)alkyl;
A is —N—;
B and D are each independently —(CH)—;
E is —(CH$_2$)—Z-Q;
E' is —(CH$_2$)—Z-Q';
Z is —(CH$_2$)$_p$—, or —C(O)—
Q is selected from the group consisting of —H, —OR$_g$, and NR$_a$R$_b$
Q' is NR$_d$R$_e$ and R$_e$ is

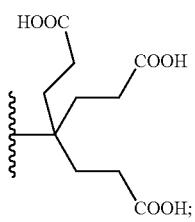

R$_a$, R$_b$, and R$_d$ are each independently hydrogen, substituted or unsubstituted (C$_1$-C$_6$)alkyl, or substituted or unsubstituted carboxy(C$_1$-C$_6$)alkylene;
G is —(CH(R$_m$))$_n$—R$_h$—, or —(CH$_2$)$_p$—C(O)—R$_h$;
R$_h$ is selected from the group consisting of —H, —OH, NR$_a$R$_b$ and —CO$_2$H;
R$_m$ is selected from the group consisting of —H, —COOH and substituted or unsubstituted —COO(C$_1$-C$_6$)alkyl;
m, n and p independently are integers between 0 to 10 inclusive; and
⌒ represents the option of having one or more double bonds.

21. The method of claim 20, which further comprises administering said mixture to a subject suspected of harboring CA IX expressing tumor tissue without taking any steps to separate the free, uncomplexed compound of Formula I from its metal complex.

22. The method of claim 21, which further comprises filtering said mixture prior to said administering step to sterilize said mixture.

23. The metal complex of claim 10 which is:
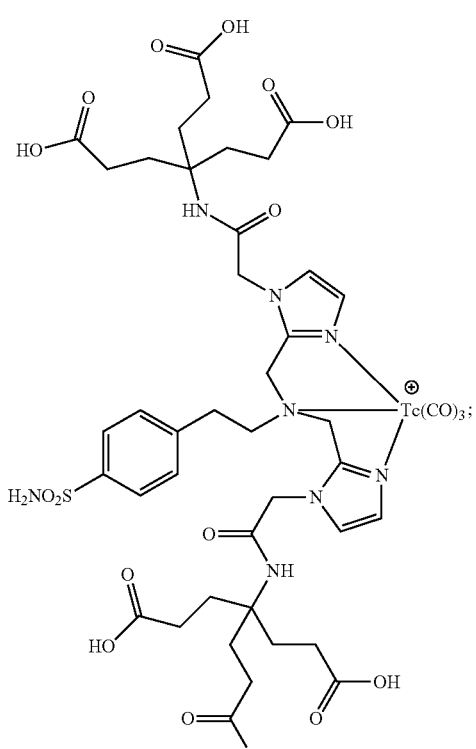
24. The compound of claim 1 which is:
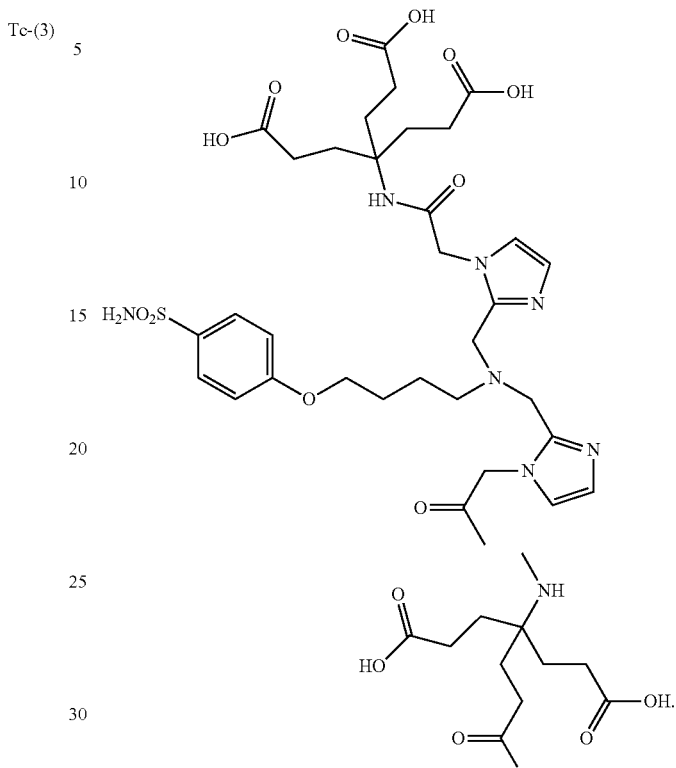
25. The metal complex of claim 10 which is:
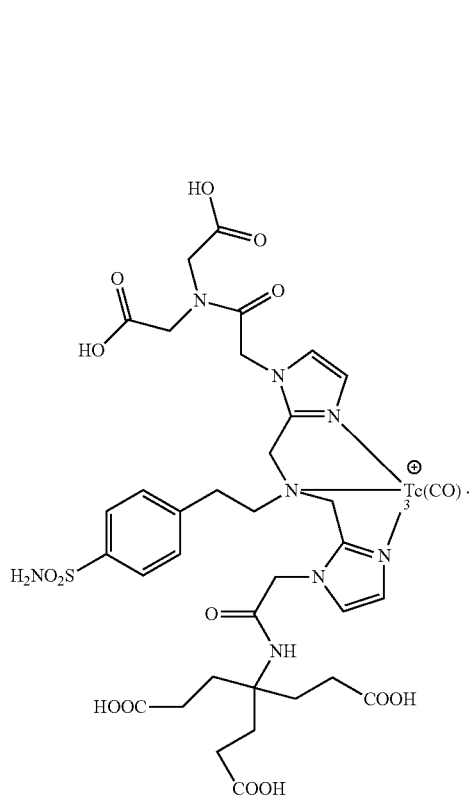
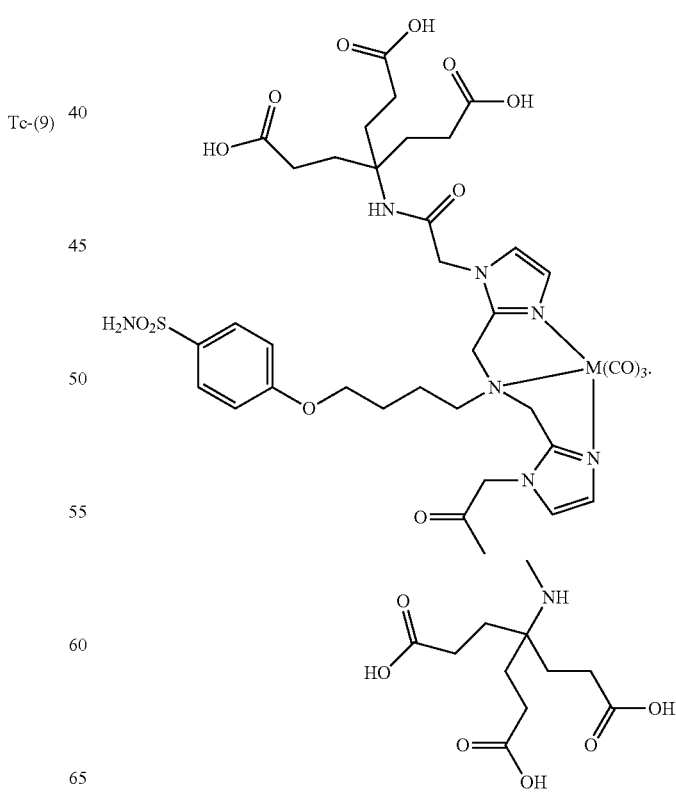

26. The metal complex of claim 25, wherein M is $^{99m}$Tc, $^{186}$Re, or $^{188}$Re.

27. The method of claim 17 in which the compound of Formula I is:

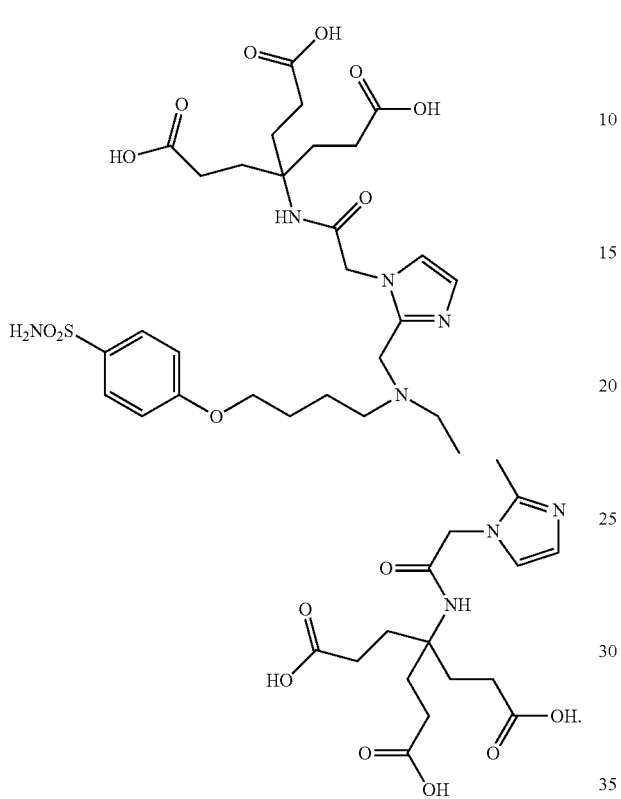

28. The kit of claim 18 in which the compound of Formula I is:

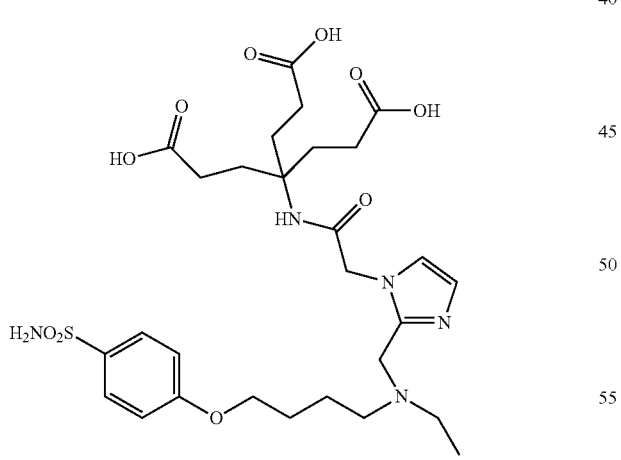

-continued

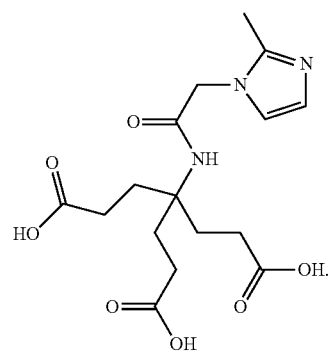

29. The method of claim 20 in which the compound of Formula I is:

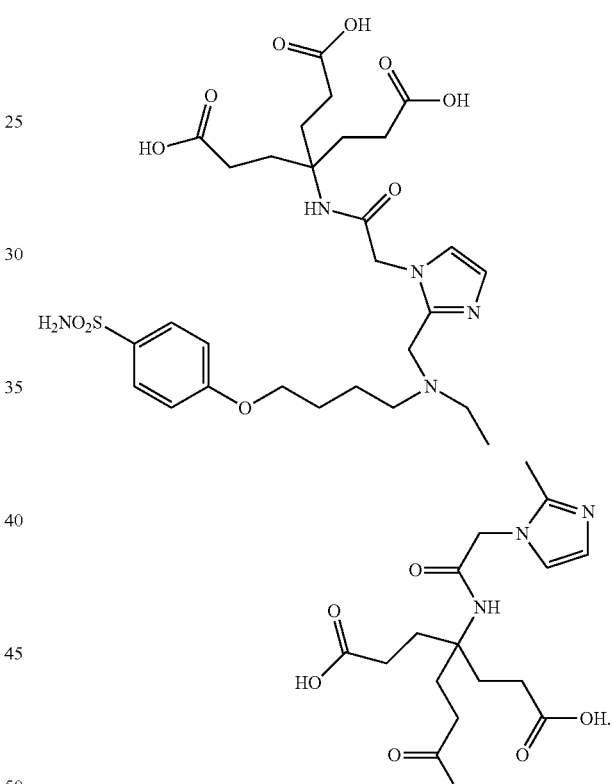

30. The kit of claim 18 further comprising a radionuclide configured to complex with the compound of Formula I.

31. The kit of claim 29, wherein the radionuclide is $^{99m}$Tc, $^{186}$Re, or $^{188}$Re.

* * * * *

UNITED STATES PATENT AND TRADEMARK OFFICE
CERTIFICATE OF CORRECTION

PATENT NO. : 9,120,837 B2  Page 1 of 9
APPLICATION NO. : 13/734534
DATED : September 1, 2015
INVENTOR(S) : John W. Babich et al.

It is certified that error appears in the above-identified patent and that said Letters Patent is hereby corrected as shown below:

In Column 80, Claim 24, line 5, replace the compound

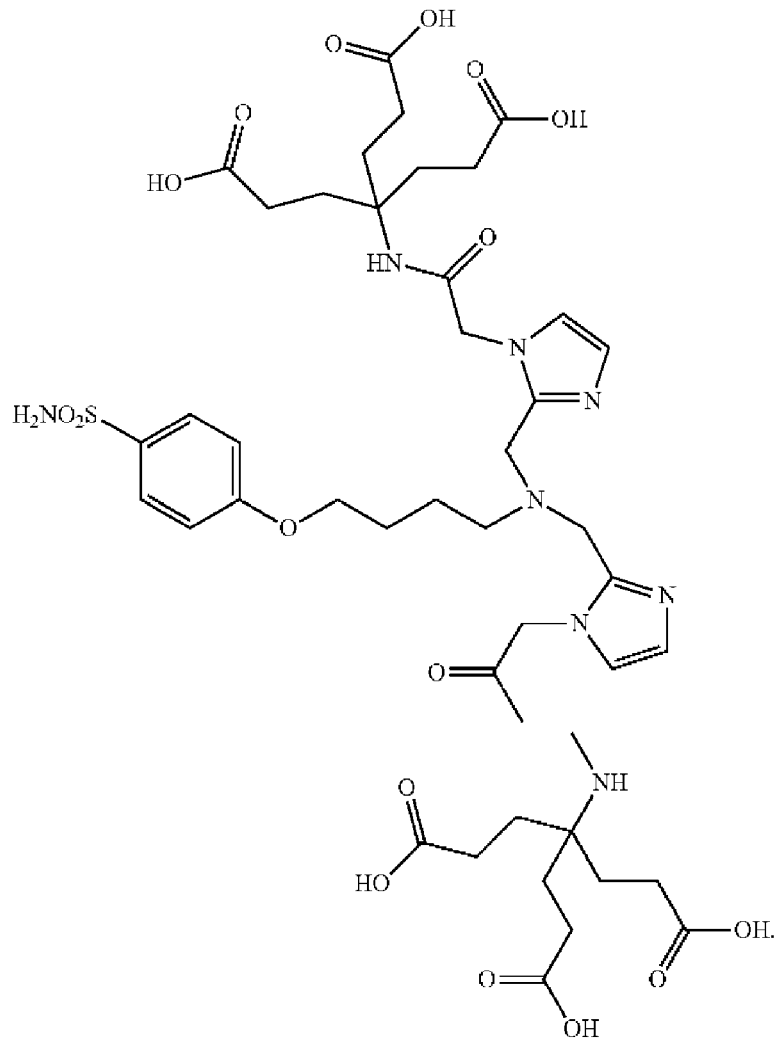

Signed and Sealed this
Twenty-third Day of February, 2016

Michelle K. Lee
*Director of the United States Patent and Trademark Office*

CERTIFICATE OF CORRECTION (continued)
U.S. Pat. No. 9,120,837 B2

In Column 80, Claim 24, line 5, Cont'd

With:

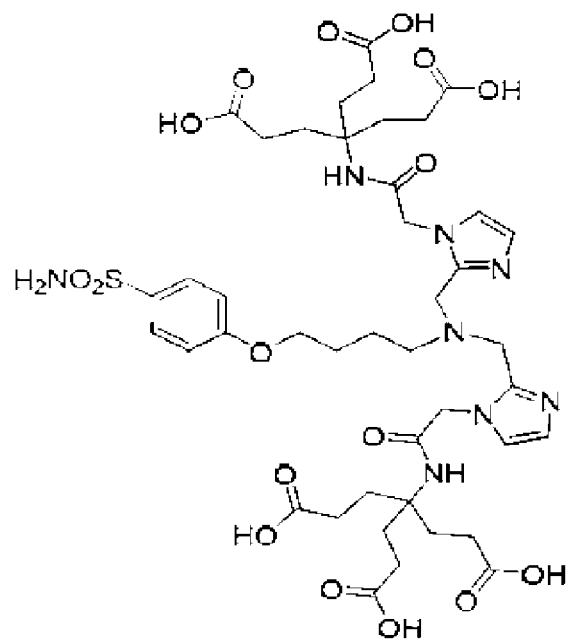

CERTIFICATE OF CORRECTION (continued)
U.S. Pat. No. 9,120,837 B2

Column 80, Claim 25, line 35, replace the complex

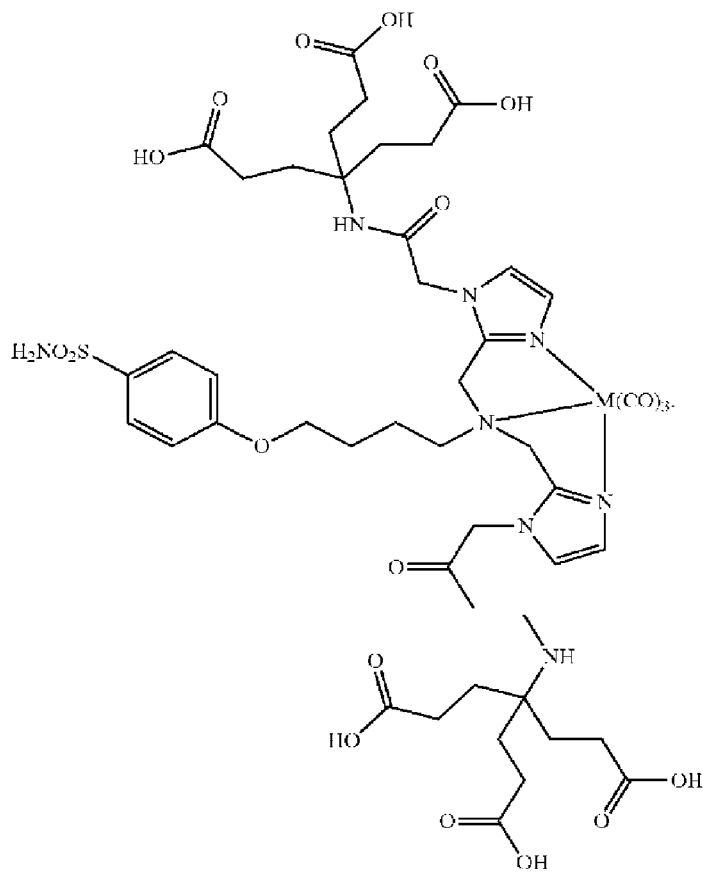

With:

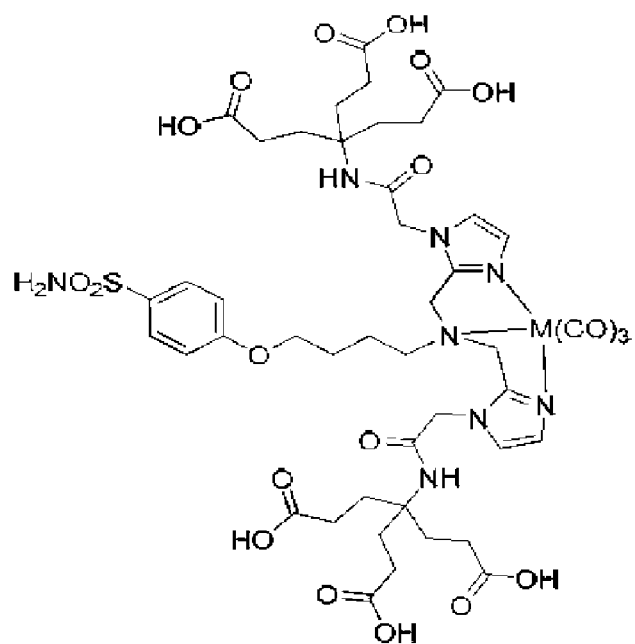

CERTIFICATE OF CORRECTION (continued)
U.S. Pat. No. 9,120,837 B2

Column 81, Claim 27, line 5 replace the compound

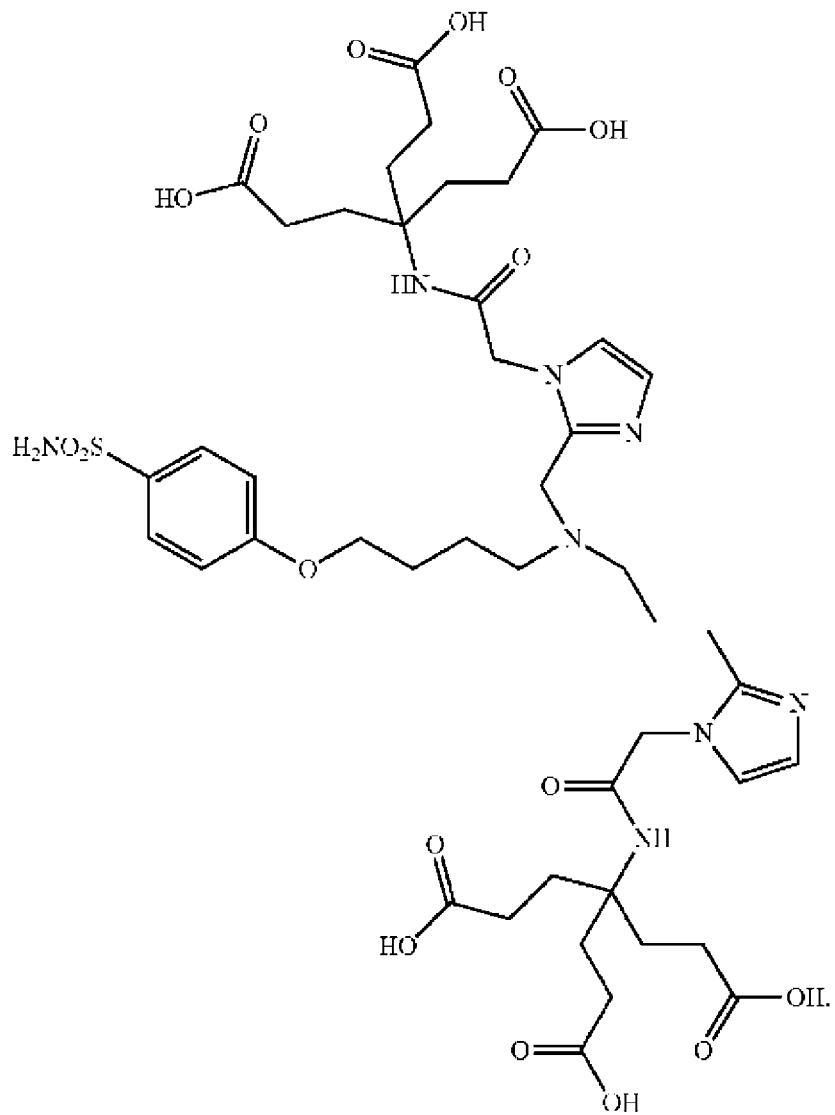

Column 81, Claim 27, line 5, Cont'd
With:
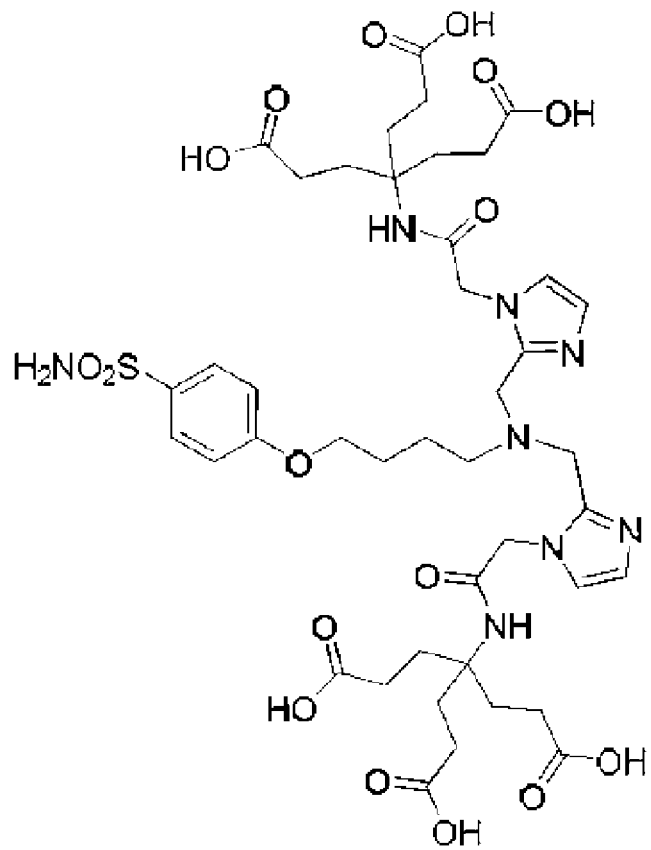

CERTIFICATE OF CORRECTION (continued)
U.S. Pat. No. 9,120,837 B2

Column 81 and 82, Claim 28, line 40 and line 1 replace the compound

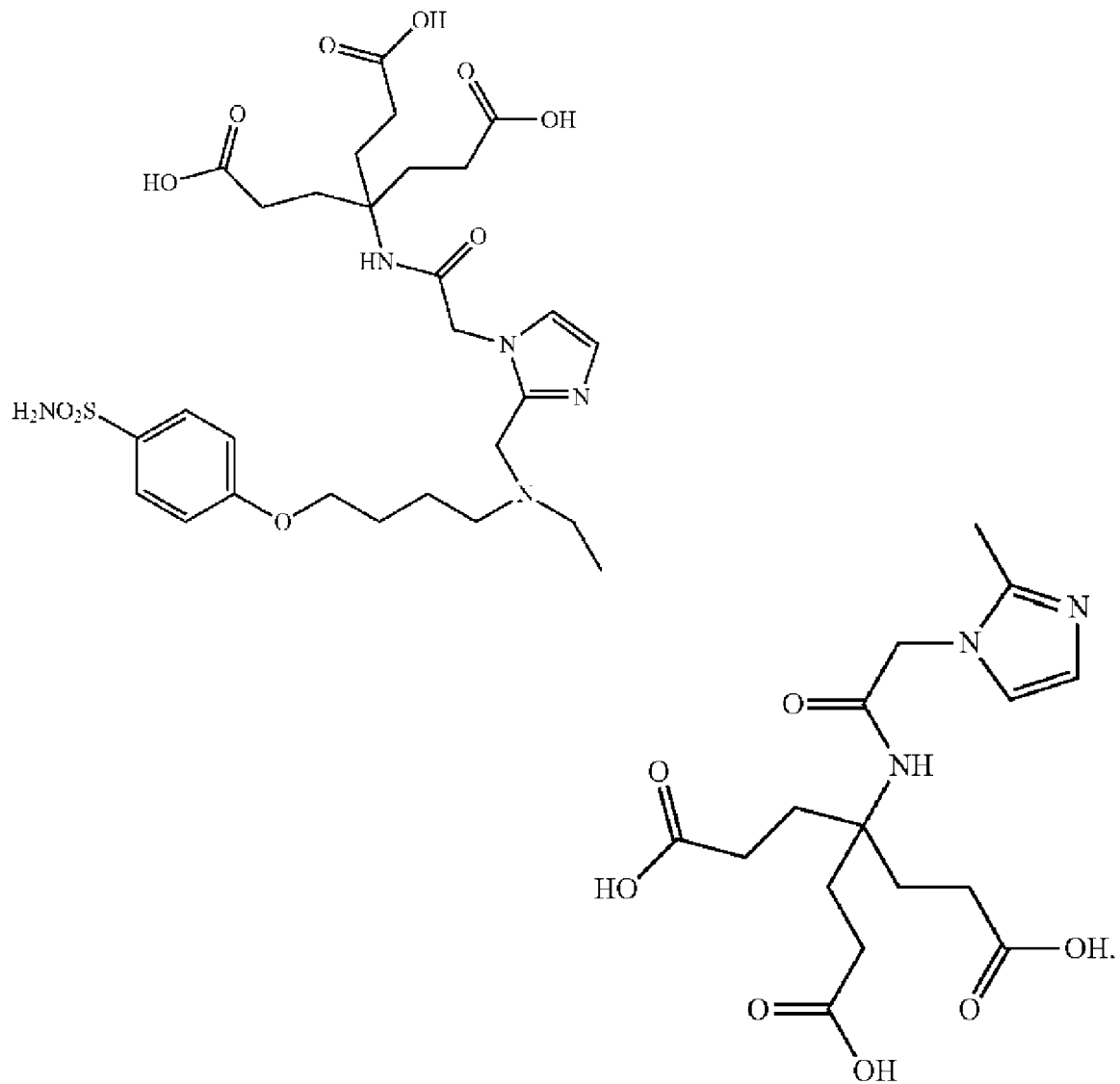

Column 81 and 82, Claim 28, line 40 and line 1, Cont'd
With:
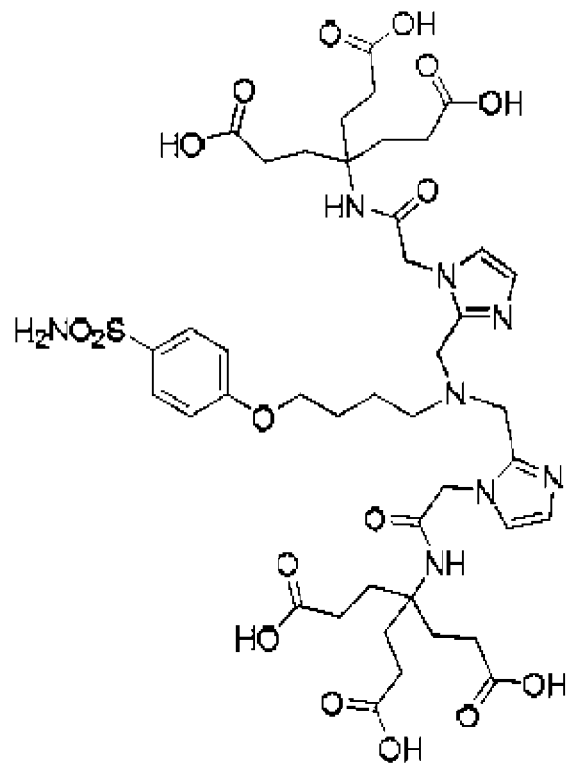

CERTIFICATE OF CORRECTION (continued)
U.S. Pat. No. 9,120,837 B2

Column 82, Claim 29, line 20, replace the compound

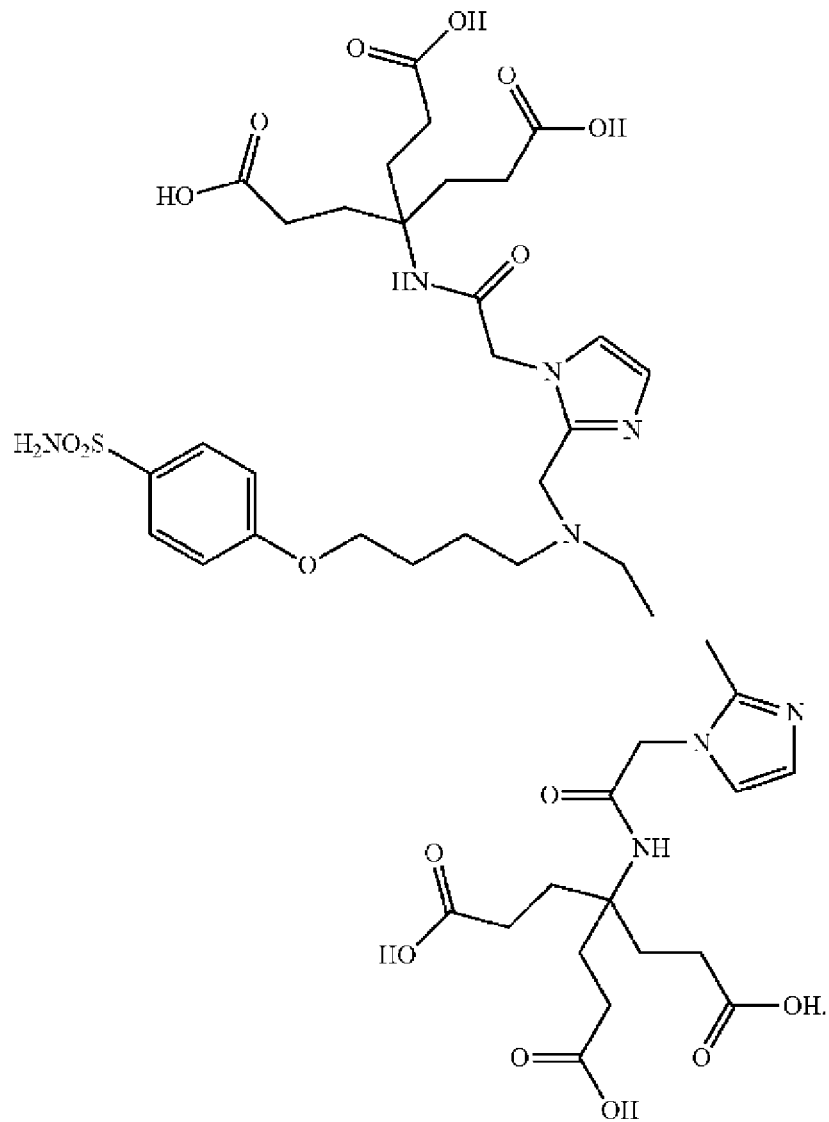

CERTIFICATE OF CORRECTION (continued)
U.S. Pat. No. 9,120,837 B2

Column 82, Claim 29, line 20, Cont'd

With: